United States Patent
Chan

(10) Patent No.: US 12,214,137 B2
(45) Date of Patent: Feb. 4, 2025

(54) TEXTILE TUBE FOR A THERAPY DEVICE

(71) Applicant: RESMED PTY LTD, Bella Vista (AU)

(72) Inventor: Andrew Chan, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 773 days.

(21) Appl. No.: 17/430,145

(22) PCT Filed: Feb. 11, 2020

(86) PCT No.: PCT/IB2020/051079
§ 371 (c)(1),
(2) Date: Aug. 11, 2021

(87) PCT Pub. No.: WO2020/165760
PCT Pub. Date: Aug. 20, 2020

(65) Prior Publication Data
US 2022/0096778 A1   Mar. 31, 2022

Related U.S. Application Data

(60) Provisional application No. 62/805,164, filed on Feb. 13, 2019.

(51) Int. Cl.
*A61M 16/00* (2006.01)
*A61M 16/06* (2006.01)
(Continued)

(52) U.S. Cl.
CPC .... *A61M 16/0875* (2013.01); *A61M 16/0003* (2014.02); *A61M 16/0066* (2013.01);
(Continued)

(58) Field of Classification Search
CPC .......... A61M 16/0627; A61M 16/0875; D03D 3/02; D03D 15/47; D03D 15/497;
(Continued)

(56) References Cited

U.S. PATENT DOCUMENTS 4,437,462 A    3/1984   Piljay et al.
4,714,096 A    12/1987  Guay
(Continued)

FOREIGN PATENT DOCUMENTS

GB    656352 A      8/1951
GB    2 032 044 A   4/1980
(Continued)

OTHER PUBLICATIONS

Extended European Search Report mailed Feb. 2, 2023, in corresponding EP Application No. 20756702.5 (8 pages).
(Continued)

*Primary Examiner* — Kendra D Carter
*Assistant Examiner* — Jaeick Jang
(74) *Attorney, Agent, or Firm* — Nixon & Vanderhye P.C.

(57) ABSTRACT

An air circuit for use in an air therapy device that is lightweight and comfortable for a user that is configured to also limit air leakage. The air circuit may include a tubular structure formed from various textile structures including circular weaving, circular knitting, braiding and other structures.

9 Claims, 36 Drawing Sheets

(51) Int. Cl.
*A61M 16/08* (2006.01)
*D03D 3/02* (2006.01)
*D03D 15/56* (2021.01)
*D03D 15/593* (2021.01)

(52) U.S. Cl.
CPC ...... *A61M 16/024* (2017.08); *A61M 16/0627* (2014.02); *A61M 16/0666* (2013.01); *D03D 3/02* (2013.01); *D03D 15/56* (2021.01); *D03D 15/593* (2021.01); *A61M 2016/0027* (2013.01); *A61M 2016/0033* (2013.01); *A61M 2205/0216* (2013.01); *D10B 2509/00* (2013.01)

(58) Field of Classification Search
CPC .......... D03D 15/56; F16L 11/00; F16L 11/02; F16L 11/085
See application file for complete search history.

(56) References Cited

U.S. PATENT DOCUMENTS

| | | |
|---|---|---|
| 4,782,832 A | 11/1988 | Trimble et al. |
| 4,944,310 A | 7/1990 | Sullivan |
| 5,232,429 A | 8/1993 | Cizek et al. |
| 5,687,715 A | 11/1997 | Landis |
| 5,843,542 A | 12/1998 | Brushafer et al. |
| 6,532,959 B1 | 3/2003 | Berthon-Jones |
| 6,581,594 B1 | 6/2003 | Drew et al. |
| 6,769,431 B2 | 8/2004 | Smith et al. |
| 7,766,050 B2 | 8/2010 | Patel |
| 7,866,944 B2 | 1/2011 | Kenyon et al. |
| 7,926,517 B2 | 4/2011 | Horimoto et al. |
| 8,636,479 B2 | 1/2014 | Kenyon et al. |
| 8,638,014 B2 | 1/2014 | Sears et al. |
| 8,733,349 B2 | 5/2014 | Bath et al. |
| 8,905,082 B2 | 12/2014 | Gray |
| 9,566,408 B2 | 2/2017 | Henry |
| 9,656,038 B2 | 5/2017 | Rummery et al. |
| 10,729,869 B2 | 8/2020 | Rummery |
| 2001/0054422 A1 | 12/2001 | Smith |
| 2004/0045549 A1 | 3/2004 | Smith |
| 2004/0079371 A1 | 4/2004 | Gray |
| 2004/0194781 A1 | 10/2004 | Fukunaga |
| 2006/0165829 A1 | 7/2006 | Smith |
| 2008/0173305 A1 | 7/2008 | Frater |
| 2009/0044808 A1 | 2/2009 | Guney et al. |
| 2009/0050156 A1 | 2/2009 | Ng et al. |
| 2010/0000534 A1 | 1/2010 | Kooij et al. |
| 2010/0018534 A1 | 1/2010 | Veliss et al. |
| 2010/0224195 A1 | 9/2010 | Henry |
| 2014/0102456 A1 | 4/2014 | Ovizinsky et al. |
| 2015/0352306 A1 | 12/2015 | Scheiner et al. |
| 2016/0030698 A1 | 2/2016 | Kolk et al. |
| 2016/0151597 A1* | 6/2016 | Baecke ............. A61M 16/0858 128/204.21 |
| 2016/0296720 A1 | 10/2016 | Henry |
| 2017/0143929 A1 | 5/2017 | Henry |
| 2017/0252529 A1 | 9/2017 | Rummery et al. |
| 2017/0333662 A1 | 11/2017 | Ovizinsky et al. |
| 2018/0043120 A1 | 2/2018 | Hunley |
| 2019/0015192 A1 | 1/2019 | Nakazawa |
| 2019/0015620 A1* | 1/2019 | Ewers .................... F16L 11/02 |

FOREIGN PATENT DOCUMENTS

| | | |
|---|---|---|
| JP | 2001-336678 A | 12/2001 |
| JP | 2003-275228 A | 9/2003 |
| JP | 2009-72596 A | 4/2009 |
| JP | 2014-514035 A | 6/2014 |
| JP | 2014-167343 A | 9/2014 |
| JP | 2018-527156 A | 9/2018 |
| JP | 7413391 B2 | 1/2024 |
| WO | WO 98/004310 A1 | 2/1998 |
| WO | WO 98/034665 A1 | 8/1998 |
| WO | WO 2000/078381 A1 | 12/2000 |
| WO | WO 2004/073778 A1 | 9/2004 |
| WO | WO 2005/063328 A1 | 7/2005 |
| WO | WO 2005/075186 A1 | 8/2005 |
| WO | WO 2006/074513 A1 | 7/2006 |
| WO | WO 2006/130903 A1 | 12/2006 |
| WO | WO 2007/109837 A1 | 10/2007 |
| WO | WO 2009/052560 A1 | 4/2009 |
| WO | WO 2010/135785 A1 | 12/2010 |
| WO | WO 2012/122601 A1 | 9/2012 |
| WO | WO 2012/167327 A1 | 12/2012 |
| WO | WO 2012/171072 A1 | 12/2012 |
| WO | WO 2013/006913 A1 | 1/2013 |
| WO | WO 2013/020167 A1 | 2/2013 |
| WO | WO 2017/213523 A1 | 12/2017 |
| WO | WO 2020/000033 A1 | 1/2020 |

OTHER PUBLICATIONS

Notice of Reasons for Refusal and English translation in corresponding Japanese Application No. 2023-220787, four pages, dated Apr. 30, 2024.
"*Respiratory Physiology*", by John B. West, Lippincott Williams & Wilkins, 9th edition published 2012 (8 pages).
International Search Report mailed 4 May 2020 in corresponding PCT Application PCT/IB2020/051079 (12 pages).
Written Opinion mailed May 4, 2020 in corresponding PCT Application PCT/IB2020/051079 (7 pages).
Notice of Reasons for Rejection and English translation thereof mailed Mar. 22, 2022 in related JP Application 2019-100282 (6 pages).
European Search Report mailed Jul. 11, 2022 in related EP Application 21214525.4 (8 pages).
Notice of Reasons for Rejection and English translation thereof mailed Aug. 1, 2022 in related JP Application 2021-146154 (10 pages).
Pre-Appeal Examination Report and English translation thereof obtained Nov. 8, 2021 in related JP Application 2019-100282 (6 pages).
Office Action mailed Feb. 3, 2022 in related U.S. Appl. No. 16/912,857 (21 pages).

* cited by examiner

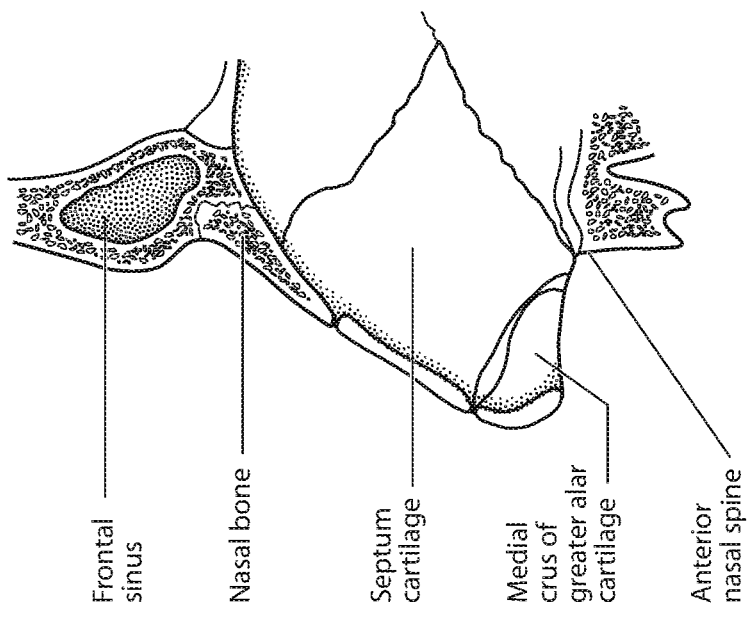
FIG. 2I
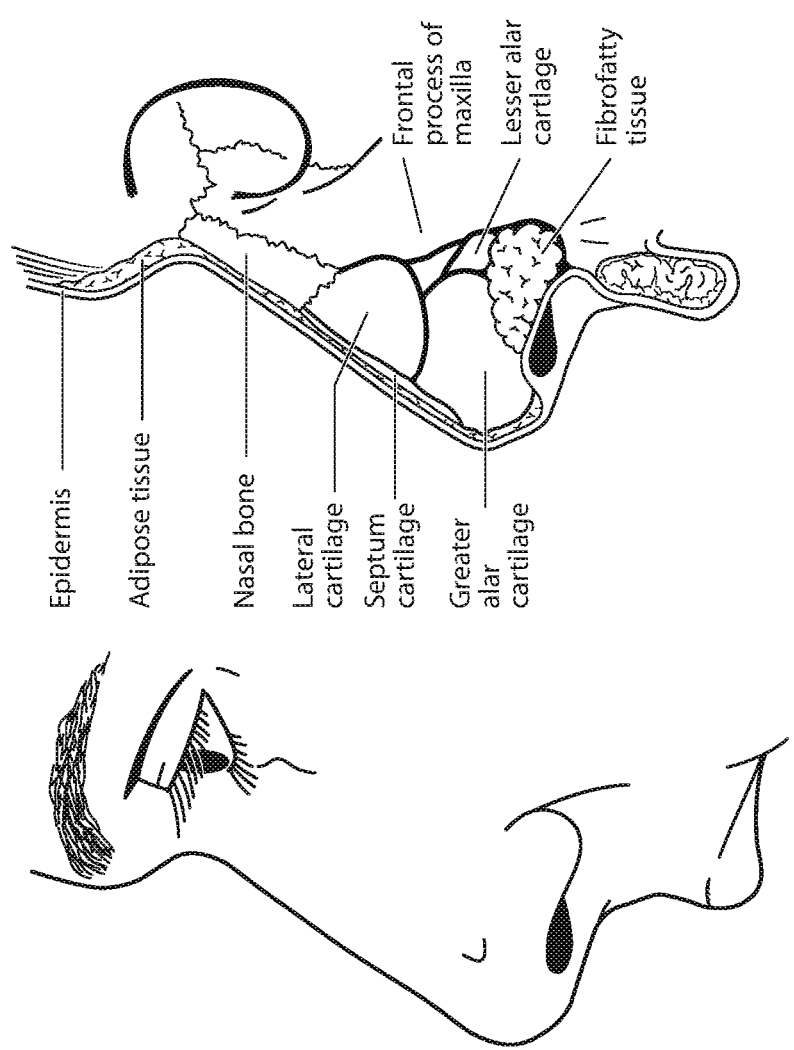
FIG. 2H
FIG. 2G

Relatively Large Positive Curvature

Relatively Small Positive Curvature

Zero Curvature

Relatively Small Negative Curvature

Relatively Large Negative Curvature

Left-hand rule
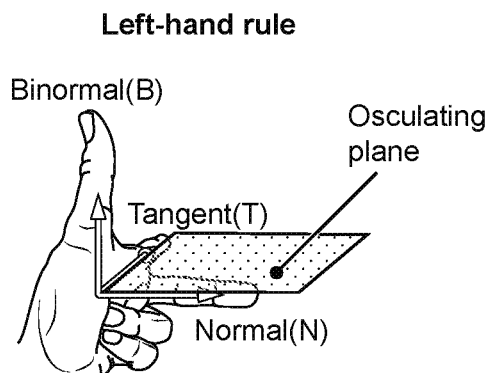
FIG. 3O
Right-hand rule
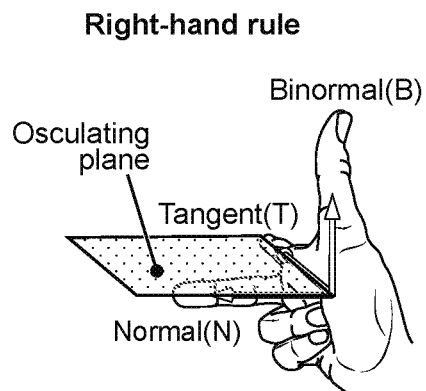
FIG. 3P
Left ear helix
Right ear helix
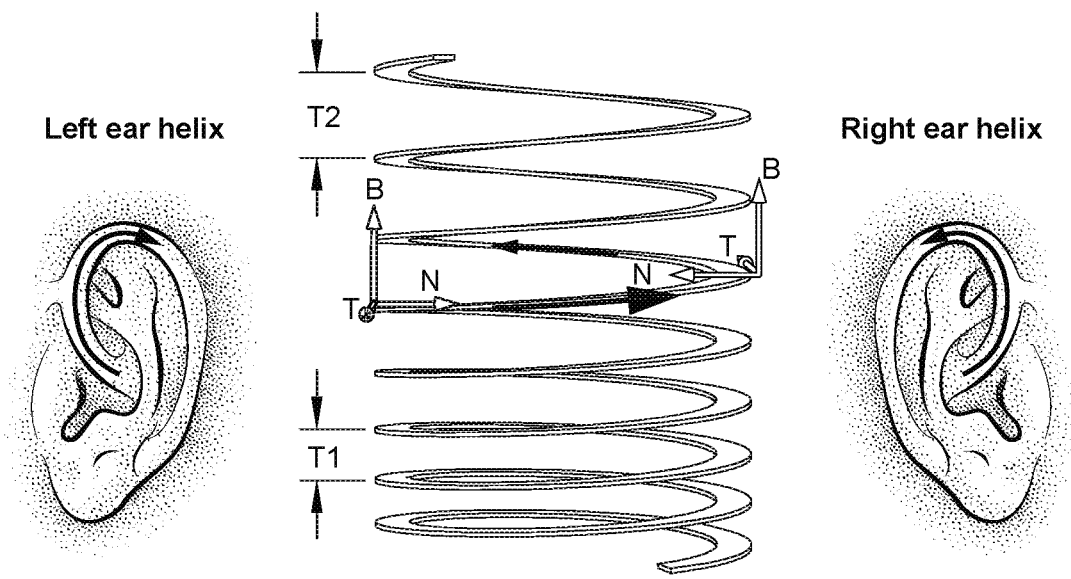
FIG. 3Q
Right-hand helix
Right-hand positive
FIG. 3S
FIG. 3R
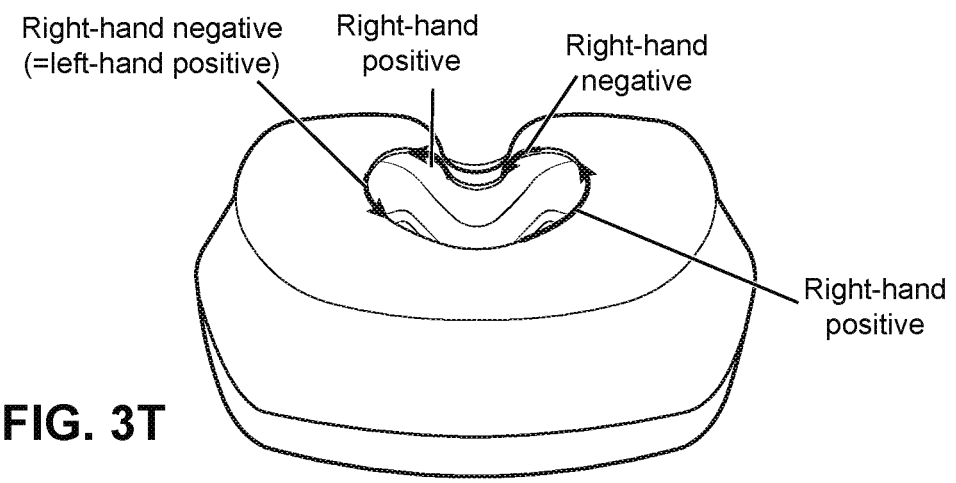
FIG. 3T

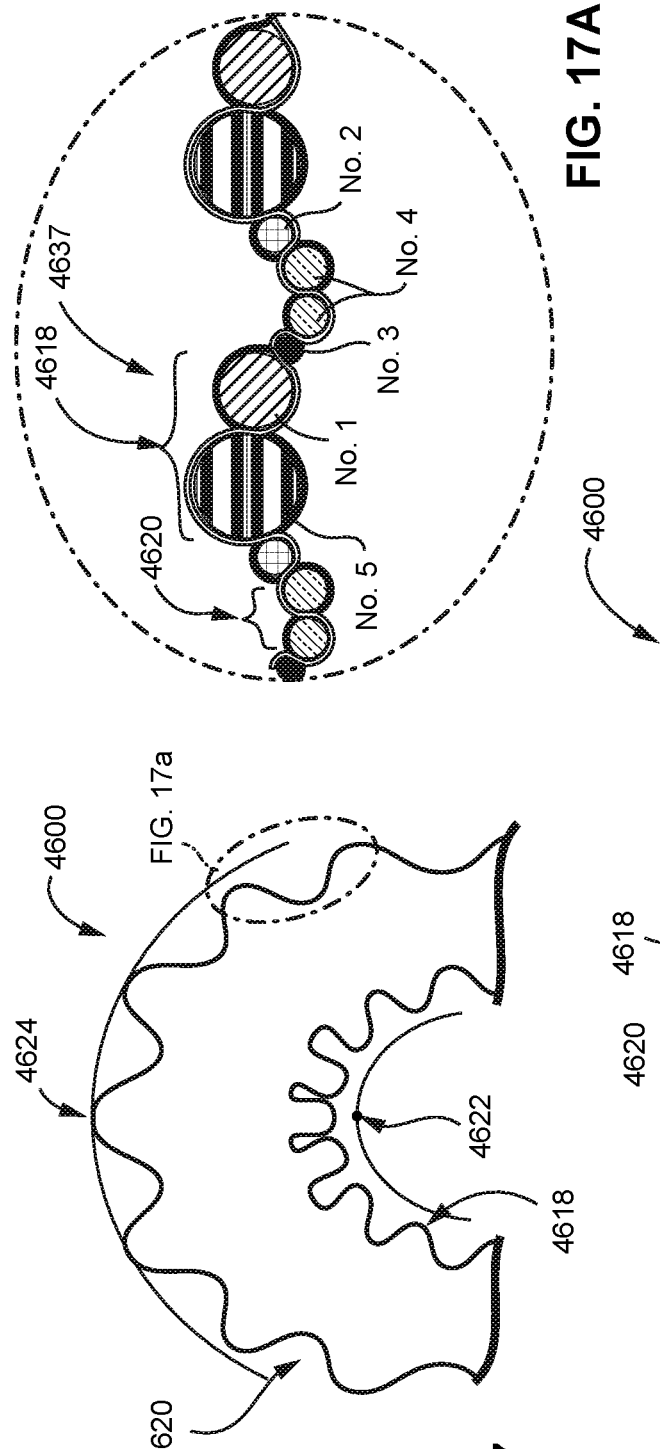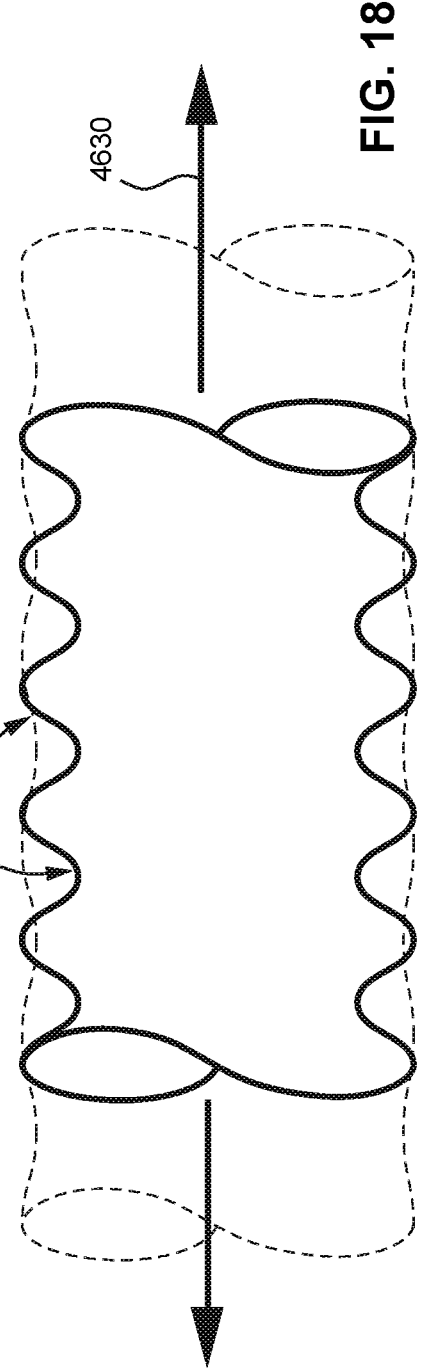

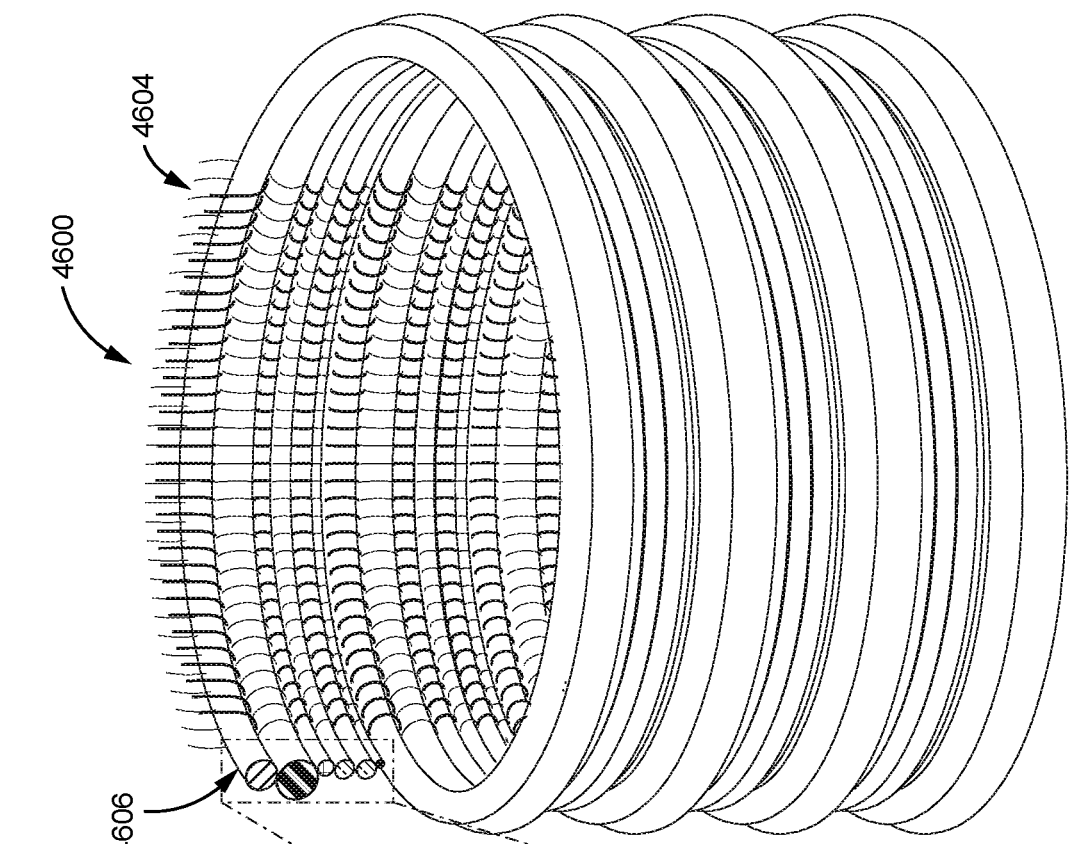
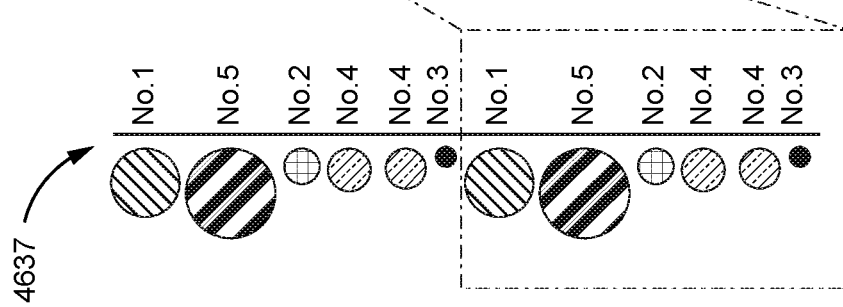
FIG. 20
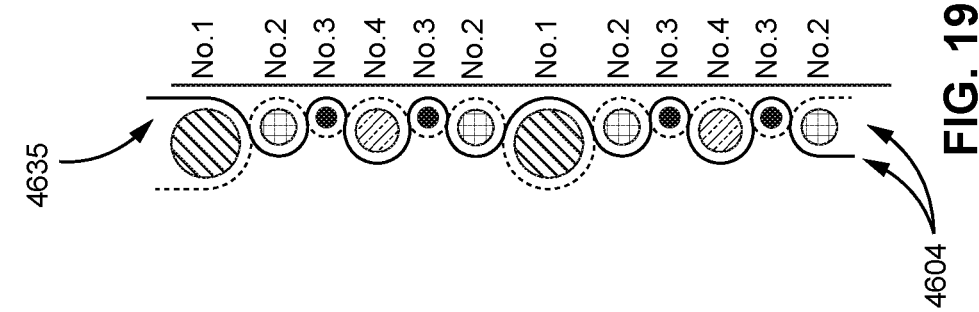
FIG. 19

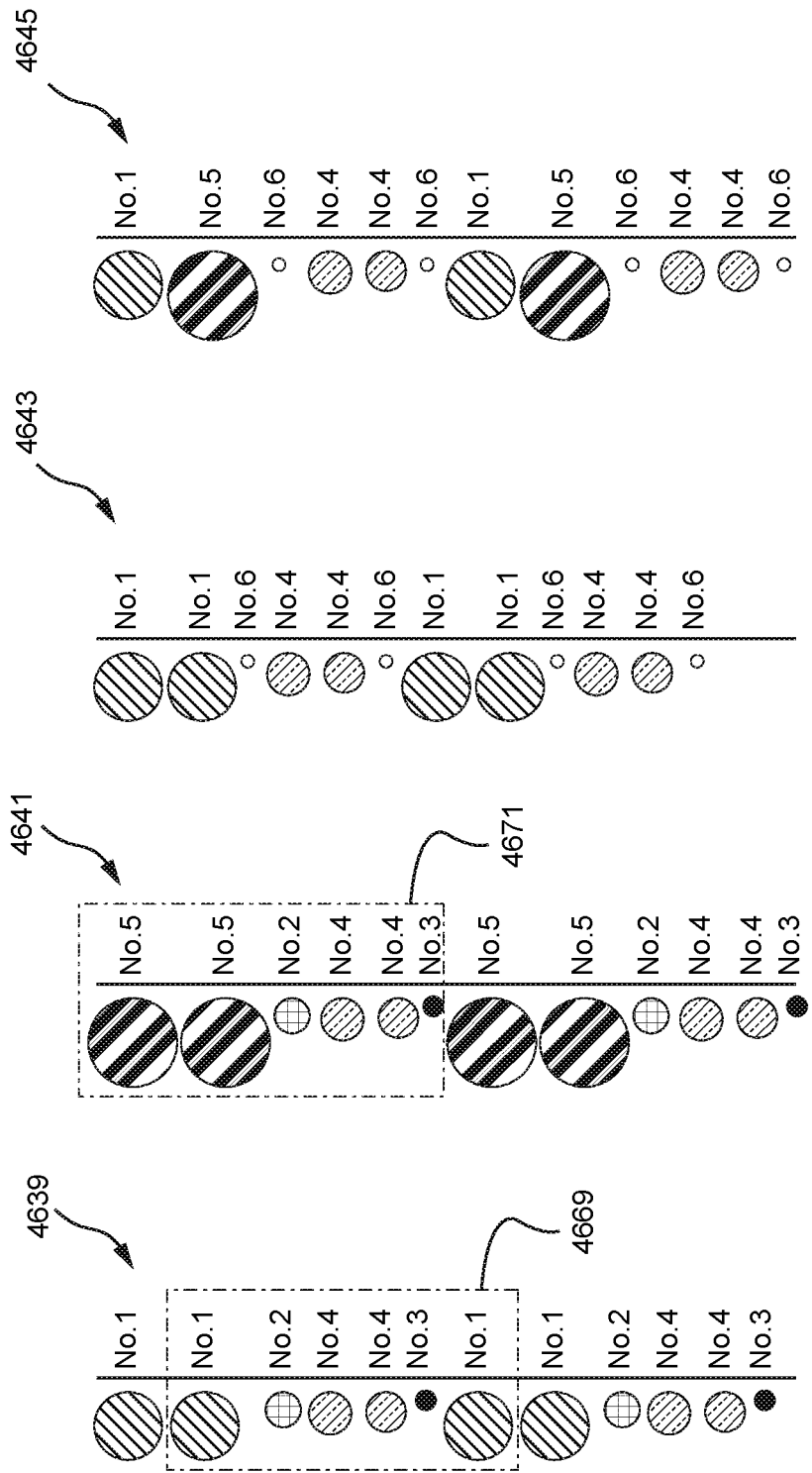

| Thread Number | Thread Material |
|---|---|
| No. 1 | PA Monofilament 0.7 mm |
| No. 2 | PA 6.6 Z150 (880 dtex) |
| No. 3 | PA 6.6 Z300 (440 dtex) |
| No. 4 | Core: Lycra 1880 dtex Coat PES text. Dtex 110f36x1 |
| No. 5 | PA6 monofilament (0.8 mm) |
| No. 6 | Core: Lycra 156 dtex coat PES dtex 76f24x1 |

FIG. 25

| Weft Shuttle | Thread Number for Particular Figures | | | | | |
|---|---|---|---|---|---|---|
| | Fig. 19 | Fig. 20 | Fig. 21 | Fig. 22 | Fig. 23 | Fig. 24 |
| Shuttle 1 | No. 1 | No. 1 | No. 1 | No. 5 | No. 1 | No. 1 |
| Shuttle 2 | No. 2 | No. 5 | No. 1 | No. 5 | No. 1 | No. 5 |
| Shuttle 3 | No. 3 | No. 2 | No. 2 | No. 2 | No. 6 | No. 6 |
| Shuttle 4 | No. 4 | No. 4 | No. 4 | No. 4 | No. 4 | No. 4 |
| Shuttle 5 | No. 3 | No. 4 | No. 3 | No. 4 | No. 4 | No. 4 |
| Shuttle 6 | No. 2 | No. 3 | No. 3 | No. 3 | No. 6 | No. 6 |

FIG. 26

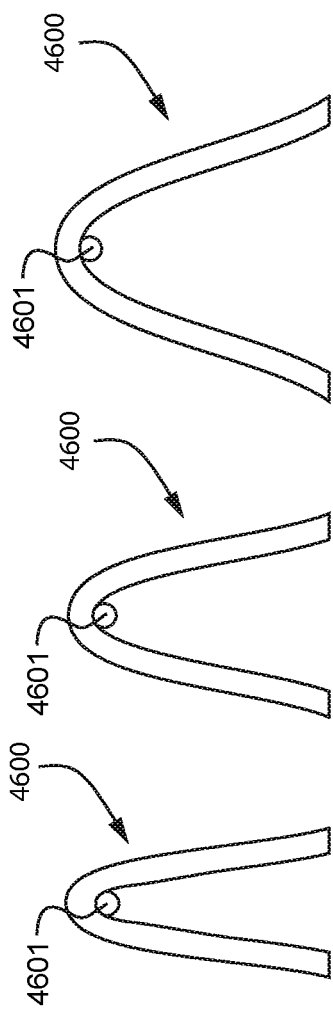
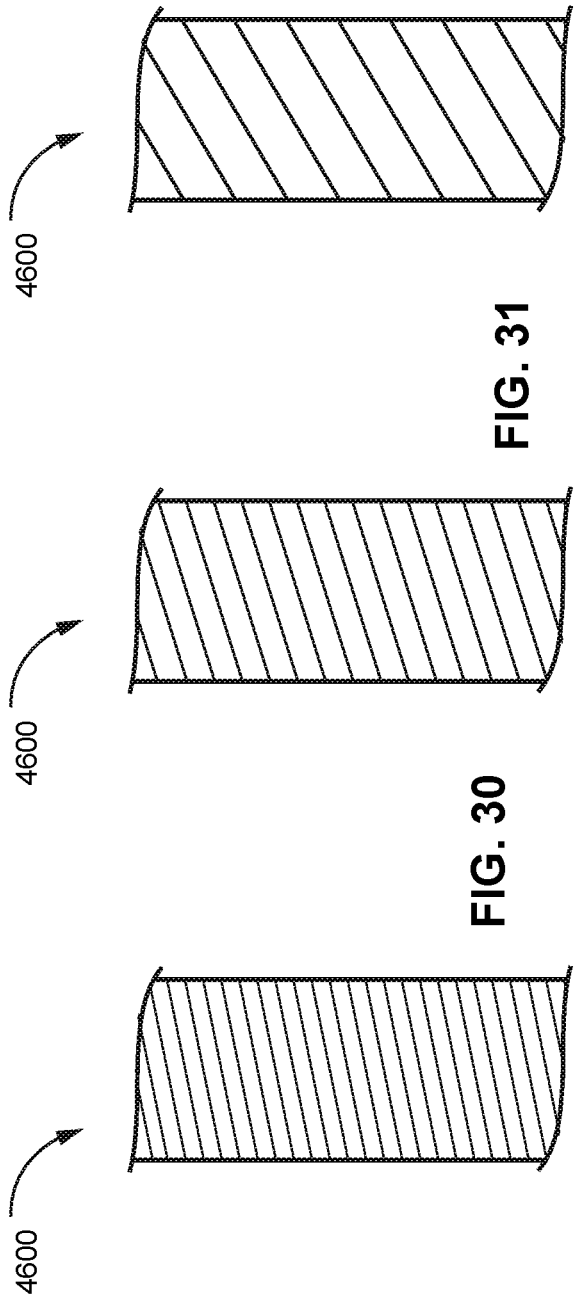

| SELECTION MATRIX | | Thread Type | | | | | |
|---|---|---|---|---|---|---|---|
| Shuttle Position | | No. 1 | No. 2 | No. 3 | No. 4 | No. 5 | No. 6 |
| Shuttle 1 | | Yes/No | Yes/No | Yes/No | Yes/No | Yes/No | Yes/No |
| Shuttle 2 | | Yes/No | Yes/No | Yes/No | Yes/No | Yes/No | Yes/No |
| Shuttle 3 | | Yes/No | Yes/No | Yes/No | Yes/No | Yes/No | Yes/No |
| Shuttle 4 | | Yes/No | Yes/No | Yes/No | Yes/No | Yes/No | Yes/No |
| Shuttle 5 | | Yes/No | Yes/No | Yes/No | Yes/No | Yes/No | Yes/No |
| Shuttle 6 | | Yes/No | Yes/No | Yes/No | Yes/No | Yes/No | Yes/No |

FIG. 35

TEXTILE TUBE FOR A THERAPY DEVICE

1 CROSS-REFERENCE TO RELATED APPLICATIONS

This application is the U.S. national phase of International Application No. PCT/IB2020/051079 filed Feb. 11, 2020 which designated the U.S. and claims priority to U.S. Provisional Application No. 62/805,164, filed Feb. 13, 2019, the entire contents of each of which are hereby incorporated by reference.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Various therapies, such as Continuous Positive Airway Pressure (CPAP) therapy, Non-invasive ventilation (NW) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to screen, diagnose, or monitor a condition without treating it.

A treatment system may comprise a Respiratory Pressure Therapy Device (RPT device), an air circuit, a humidifier, a patient interface, and data management.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

2.2.3.2 Respiratory Pressure Therapy (RPT) Device

A respiratory pressure therapy (RPT) device may be used individually or as part of a system to implement one or more of a number of therapies described above, such as by operating the device to generate a flow of air for delivery to an interface to the airways. The flow of air may be pressurised. Examples of RPT devices include a CPAP device and a ventilator.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

2.2.3.4 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.5 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

An aspect of the present technology is related to an apparatus for providing positive pressure respiratory therapy to a patient breathing in a respiratory cycle including an inhalation portion and an exhalation portion, said apparatus comprising: a controllable motor-blower configured to generate a supply of air at a positive pressure relative to ambient pressure by rotating an impeller at an impeller speed and communicate said supply air at said positive pressure from the motor-blower to a patient interface via an air circuit in use, wherein the air circuit comprises a tubular structure.

An aspect of the present technology is related to a patient interface comprising: 1) a plenum chamber pressurisable to a therapeutic pressure of at least 6 cmH$_2$O above ambient air pressure, said plenum chamber including a plenum chamber inlet port sized and structured to receive a flow of air at the therapeutic pressure for breathing by a patient; 2) a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use; 3) a positioning and stabilising structure to provide a force to hold the seal-forming structure in a therapeutically effective position on the patient's head, the positioning and stabilising structure comprising a tie, the tie being constructed and arranged so that at least a portion overlies a region of the patient's head superior to an otobasion superior of the patient's head in use; and 4) a tubular structure for delivering air to the plenum chamber, the tubular structure having a circular woven structure.

One form of the present technology comprises an air circuit for use in an air therapy device. The air circuit may include a tubular structure. The tubular structure may have circular woven structure. The tubular structure may be seamless along a length of the tubular structure. The tubular structure may include a plurality of warp threads and a plurality of weft threads. The tubular structure may include a first weft position, a second weft position, a third weft section comprising at least one weft position, and a fourth weft position. The plurality of weft threads may include a first weft thread and a second weft thread. The first weft thread may be located in the first weft position adjacent to the second weft thread in the second weft position. The first weft thread may be a first monofilament strand and the second weft thread may be a second monofilament strand. The second weft thread may be adjacent at least one multifilament thread in the third weft section. The first weft thread may be located in the fourth weft position.

The plurality of weft threads may include a first monofilament weft thread and a second monofilament weft thread. The first monofilament weft thread may be located adjacent to at least one non-monofilament weft thread and the second monofilament weft thread may also be located adjacent to at least one non-monofilament thread. The at least on non-monofilament thread may be located between the first monofilament weft thread and the second monofilament weft thread.

In examples, (a) the first monofilament strand may be 0.7 millimeters in diameter, (b) the plurality of warp threads may include 252 warp threads, (c) an outer diameter of the tubular structure may be greater than 18 millimeters, (d) the third weft section may comprise at least four weft positions, (e) the plurality of warp threads may be formed of the same material, (f) the at least four weft positions may comprise a first weft section position, a second weft section position, a third weft section position, and a fourth weft section position, (g) a first thread composition in the first weft section position may be the same as a fourth thread composition in the fourth weft section position, and (h) a second thread composition in the second weft section position may be the same as a third thread composition in the third weft section position.

Another aspect of one form of the present technology comprises an air circuit. The air circuit may include a tubular structure. The tubular structure may have a circular woven structure. The tubular structure may be seamless along a length of the tubular structure. The tubular structure may include a plurality of warp threads and a plurality of weft threads. The plurality of weft threads may include a first monofilament weft thread and a second monofilament weft thread. The first monofilament weft thread may be located adjacent to at least one non-monofilament weft thread. The second monofilament weft thread also may be located adjacent to at least one non-monofilament thread. The at least one non-monofilament thread may be located between the first monofilament weft thread and the second monofilament weft thread.

In examples according to the preceding paragraph, (a) the first monofilament strand may be 0.7 millimeters in diameter, (b) the plurality of warp threads may include 252 warp threads, (c) an outer diameter of the tubular structure may be greater than 18 millimeters, (d) the third weft section may comprise at least four weft positions, (e) the plurality of warp threads may be formed of the same material, (f) the at least four weft positions may comprise a first weft section position, a second weft section position, a third weft section position, and a fourth weft section position, (g) a first thread composition in the first weft section position may be the same as a fourth thread composition in the fourth weft section position, and (h) a second thread composition in the second weft section position may be the same as a third thread composition in the third weft section position, (i) a first non-monofilament thread in the first weft position may have a same composition same as a fourth non-monofilament thread in the fourth weft position, (j) a second non-monofilament thread in the second weft position may have a same composition as a third non-monofilament thread in the third weft position, (k) the first non-monofilament thread may be located adjacent to the first monofilament thread and the fourth non-monofilament thread is located adjacent to the second monofilament thread.

In an example the air circuit may be included in an apparatus for providing positive pressure respiratory therapy to a patient breathing in a respiratory cycle including an inhalation portion and an exhalation portion. The apparatus may include a controllable motor-blower configured to generate a supply of air at a positive pressure relative to ambient pressure by rotating an impeller at an impeller speed. The apparatus may include a housing holding said motor-blower. The housing may include an inlet and a patient-connection port. The patient-connection port may be structured to communicate said supply air at said positive pressure from the motor-blower to a patient interface via the air circuit in use. The apparatus may include a sensor to monitor at least one of pressure and a flow rate of the supply of air at positive pressure and to generate a sensor output. The apparatus may include a controller configured to adjust an operating parameter of said motor-blower in accordance with said sensor output to maintain a minimum positive pressure in said patient interface during a treatment session by causing an increase in the impeller speed during the inhalation portion of the respiratory cycle and causing a decrease in the impeller speed during the exhalation portion of the breathing cycle.

In an example, the air circuit may be included in a patient interface. The patient interface may include a plenum chamber pressurisable to a therapeutic pressure of at least 6 cmH$_2$O above ambient air pressure. The plenum chamber may include a plenum chamber inlet port sized and structured to receive a flow of air at the therapeutic pressure for breathing by a patient. The patient interface may include a seal-forming structure constructed and arranged to form a seal with a region of the patient's face surrounding an entrance to the patient's airways. The seal-forming structure may have a hole therein such that the flow of air at said therapeutic pressure is delivered to at least an entrance to the patient's nares. The seal-forming structure may be constructed and arranged to maintain said therapeutic pressure in the plenum chamber throughout the patient's respiratory cycle in use. The patient interface may include a positioning and stabilising structure to provide a force to hold the seal-forming structure in a therapeutically effective position on the patient's head. The positioning and stabilising structure may comprise a tie. The tie may be constructed and arranged so that at least a portion overlies a region of the patient's head superior to an otobasion superior of the patient's head in use. The patient interface may include a vent structure to allow a continuous flow of gases exhaled by the patient from an interior of the plenum chamber to ambient. The vent structure may be sized and shaped to maintain the therapeutic pressure in the plenum chamber in use. The patient interface may be configured to allow the patient to breath from ambient through their mouth in the absence of a flow of pressurised air through the plenum chamber inlet port, or the patient interface may be configured to leave the patient's mouth uncovered.

Another aspect of one form of the present technology comprises a tubular structure for delivering air to the plenum chamber. The tubular structure may have a circular woven structure and including an exterior surface and an interior surface. The tubular structure may have a circular woven structure with a weft density of at least 30 threads per 10 cm and at least 168 warp threads. The tubular structure may include a first weft thread that is stiffer than an adjacent second thread. The first weft thread may resist occlusion of the tubular structure when subjected to perpendicular force. The first thread may be located between warp threads such that the first thread is integrated into the woven structure of the tubular structure. The tubular structure may further comprise a sealing structure with an outer surface that lines the interior surface of the tubular structure. An inner surface may bound a channel of the tubular structure for directing air. The channel may be configured to deliver air at therapeutic pressure with a non-zero leak rate.

In examples according to the preceding paragraph, (a) the tubular structure may include 252 warp threads, (b) the tubular structure may be continuously formed without seams along an entire length of the tubular structure, (c) the tubular structure may include at least two separate monofilament strands in a weft direction, wherein a first monofilament strand is located adjacent the second monofilament strand.

In an example the tubular structure may be included in an apparatus for providing positive pressure respiratory therapy to a patient breathing in a respiratory cycle including an inhalation portion and an exhalation portion. The apparatus may include a controllable motor-blower configured to generate a supply of air at a positive pressure relative to ambient pressure by rotating an impeller at an impeller speed. The apparatus may include a housing holding said motor-blower. The housing may include an inlet and a patient-connection port. The patient-connection port may be structured to communicate said supply air at said positive pressure from the motor-blower to a patient interface via an air circuit in use. The apparatus may include a sensor to monitor at least one of pressure and a flow rate of the supply of air at positive pressure and to generate a sensor output. The apparatus may include a controller configured to adjust an operating parameter of said motor-blower in accordance with said sensor output to maintain a minimum positive pressure in said patient interface during a treatment session by causing an increase in the impeller speed during the inhalation portion of the respiratory cycle and causing a decrease in the impeller speed during the exhalation portion of the breathing cycle.

In an example, the tubular structure may be included in a patient interface. The patient interface may include a plenum chamber pressurisable to a therapeutic pressure of at least 6 cmH$_2$O above ambient air pressure. The plenum chamber may include a plenum chamber inlet port sized and structured to receive a flow of air at the therapeutic pressure for breathing by a patient. The patient interface may include a seal-forming structure constructed and arranged to form a seal with a region of the patient's face surrounding an entrance to the patient's airways. The seal-forming structure may have a hole therein such that the flow of air at said therapeutic pressure is delivered to at least an entrance to the patient's nares. The seal-forming structure may be constructed and arranged to maintain said therapeutic pressure in the plenum chamber throughout the patient's respiratory cycle in use. The patient interface may include a positioning and stabilising structure to provide a force to hold the seal-forming structure in a therapeutically effective position on the patient's head. The positioning and stabilising structure may comprise a tie. The tie may be constructed and arranged so that at least a portion overlies a region of the patient's head superior to an otobasion superior of the patient's head in use. The patient interface may include a vent structure to allow a continuous flow of gases exhaled by the patient from an interior of the plenum chamber to ambient. The vent structure may be sized and shaped to maintain the therapeutic pressure in the plenum chamber in use. The patient interface may be configured to allow the patient to breath from ambient through their mouth in the absence of a flow of pressurised air through the plenum chamber inlet port, or the patient interface may be configured to leave the patient's mouth uncovered.

Another aspect of one form of the present technology comprises an air circuit. The air circuit may include a seamless textile tubular structure. The air circuit may include an exterior surface of the tubular structure that may be ribbed. A ribbed structure may be formed with peaks and valleys. Weft threads located at the peaks may be have different elasticities than weft threads located at the valleys.

In examples according to the preceding paragraph, (a) the weft threads located at the peaks may be less elastic than the weft threads located at the valleys, (b) weft threads between the peaks and the valleys may have elasticities that are between the elasticity of the weft threads located at the peaks and the elasticity of the weft threads located at the valleys.

Another aspect of one form of the present technology comprises an air circuit. The air circuit may include a sealing structure that covers the interior surface of the tubular structure to reduce air loss through the tubular structure. The sealing structure may weigh less than 75% of a weight of the tubular structure.

In examples according to the preceding paragraph, (a) the sealing structure may be formed of silicone, (b) the sealing structure may be formed of acrylate, (c) the sealing structure may be applied to the interior surface via spraying, (d) the sealing structure may be separately formed and adhered to the interior surface, (e) the tubular structure may be woven over the sealing structure.

Another aspect of one form of the present technology comprises an air circuit. The air circuit may include a seamless textile tubular structure. The air circuit may include an exterior surface of the tubular structure that may be ribbed and an interior surface of the tubular structure that may be ribbed. The air circuit may include a sealing structure that covers the interior surface of the tubular structure to reduce air loss through the tubular structure. The sealing structure may weigh less than 75% of a weight of the tubular structure.

In examples according to the preceding paragraph, (a) the tubular structure may be a circular woven structure that includes monofilament and non-monofilament threads, (b) the air circuit may be configured to deliver air at a therapeutic pressure to a patient, wherein the air circuit is configured to have a leak rate less than 2.5 mL/min per meter when delivering air at a therapeutic pressure, (c) the tubular structure may be formed of a different material than the sealing structure, (d) the sealing structure may be formed of an elastomeric material, (e) a portion of the interior surface of the tubular structure may have a positive curvature at a first magnitude, wherein the sealing structure has an inner surface and an outer surface, the outer surface of the sealing structure may have a negative curvature at the first magnitude adjacent the portion of the interior surface and the inner surface of the sealing structure may have a positive curvature of the first magnitude, (f) the sealing structure may mate with a length of the interior surface of the tubular structure from a first rib to a second rib, wherein a thickness of the sealing structure may be substantially constant along the length from the first rib to the second rib.

In an example the air circuit may be included in an apparatus for providing positive pressure respiratory therapy to a patient breathing in a respiratory cycle including an inhalation portion and an exhalation portion. The apparatus may include a controllable motor-blower configured to generate a supply of air at a positive pressure relative to ambient pressure by rotating an impeller at an impeller speed. The apparatus may include a housing holding said motor-blower. The housing may include an inlet and a patient-connection port. The patient-connection port may be structured to communicate said supply air at said positive pressure from the motor-blower to a patient interface via the air circuit in use. The apparatus may include a sensor to monitor at least one of pressure and a flow rate of the supply of air at positive pressure and to generate a sensor output. The apparatus may include a controller configured to adjust an operating parameter of said motor-blower in accordance with said sensor output to maintain a minimum positive pressure in said patient interface during a treatment session by causing an increase in the impeller speed during the inhalation portion of the respiratory cycle and causing a decrease in the impeller speed during the exhalation portion of the breathing cycle.

In an example, the air circuit may be included in a patient interface. The patient interface may include a plenum chamber pressurisable to a therapeutic pressure of at least 6 cmH$_2$O above ambient air pressure. The plenum chamber may include a plenum chamber inlet port sized and structured to receive a flow of air at the therapeutic pressure for breathing by a patient. The patient interface may include a seal-forming structure constructed and arranged to form a seal with a region of the patient's face surrounding an entrance to the patient's airways. The seal-forming structure may have a hole therein such that the flow of air at said therapeutic pressure is delivered to at least an entrance to the patient's nares. The seal-forming structure may be constructed and arranged to maintain said therapeutic pressure in the plenum chamber throughout the patient's respiratory cycle in use. The patient interface may include a positioning and stabilising structure to provide a force to hold the seal-forming structure in a therapeutically effective position on the patient's head. The positioning and stabilising structure may comprise a tie. The tie may be constructed and arranged so that at least a portion overlies a region of the patient's head superior to an otobasion superior of the patient's head in use. The patient interface may include a vent structure to allow a continuous flow of gases exhaled by the patient from an interior of the plenum chamber to ambient. The vent structure may be sized and shaped to maintain the therapeutic pressure in the plenum chamber in use. The patient interface may be configured to allow the patient to breath from ambient through their mouth in the absence of a flow of pressurised air through the plenum chamber inlet port, or the patient interface may be configured to leave the patient's mouth uncovered.

Another aspect of one form of the present technology comprises an apparatus for providing positive pressure respiratory therapy to a patient breathing in a respiratory cycle including an inhalation portion and an exhalation portion. The apparatus may include a controllable motor-blower configured to generate a supply of air at a positive pressure relative to ambient pressure by rotating an impeller at an impeller speed. The apparatus may include a housing holding said motor-blower. The housing may include an inlet and a patient-connection port. The patient-connection port may be structured to communicate said supply air at said positive pressure from the motor-blower to a patient interface via the air circuit in use. The apparatus may include a sensor to monitor at least one of pressure and a flow rate of the supply of air at positive pressure and to generate a sensor output. The apparatus may include a controller configured to adjust an operating parameter of said motor-blower in accordance with said sensor output to maintain a minimum positive pressure in said patient interface during a treatment session by causing an increase in the impeller speed during the inhalation portion of the respiratory cycle and causing a decrease in the impeller speed during the exhalation portion of the breathing cycle. The air circuit may include a tubular structure. The tubular structure may have a circular woven structure. The tubular structure may be seamless along a length of the tubular structure. The tubular structure may include a plurality of warp threads and a plurality of weft threads. The plurality of weft threads may include a first monofilament weft thread and a second monofilament weft thread. The first monofilament weft thread may be located adjacent to at least one non-monofilament weft thread. The second monofilament weft thread also may be located adjacent to at least one non-monofilament thread. The at least one non-monofilament thread may be located between the first monofilament weft thread and the second monofilament weft thread.

In examples according to the preceding paragraph, (a) the first monofilament strand may be 0.7 millimeters in diameter, (b) the plurality of warp threads may include 252 warp threads, (c) an outer diameter of the tubular structure may be greater than 18 millimeters, (d) the third weft section may comprise at least four weft positions, (e) the plurality of warp threads may be formed of the same material, (f) the at least four weft positions may comprise a first weft section position, a second weft section position, a third weft section position, and a fourth weft section position, (g) a first thread composition in the first weft section position may be the same as a fourth thread composition in the fourth weft section position, and (h) a second thread composition in the second weft section position may be the same as a third thread composition in the third weft section position, (i) a first non-monofilament thread in the first weft position may have a same composition same as a fourth non-monofilament thread in the fourth weft position, (j) a second non-monofilament thread in the second weft position may have a same composition as a third non-monofilament thread in the third weft position, (k) the first non-monofilament thread may be located adjacent to the first monofilament thread and the fourth non-monofilament thread is located adjacent to the second monofilament thread.

Another aspect of one form of the present technology comprises a patient interface. The patient interface may include a plenum chamber pressurisable to a therapeutic pressure of at least 6 cmH$_2$O above ambient air pressure. The plenum chamber may include a plenum chamber inlet port sized and structured to receive a flow of air at the therapeutic pressure for breathing by a patient. The patient interface may include a seal-forming structure constructed and arranged to form a seal with a region of the patient's face surrounding an entrance to the patient's airways. The seal-forming structure may have a hole therein such that the flow of air at said therapeutic pressure is delivered to at least an entrance to the patient's nares. The seal-forming structure may be constructed and arranged to maintain said therapeutic pressure in the plenum chamber throughout the patient's respiratory cycle in use. The patient interface may include a positioning and stabilising structure to provide a force to hold the seal-forming structure in a therapeutically effective position on the patient's head. The positioning and stabilising structure may comprise a tie. The tie may be constructed and arranged so that at least a portion overlies a region of the patient's head superior to an otobasion superior of the patient's head in use. The patient interface may include a vent structure to allow a continuous flow of gases exhaled by the patient from an interior of the plenum chamber to ambient. The vent structure may be sized and shaped to maintain the therapeutic pressure in the plenum chamber in use. The patient interface may be configured to allow the patient to breath from ambient through their mouth in the absence of a flow of pressurised air through the plenum chamber inlet port, or the patient interface may be configured to leave the patient's mouth uncovered. A tubular structure for delivering air to the plenum chamber. The tubular structure may have a circular woven structure and including an exterior surface and an interior surface. The tubular structure may have a circular woven structure with a weft density of at least 30 threads per 10 cm and at least 168 warp threads. The tubular structure may include a first weft thread that is stiffer than an adjacent second thread. The first weft thread may resist occlusion of the tubular structure when subjected to perpendicular force. The first thread may be located between warp threads such that the first thread is integrated into the woven structure of the tubular structure. The tubular structure may further comprise a sealing structure with an outer surface that lines the interior surface of the tubular structure. An inner surface may bound a channel of the tubular structure for directing air. The channel may be configured to deliver air at therapeutic pressure with a non-zero leak rate.

In examples according to the preceding paragraph, (a) the tubular structure may include 252 warp threads, (b) the tubular structure may be continuously formed without seams along an entire length of the tubular structure, (c) the tubular structure may include at least two separate monofilament strands in a weft direction, wherein a first monofilament strand is located adjacent the second monofilament strand.

Another aspect of one form of the present technology comprises an apparatus for providing positive pressure respiratory therapy to a patient breathing in a respiratory cycle including an inhalation portion and an exhalation portion. The apparatus may include a controllable motor-blower configured to generate a supply of air at a positive pressure relative to ambient pressure by rotating an impeller at an impeller speed. The apparatus may include a housing holding said motor-blower. The housing may include an inlet and a patient-connection port. The patient-connection port may be structured to communicate said supply air at said positive pressure from the motor-blower to a patient interface via an air circuit in use. The apparatus may include a sensor to monitor at least one of pressure and a flow rate of the supply of air at positive pressure and to generate a sensor output. The apparatus may include a controller configured to adjust an operating parameter of said motor-blower in accordance with said sensor output to maintain a minimum positive pressure in said patient interface during a treatment session by causing an increase in the impeller speed during the inhalation portion of the respiratory cycle and causing a decrease in the impeller speed during the exhalation portion of the breathing cycle. The air circuit may include a seamless textile tubular structure. The air circuit may include an exterior surface of the tubular structure that may be ribbed and an interior surface of the tubular structure that may be ribbed. The air circuit may include a sealing structure that covers the interior surface of the tubular structure to reduce air loss through the tubular structure. The sealing structure may weigh less than 75% of a weight of the tubular structure.

In examples according to the preceding paragraph, (a) the tubular structure may be a circular woven structure that includes monofilament and non-monofilament threads, (b) the air circuit may be configured to deliver air at a therapeutic pressure to a patient, wherein the air circuit is configured to have a leak rate less than 2.5 mL/min per meter when delivering air at a therapeutic pressure, (c) the tubular structure may be formed of a different material than the sealing structure, (d) the sealing structure may be formed of an elastomeric material, (e) a portion of the interior surface of the tubular structure may have a positive curvature at a first magnitude, wherein the sealing structure has an inner surface and an outer surface, the outer surface of the sealing structure may have a negative curvature at the first magnitude adjacent the portion of the interior surface and the inner surface of the sealing structure may have a positive curvature of the first magnitude, (f) the sealing structure may mate with a length of the interior surface of the tubular structure from a first rib to a second rib, wherein a thickness of the sealing structure may be substantially constant along the length from the first rib to the second rib.

Another aspect of one form of the present technology is a patient interface that is moulded or otherwise constructed with a perimeter shape which is complementary to that of an intended wearer.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

Figure 1A:
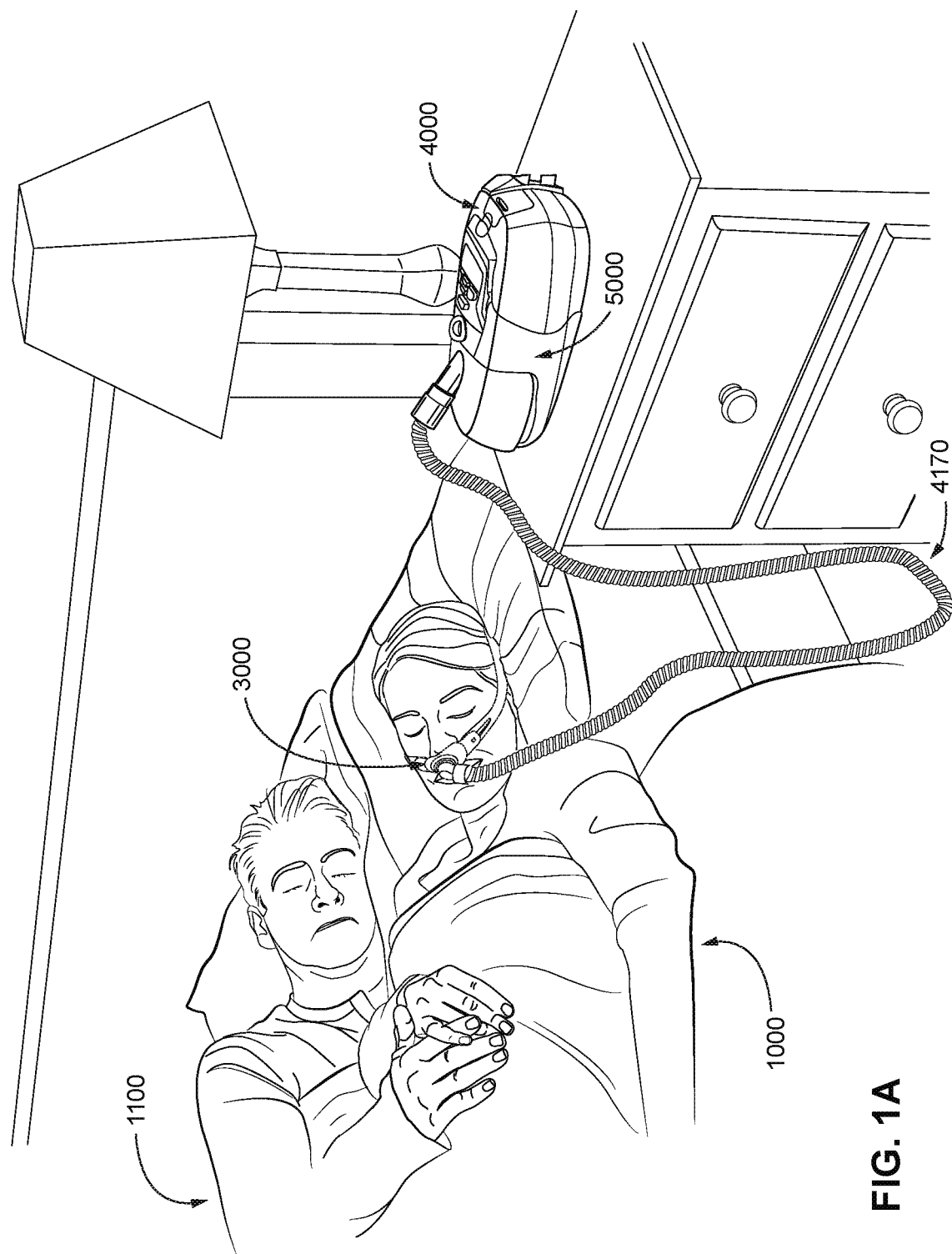
Figure 1B:
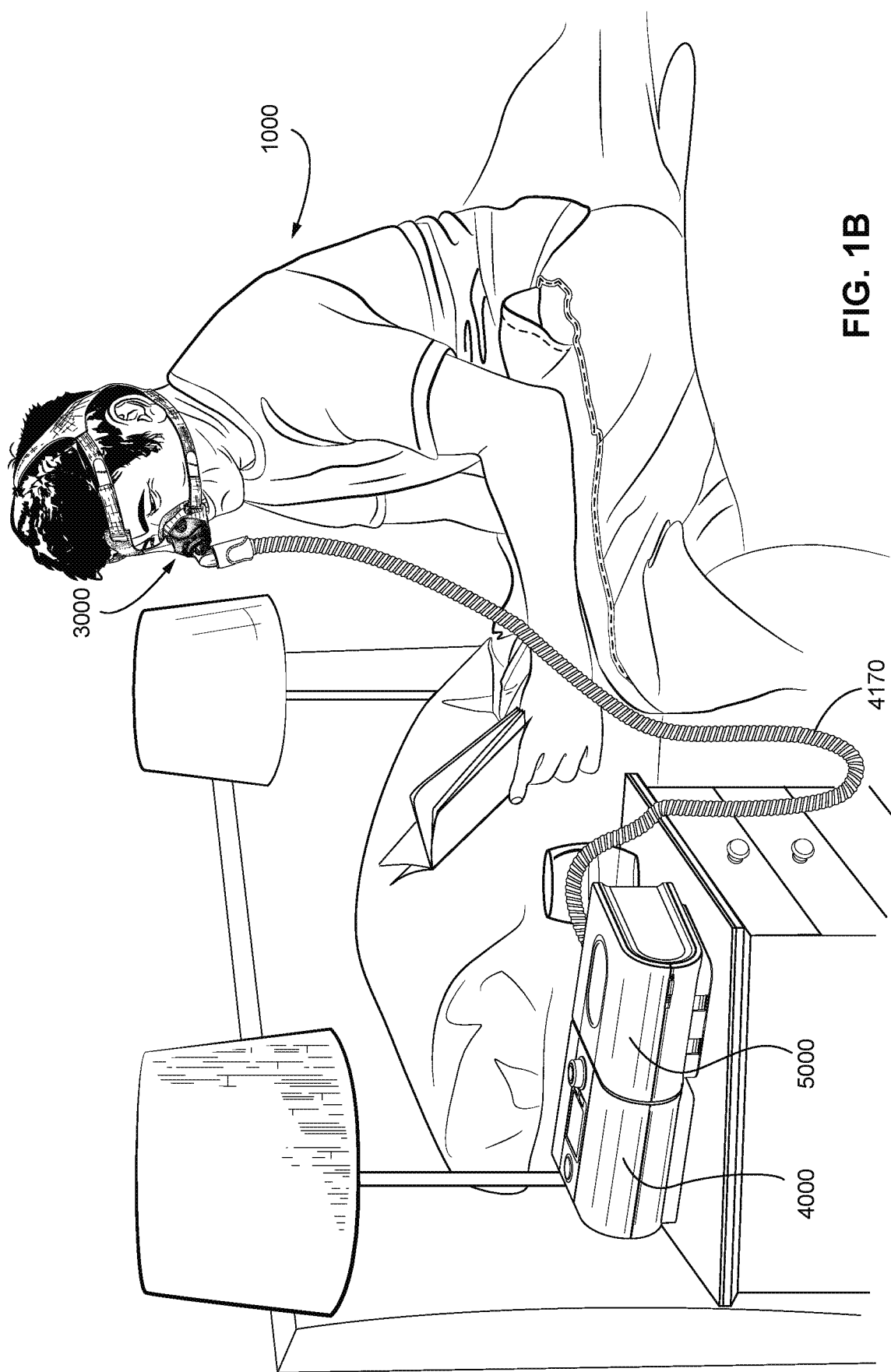
Figure 1C:
Figure 2A:
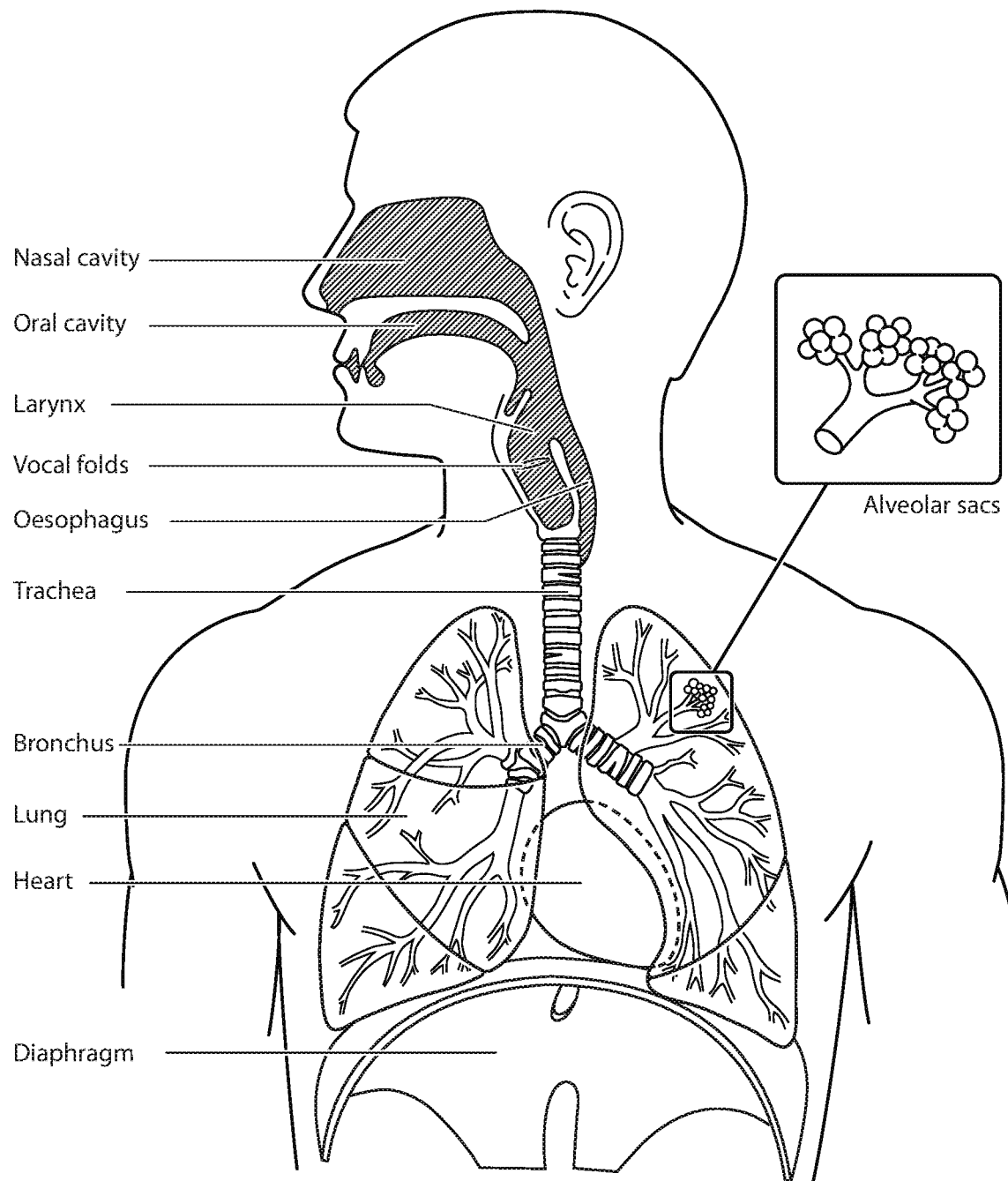
FIG. 2A shows an overview of a human respiratory system including the nasal and oral cavities, the larynx, vocal folds, oesophagus, trachea, bronchus, lung, alveolar sacs, heart and diaphragm.
Figure 2B:
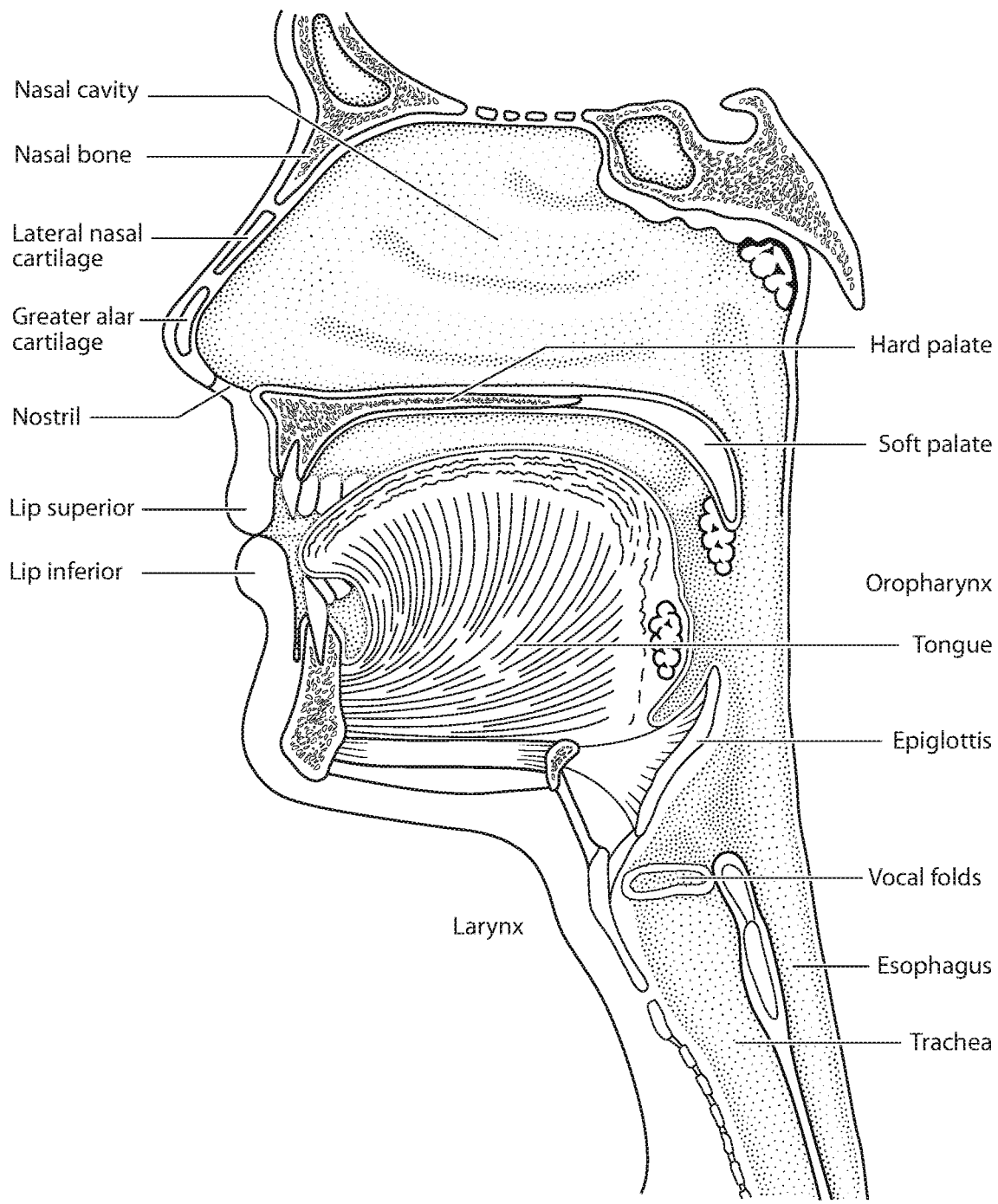
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
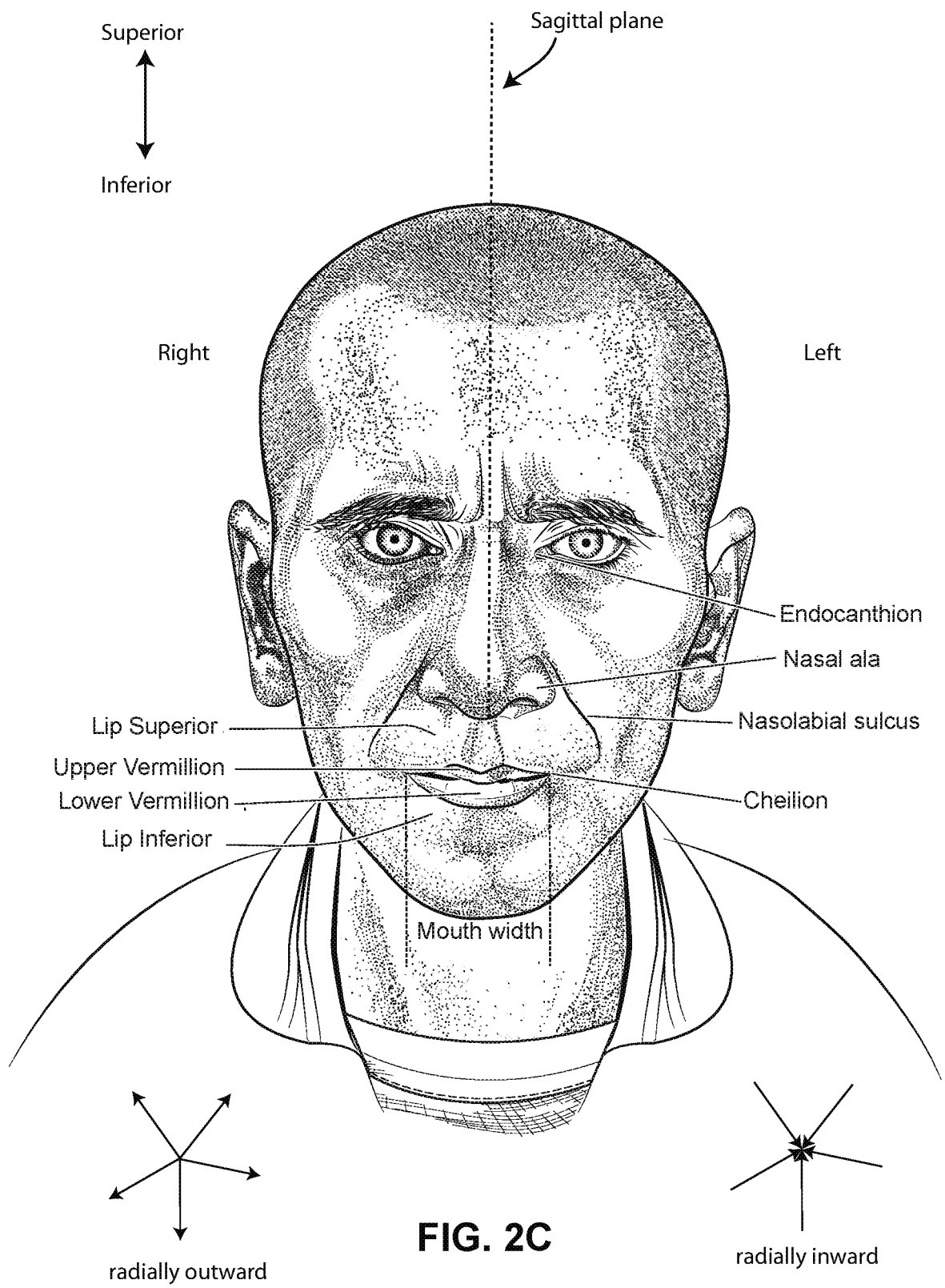
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
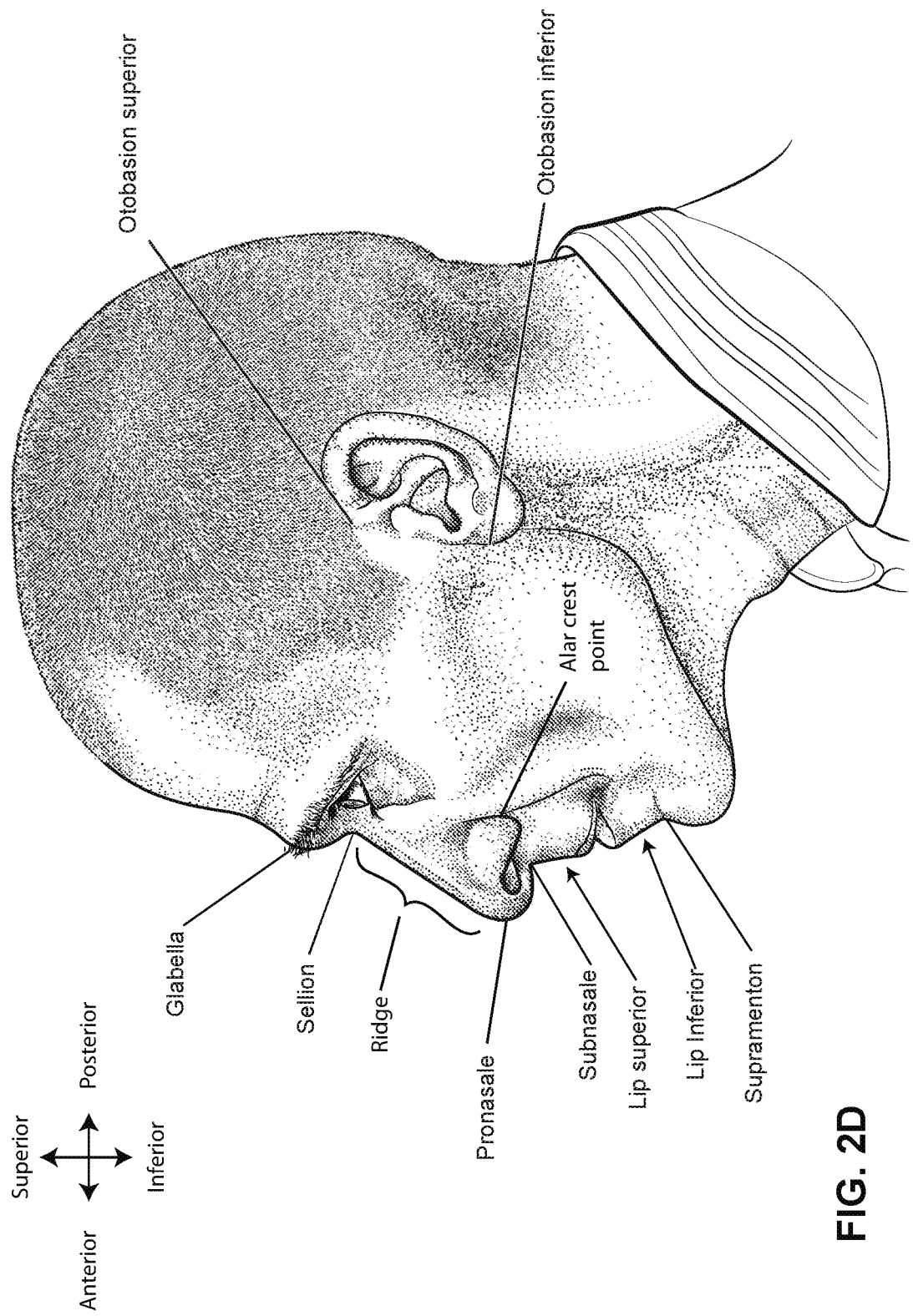
FIG. 2D is a side view of a head with several features of surface anatomy identified including *Glabella*, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
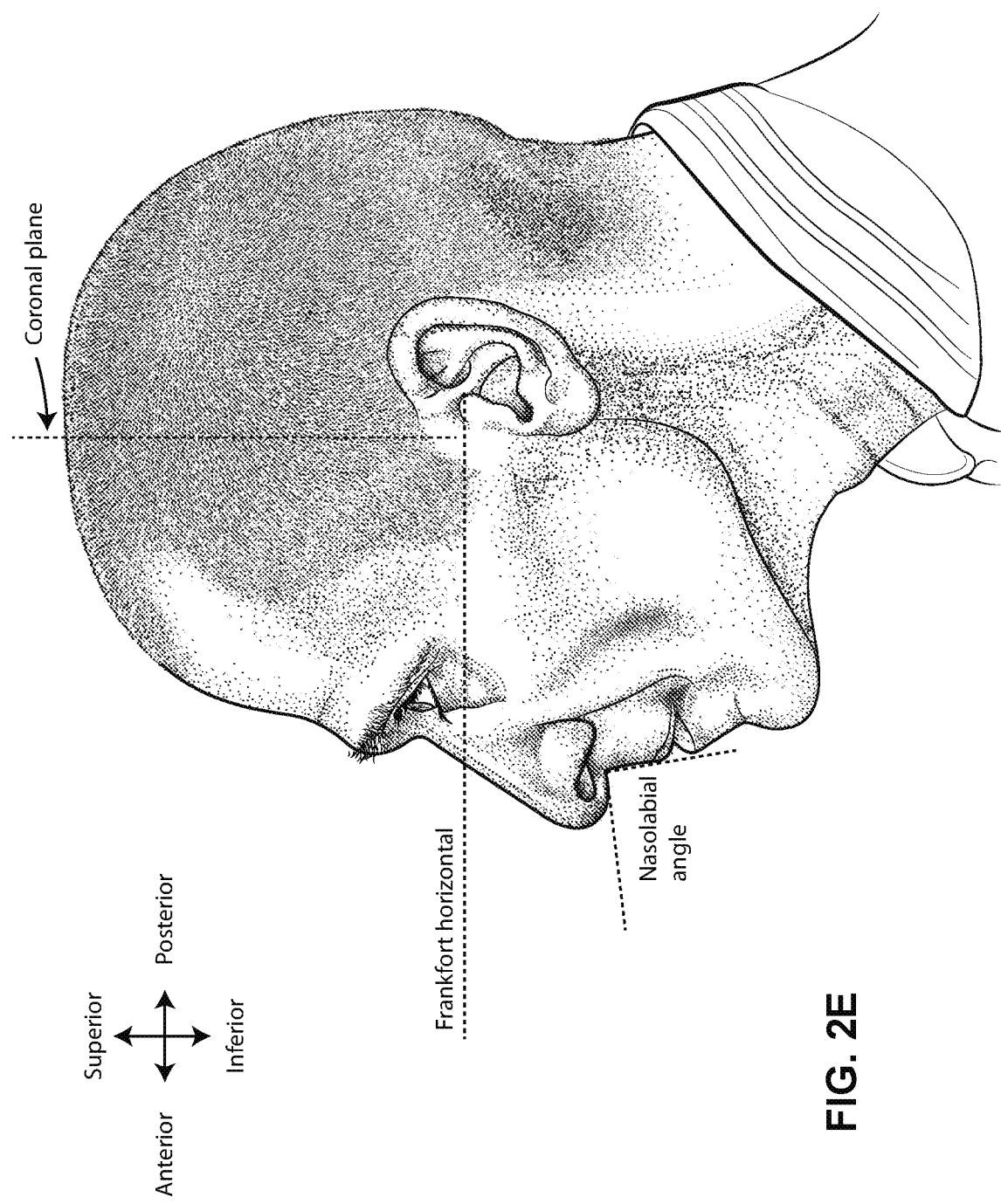

FIG. 2E is a further side view of a head. The approximate locations of the Frankfort horizontal and nasolabial angle are indicated. The coronal plane is also indicated.

Figure 2F:
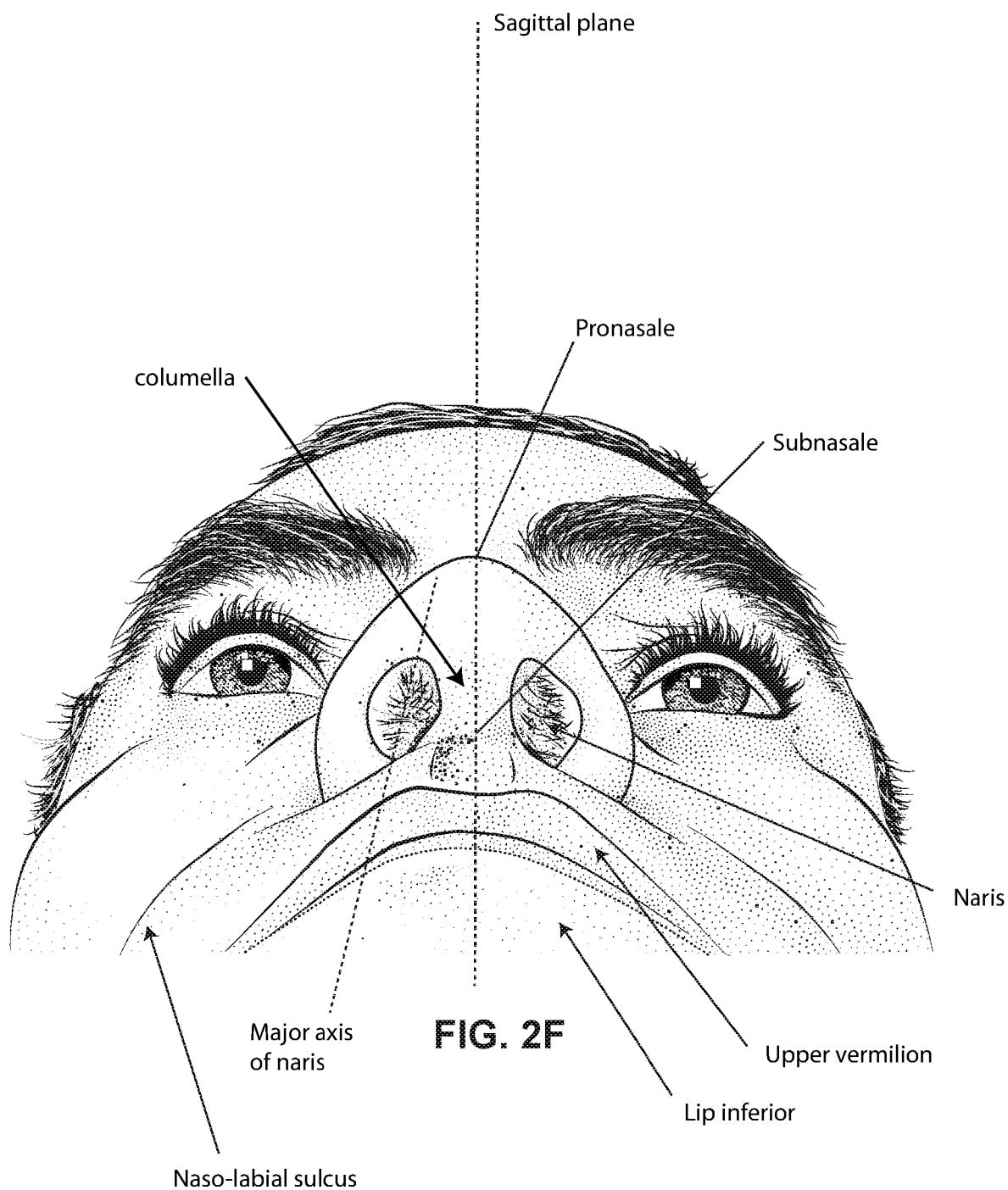

FIG. 2F shows a base view of a nose with several features identified including naso-labial sulcus, lip inferior, upper Vermilion, naris, subnasale, columella, pronasale, the major axis of a naris and the midsagittal plane.

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from the midsagittal plane, amongst other things showing the septum cartilage and medial crus of greater alar cartilage.

Figures 2J, 2K:
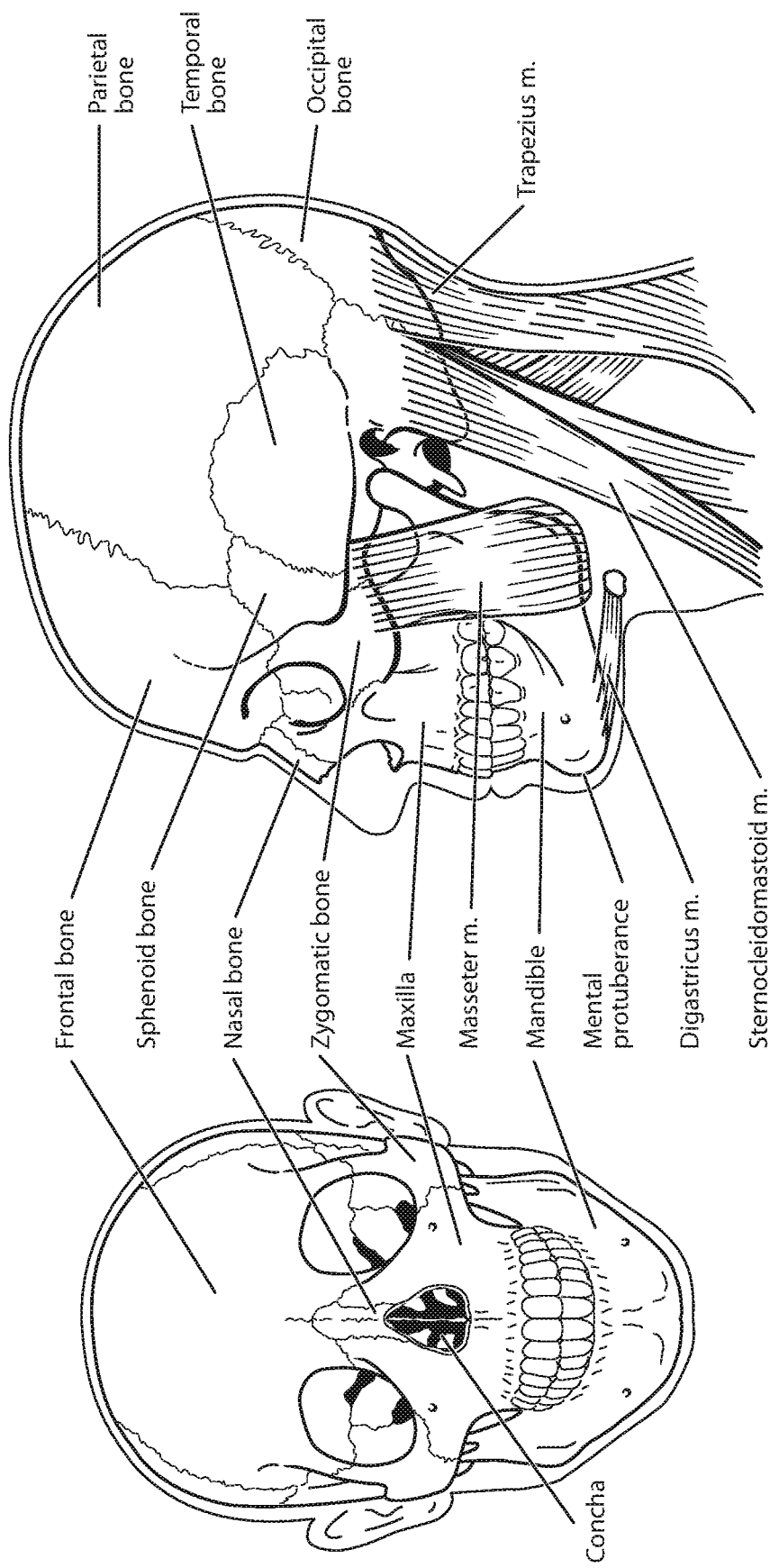

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
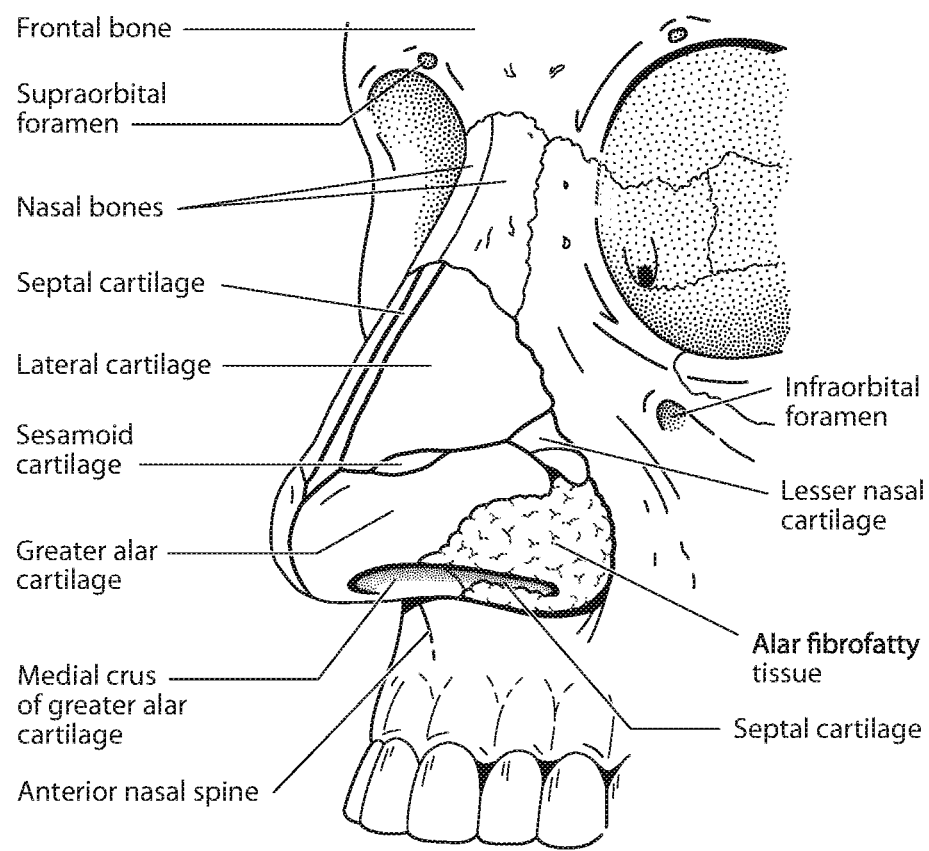

FIG. 2L shows an anterolateral view of a nose.

4.3 Patient Interface

Figure 3A:
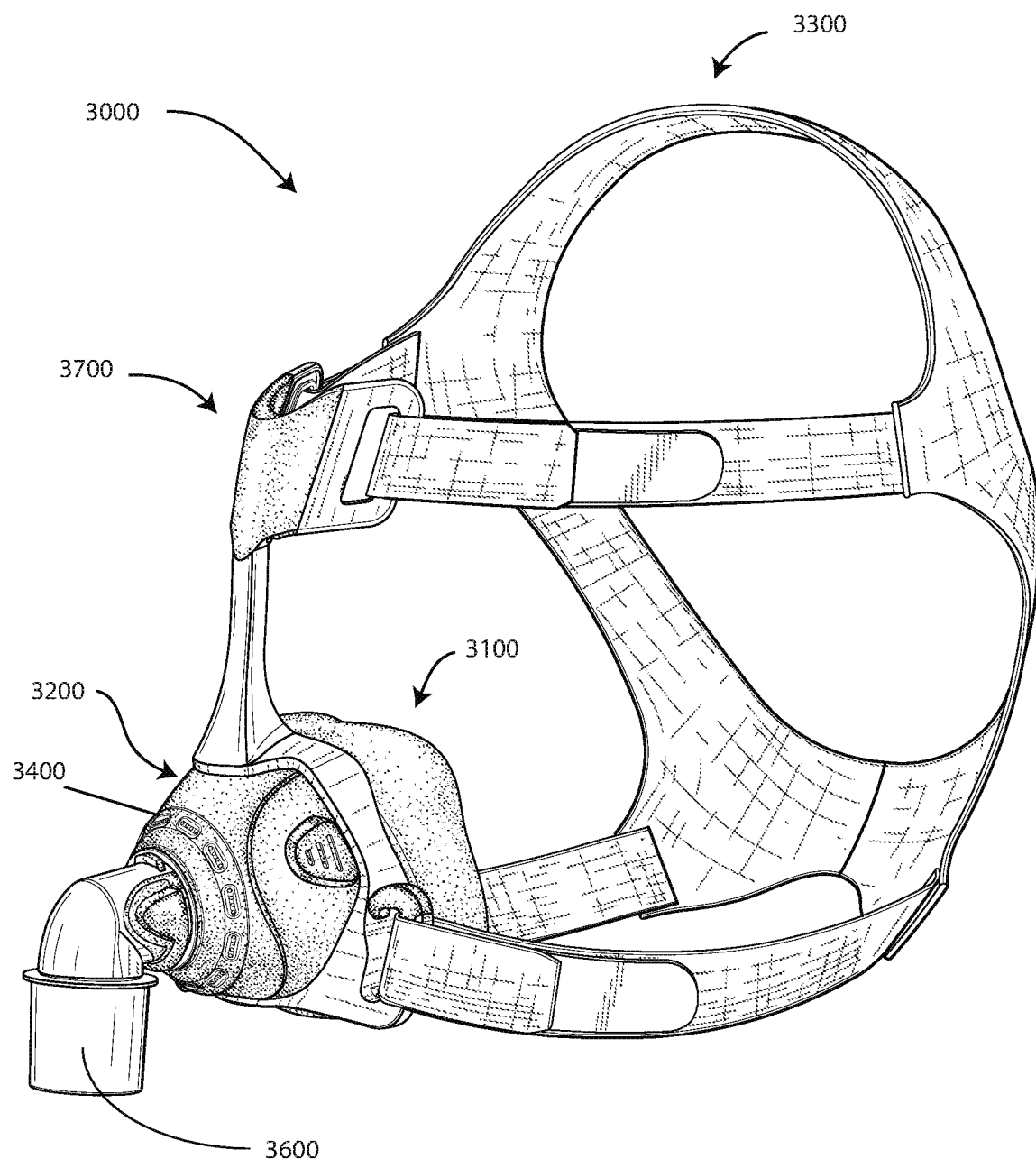

FIG. 3A shows a patient interface in the form of a nasal mask in accordance with one form of the present technology.

Figure 3B:
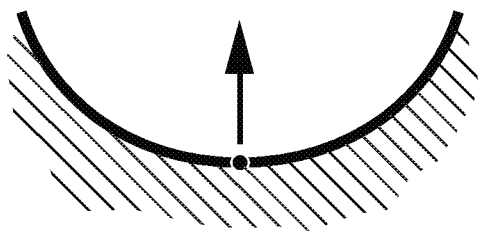

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

Figure 3C:
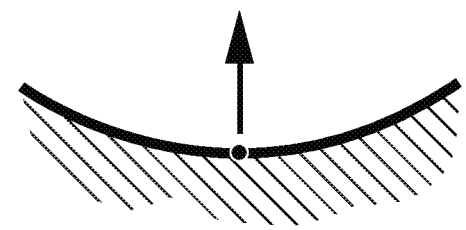

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

Figure 3D:
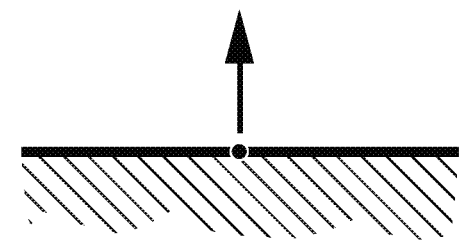

FIG. 3D shows a schematic of a cross-section through a structure at a point. An outward normal at the point is indicated. The curvature at the point has a value of zero.

Figure 3E:
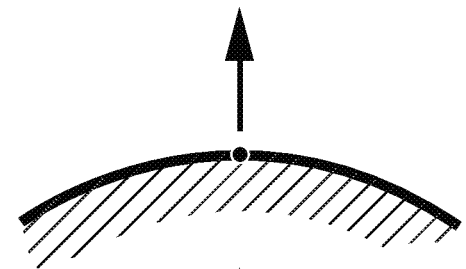

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

Figure 3F:
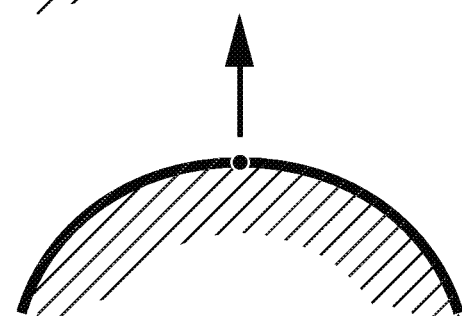

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3H:
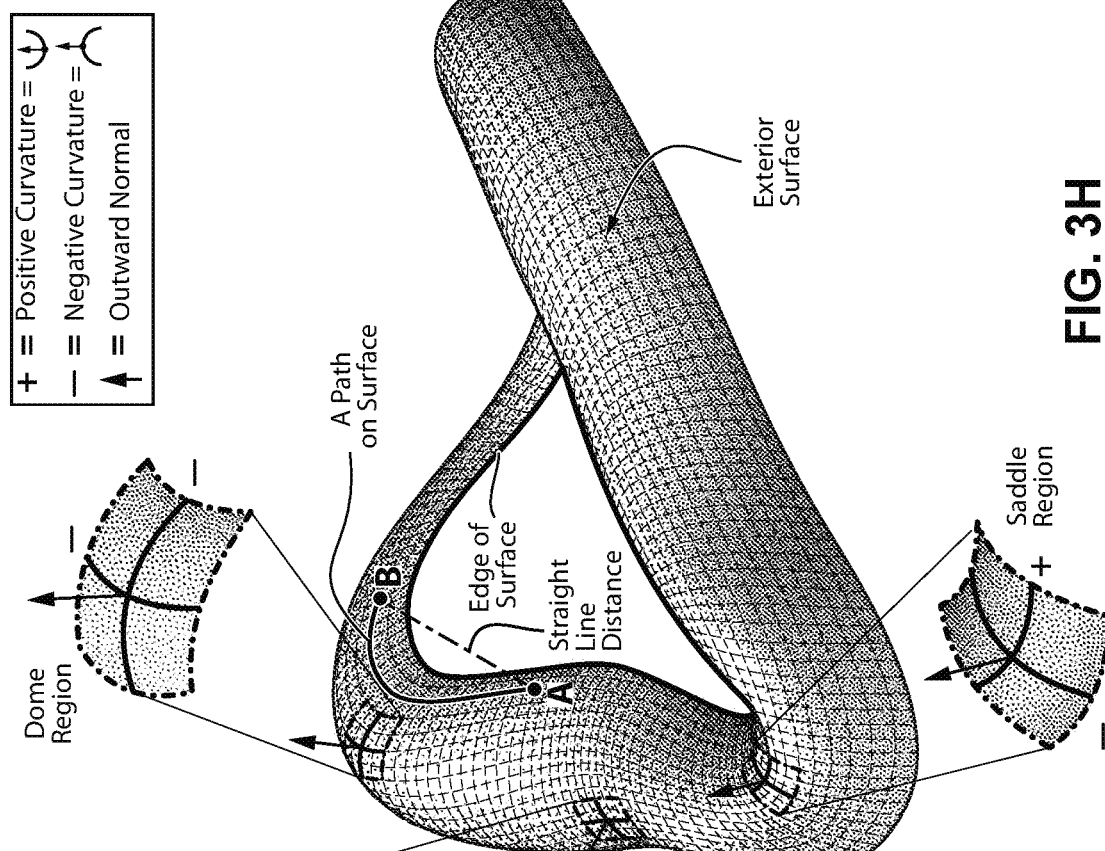
Figure 3G:
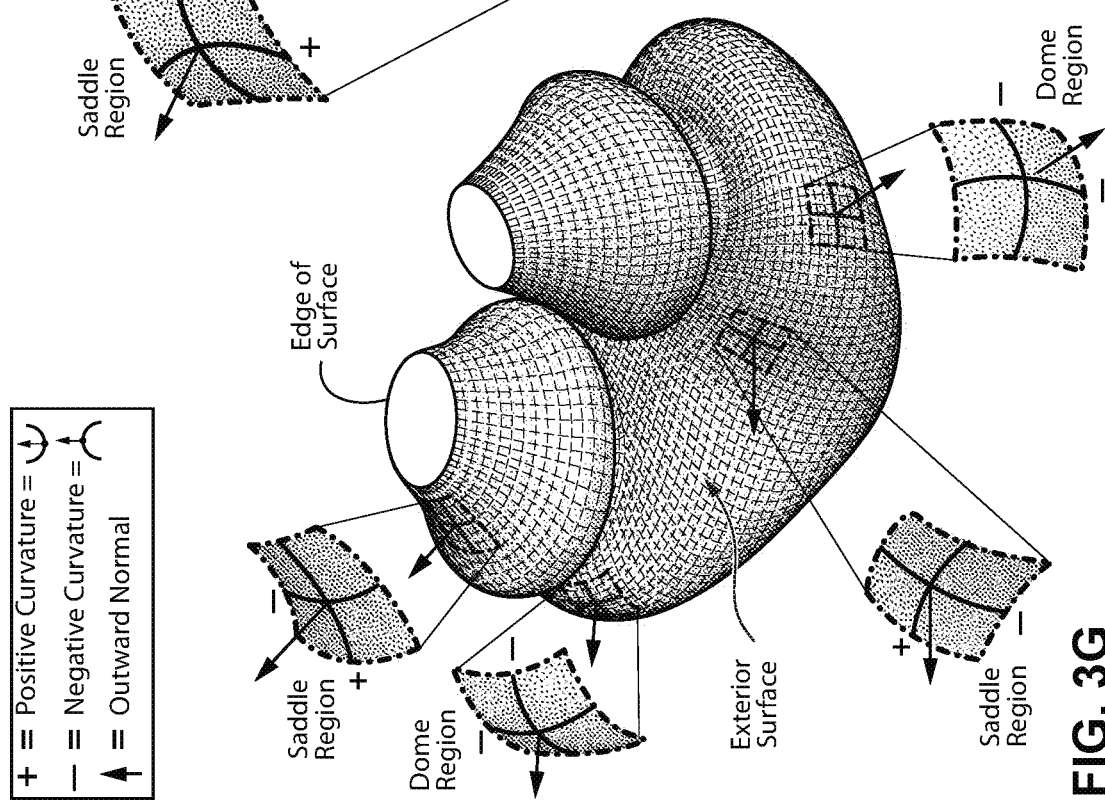

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

Figure 3I:
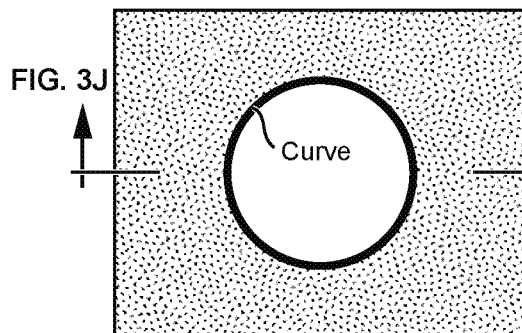

FIG. 3I shows the surface of a structure, with a one dimensional hole in the surface. The illustrated plane curve forms the boundary of a one dimensional hole.

Figure 3K:
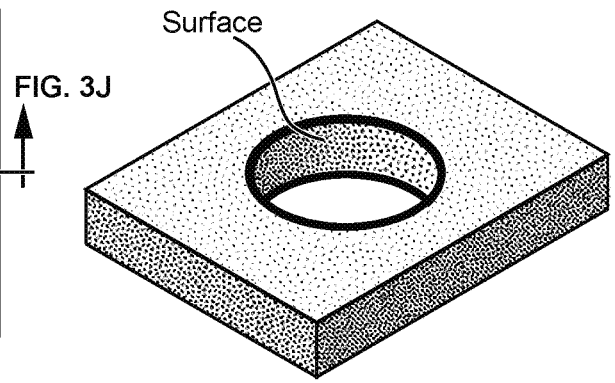
Figure 3J:
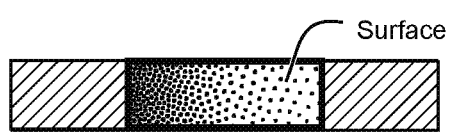

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

Figure 3L:
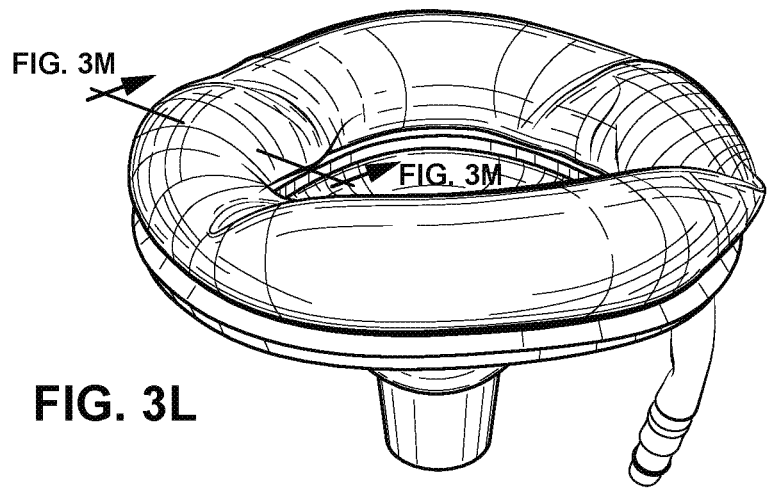

FIG. 3L shows a mask having an inflatable bladder as a cushion.

Figure 3M:
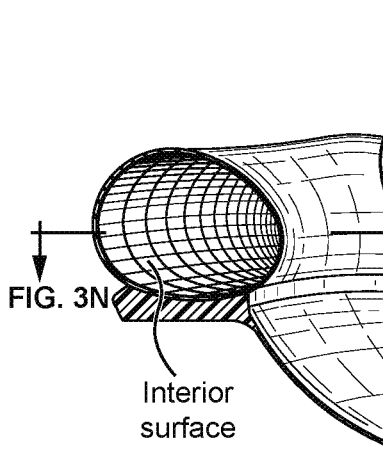

FIG. 3M shows a cross-section through the mask of FIG. 3L, and shows the interior surface of the bladder. The interior surface bounds the two dimensional hole in the mask.

Figure 3N:
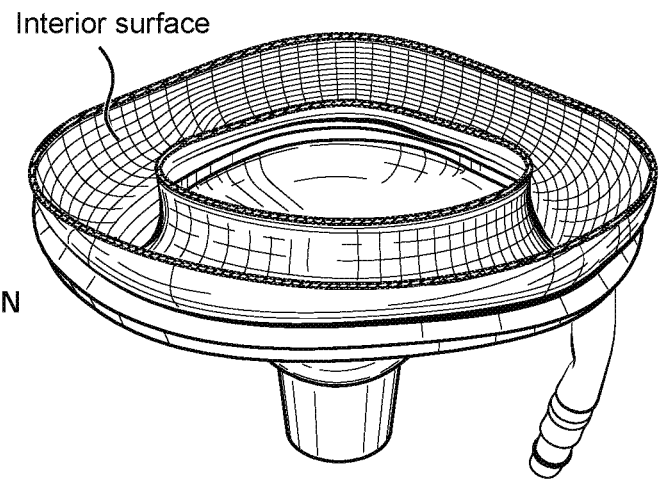

FIG. 3N shows a further cross-section through the mask of FIG. 3L. The interior surface is also indicated.

FIG. 3O illustrates a left-hand rule.

FIG. 3P illustrates a right-hand rule.

FIG. 3Q shows a left ear, including the left ear helix.

FIG. 3R shows a right ear, including the right ear helix.

FIG. 3S shows a right-hand helix.

FIG. 3T shows a view of a mask, including the sign of the torsion of the space curve defined by the edge of the sealing membrane in different regions of the mask.

Figure 3U:
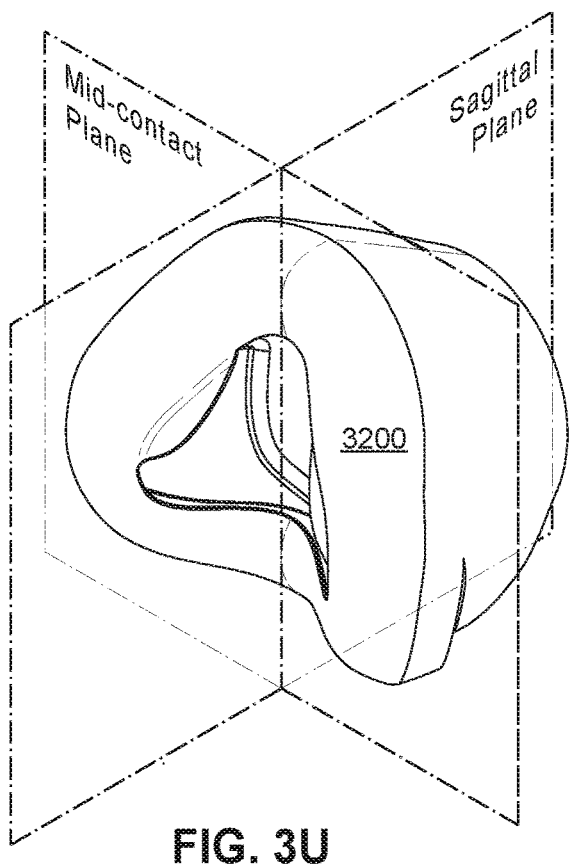

FIG. 3U shows a view of a plenum chamber 3200 showing a sagittal plane and a mid-contact plane.

Figure 3V:
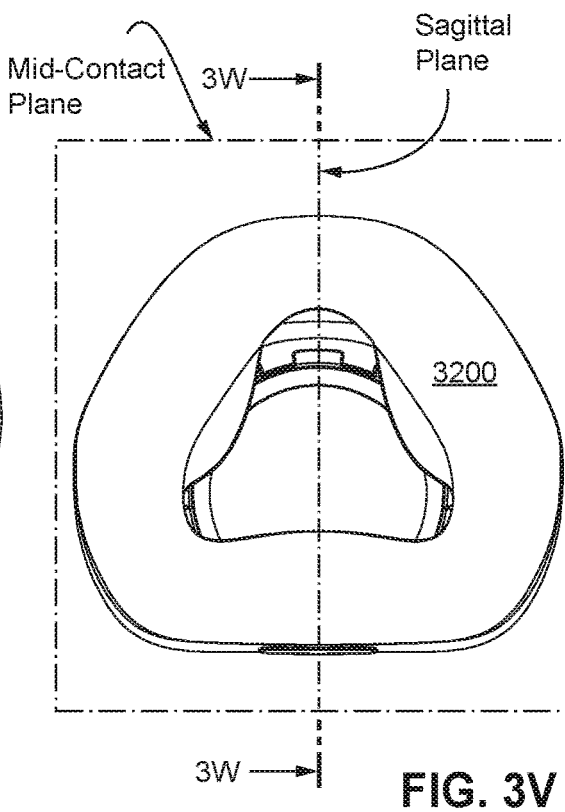

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

Figure 3W:
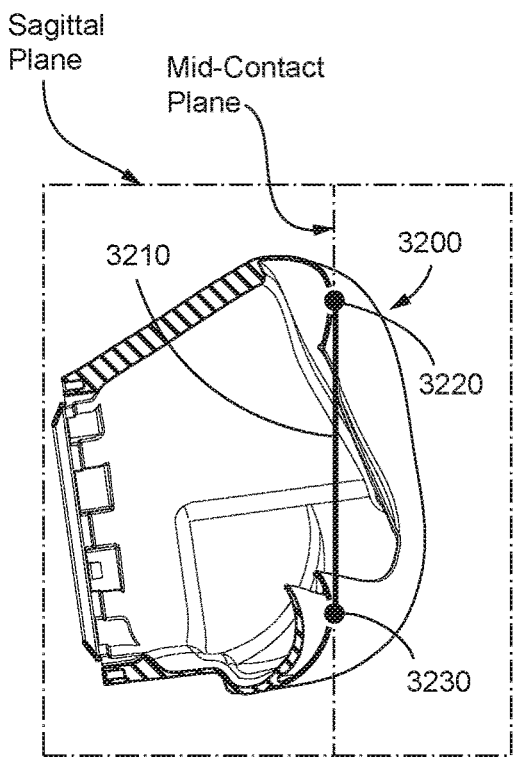

FIG. 3W shows a cross-section through the plenum chamber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord 3210 which lies on the sagittal plane and just touches the cushion of the plenum chamber at two points on the sagittal plane: a superior point 3220 and an inferior point 3230. Depending on the geometry of the cushion in this region, the mid-contact plane may be a tangent at both the superior and inferior points.

Figure 3X:
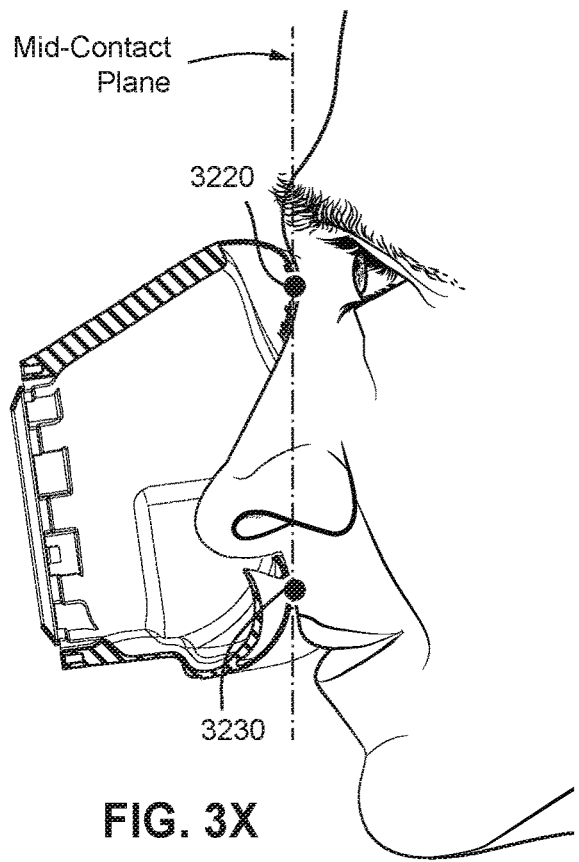

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point 3220 sits approximately on the sellion, while the inferior point 3230 sits on the lip superior.

4.4 RPT Device

Figure 4A:
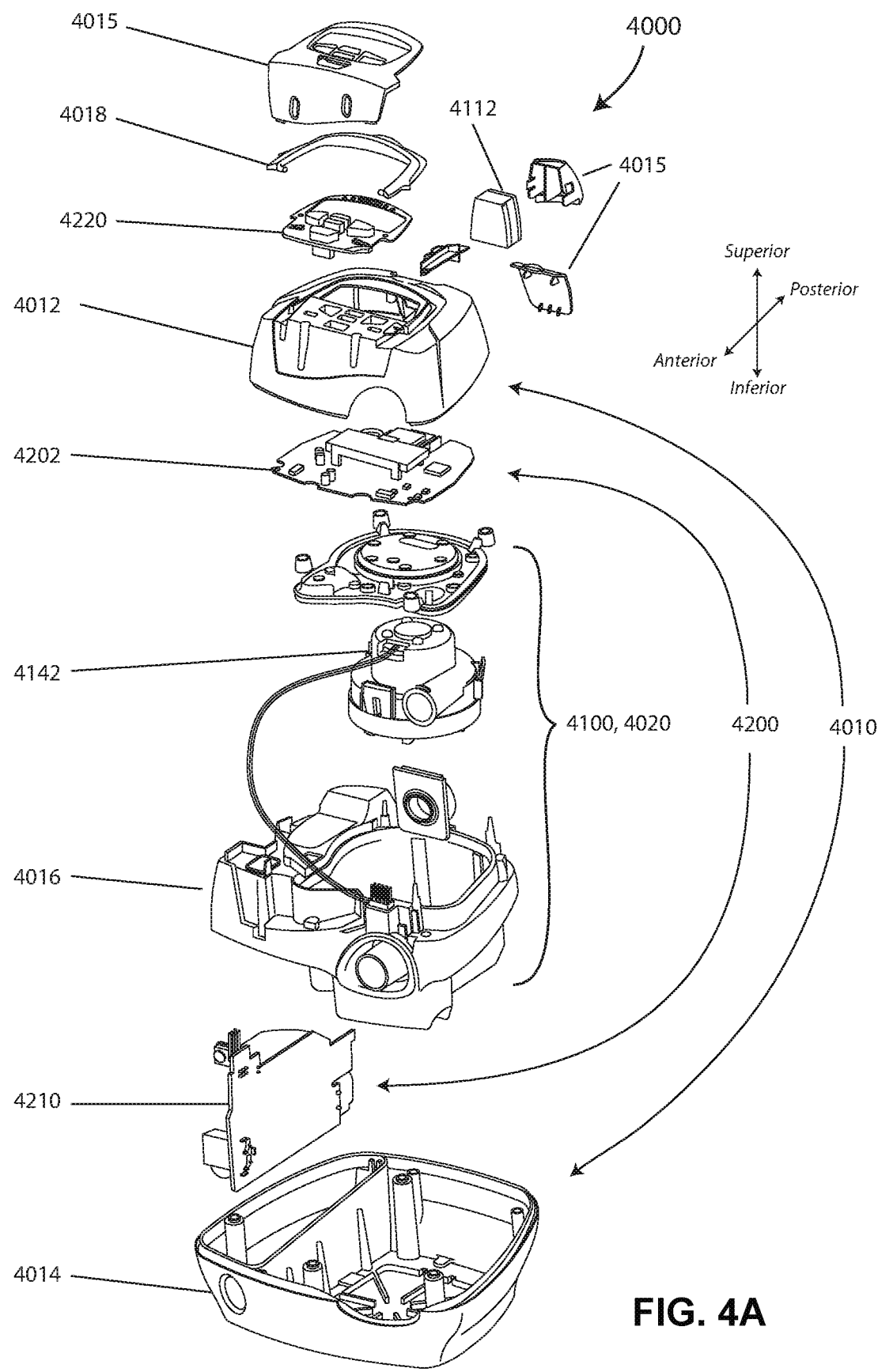

FIG. 4A shows an RPT device in accordance with one form of the present technology.

Figure 4B:
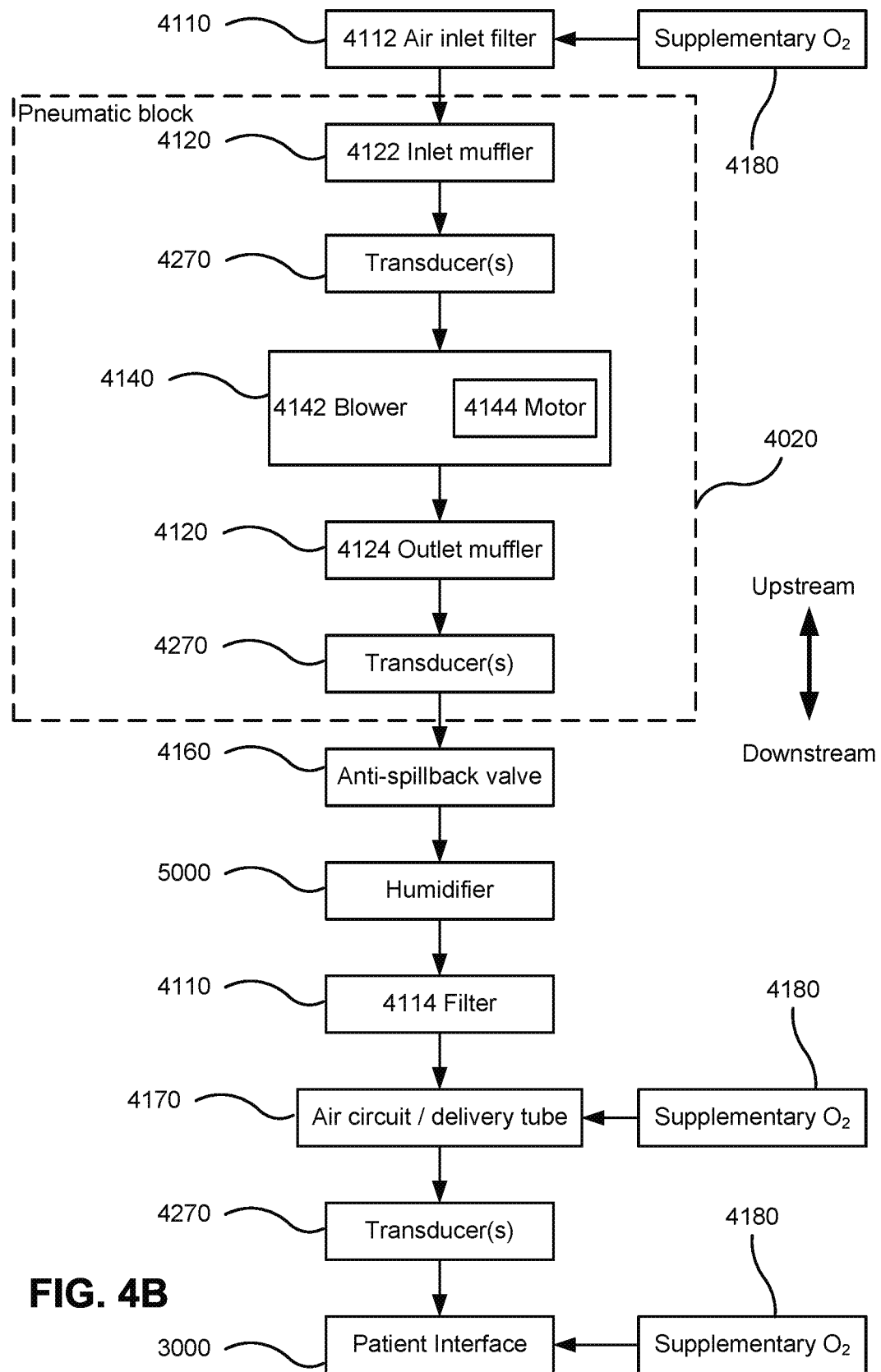

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

Figure 4C:
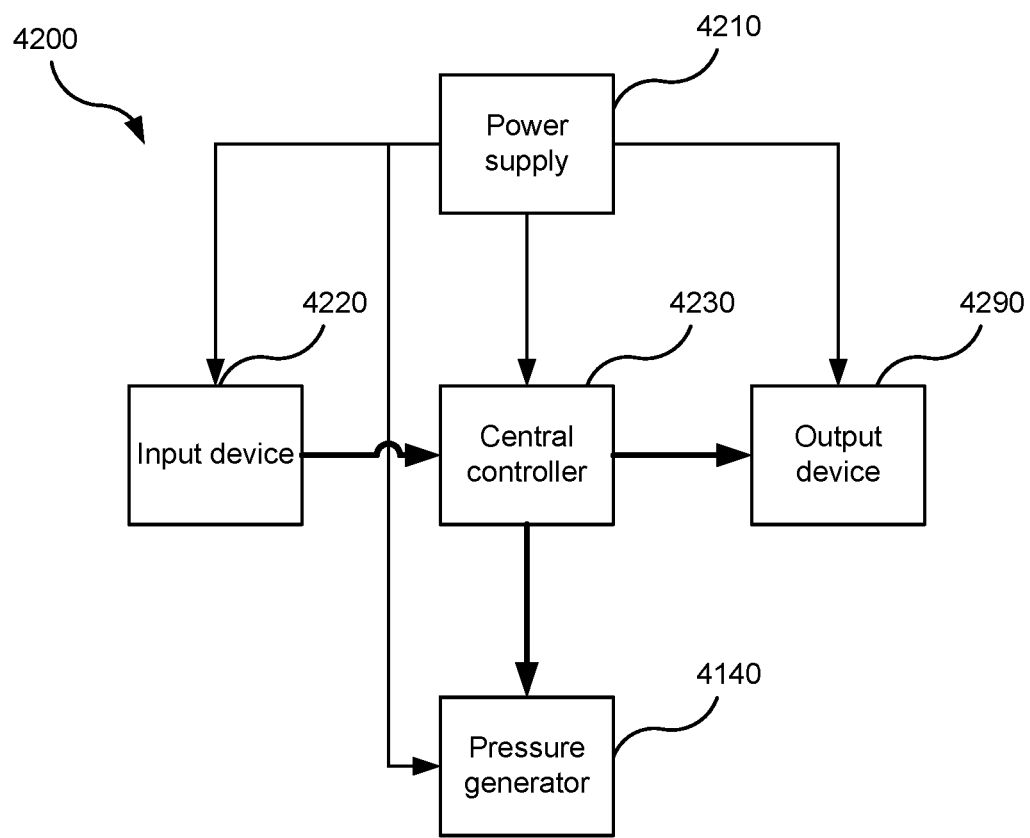

FIG. 4C is a schematic diagram of the electrical components of an RPT device in accordance with one form of the present technology.

4.5 Humidifier

Figure 5A:
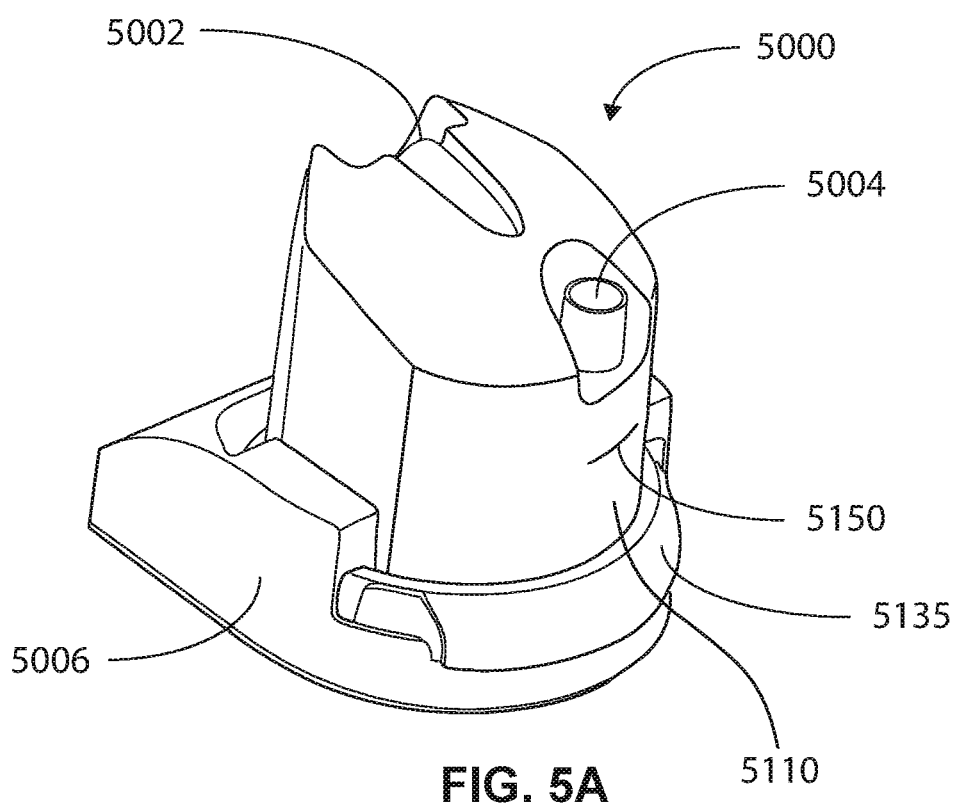

FIG. 5A shows an isometric view of a humidifier in accordance with one form of the present technology.

Figure 5B:
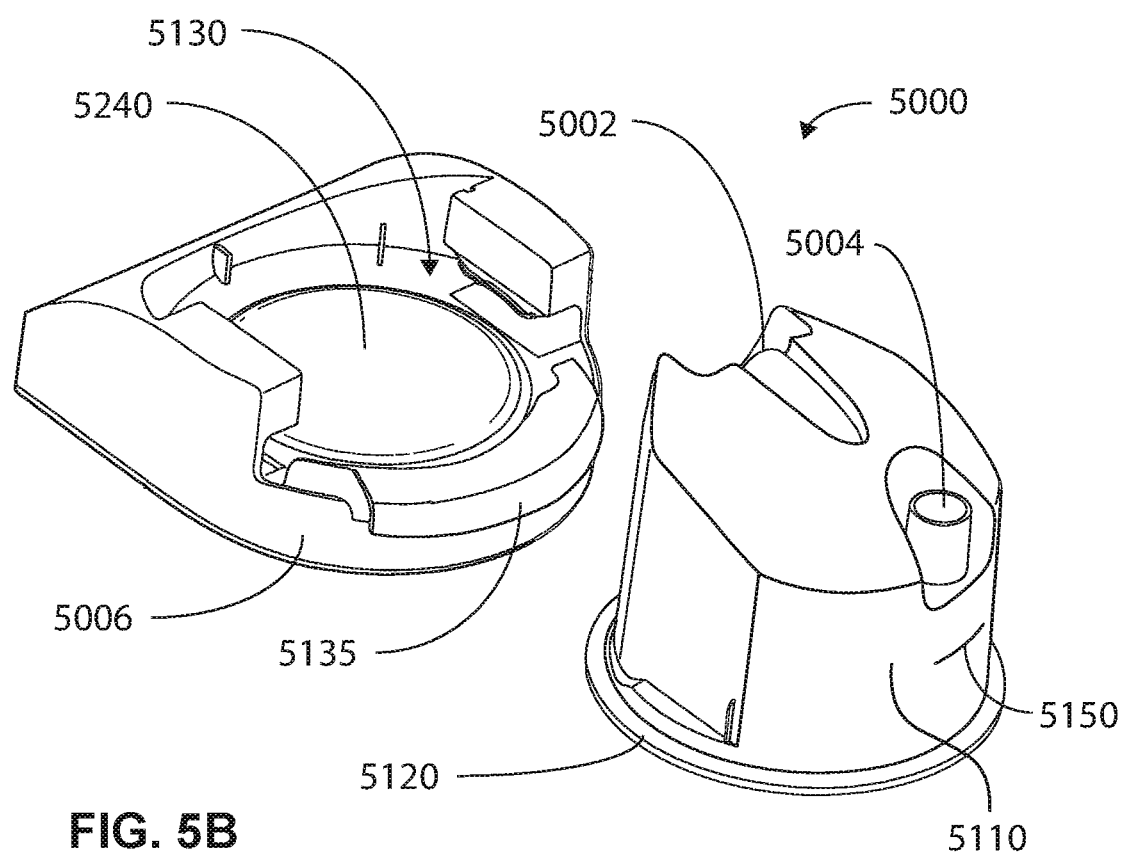

FIG. 5B shows an isometric view of a humidifier in accordance with one form of the present technology, showing a humidifier reservoir 5110 removed from the humidifier reservoir dock 5130.

4.6 Air Circuit

Figure 6:
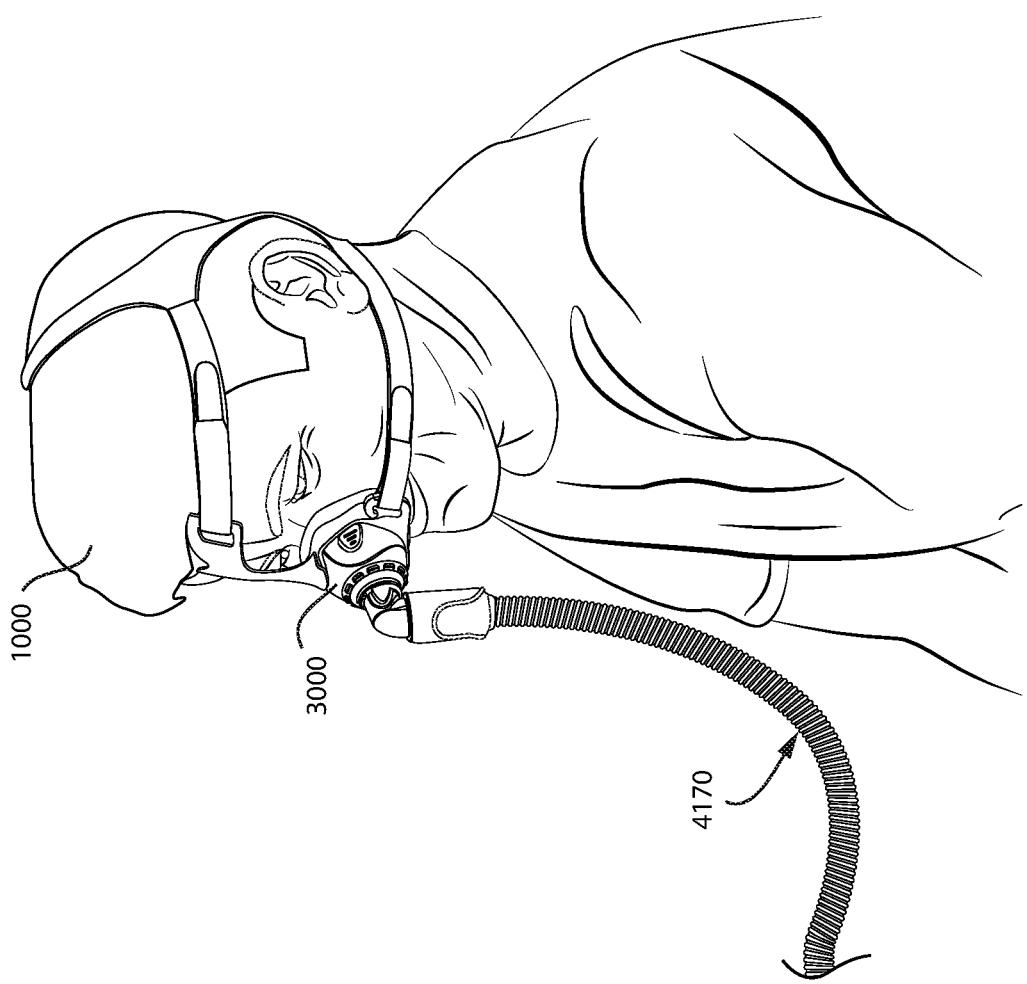

FIG. 6 shows an air circuit in connection with a patient interface in accordance with one form of the present technology.

Figure 7:

FIG. 7 shows a kinked air circuit during use of a therapy device.

Figure 8:

FIG. 8 shows an air circuit during use of a therapy device by a patient in accordance with one form of the present technology.

Figure 9:

FIG. 9 shows a patient using a therapy device that includes an air circuit and a patient interface in accordance with one form of the present technology.

Figure 10:
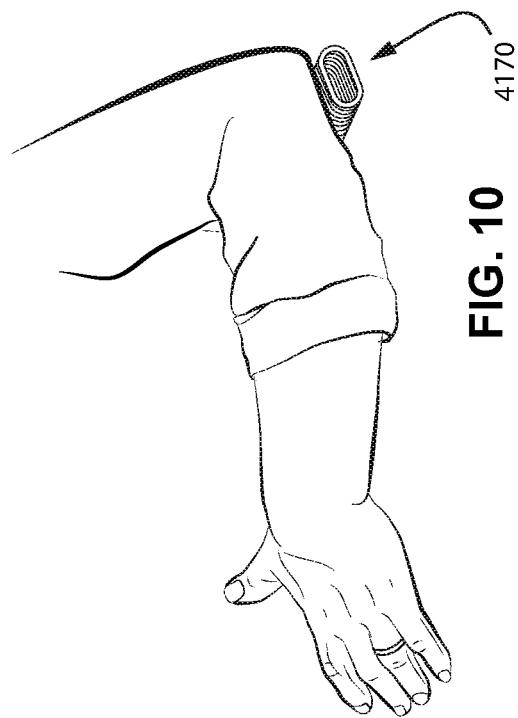

FIG. 10 shows an enlarged view of an air circuit deflecting when subjected to force from a patient.

Figure 11:
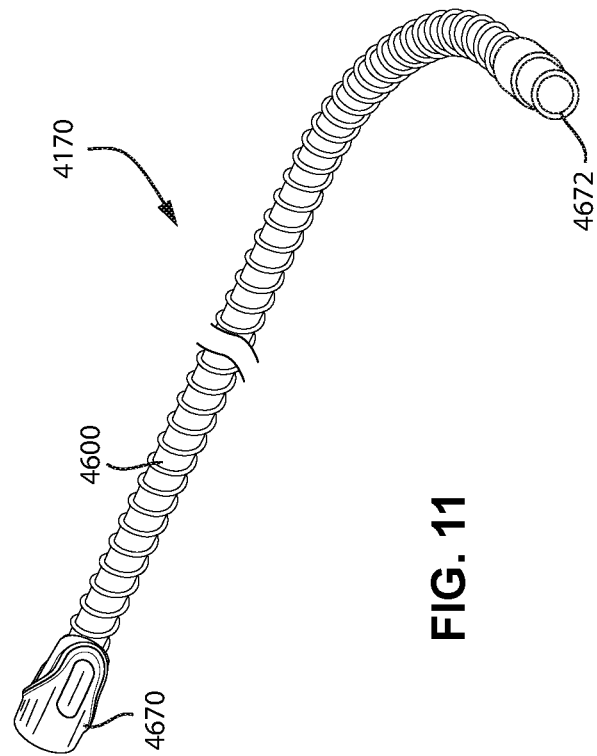

FIG. 11 shows one form of an air circuit in accordance with one form of the present technology.

Figure 12:
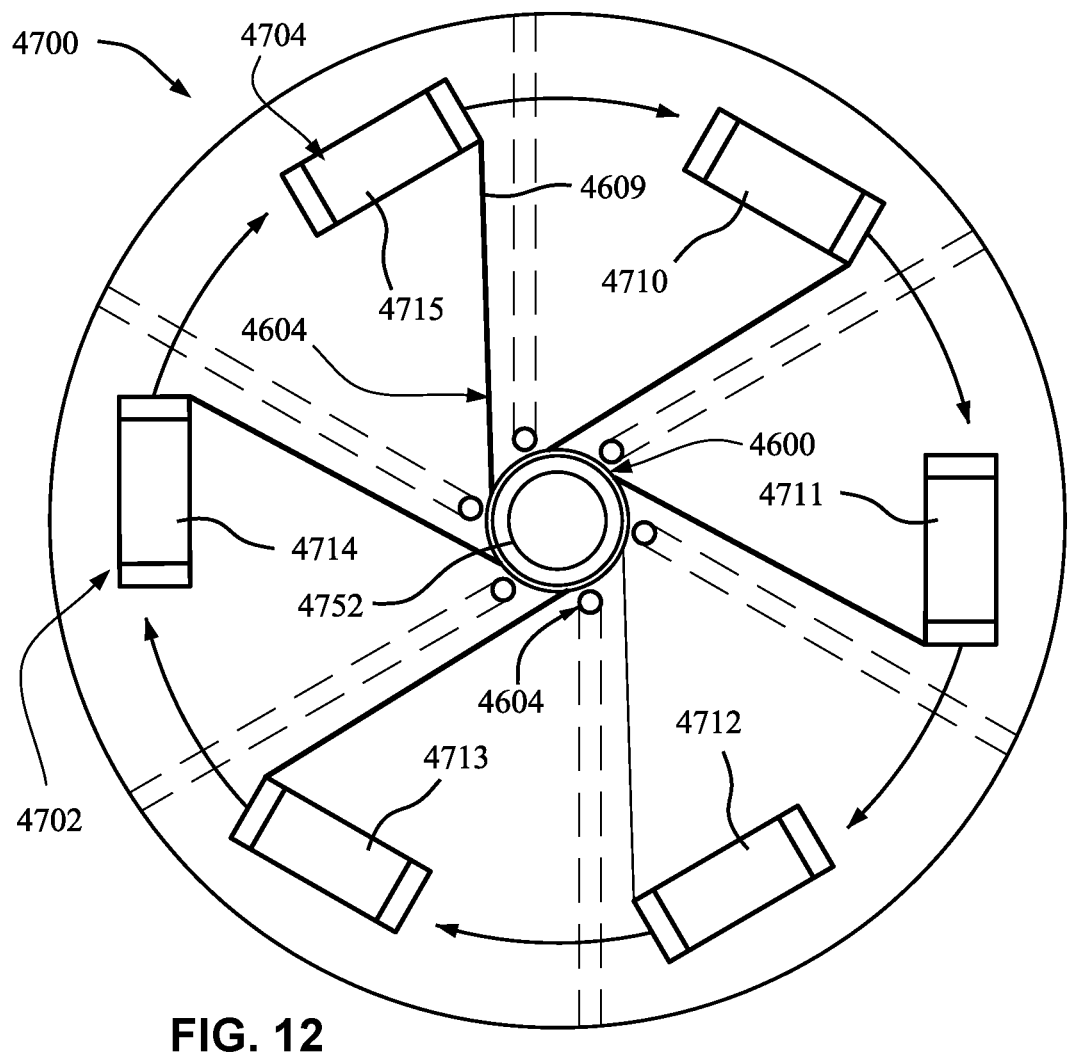

FIG. 12 shows a top view of a weaving machine in accordance with one form of the present technology.

Figure 13:
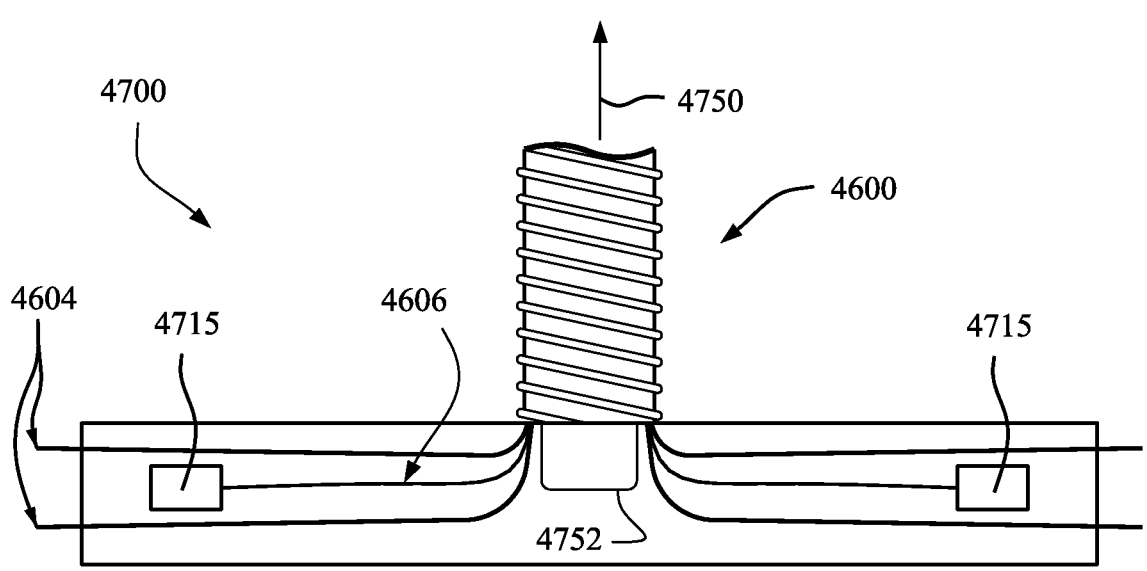

FIG. 13 shows a side view of a weaving machine in accordance with one form of the present technology.

Figure 14:
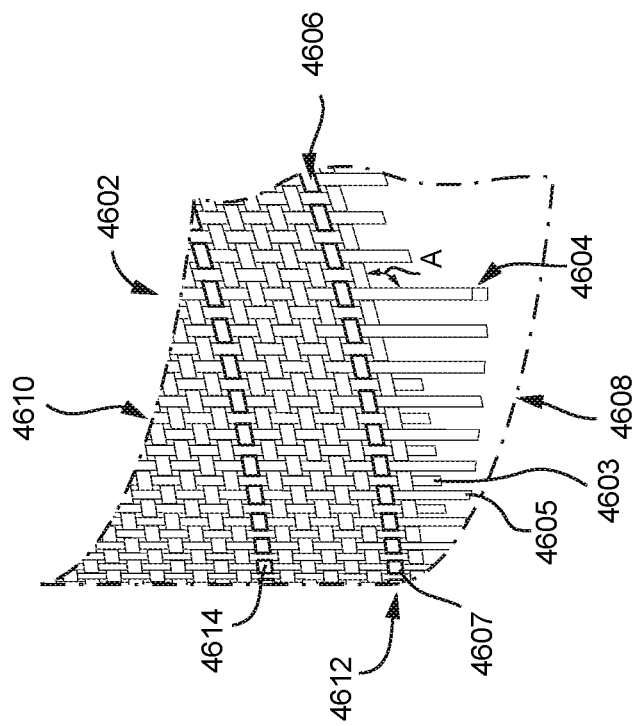

FIG. 14 shows a woven structure in accordance with one form of the present technology.

Figure 15:
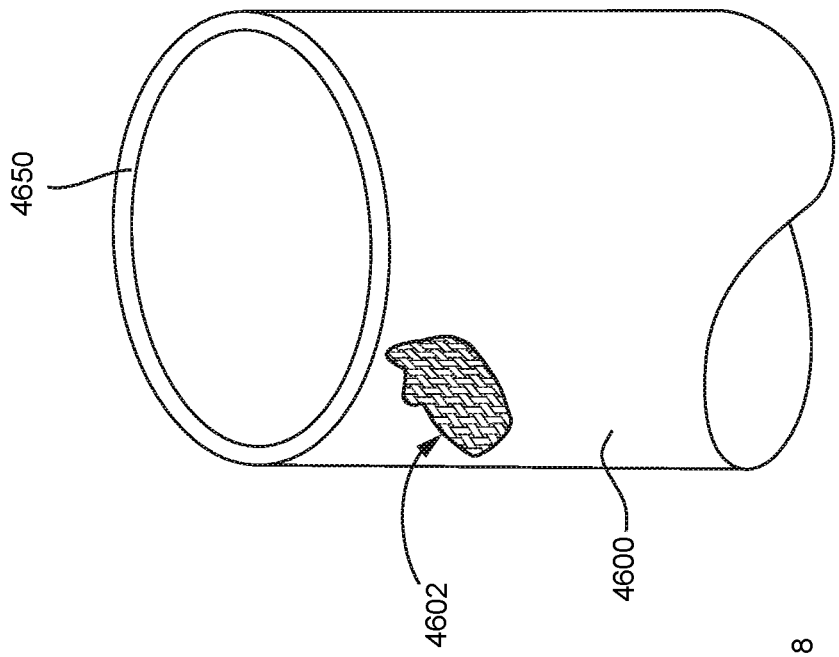

FIG. 15 shows a portion of a tubular structure in accordance with one form of the present technology.

Figure 16:
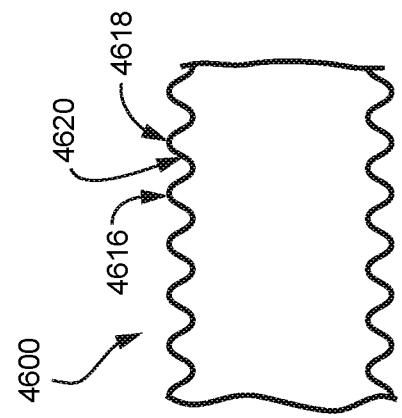

FIG. 16 shows a portion of a tubular structure in accordance with one form of the present technology.

FIG. 17 shows a portion of a tubular structure in a bent position in accordance with one form of the present technology.

FIG. 17A shows an enlarged portion of a tubular structure.

FIG. 18 shows a portion of a tubular structure subjected to a tension force in accordance with one form of the present technology.

FIG. 19 shows a schematic of a portion of a configuration of a tubular structure in accordance with one form of the present technology.

FIG. 20 shows a portion of another configuration of a tubular structure in accordance with one form of the present technology.

FIG. 21 shows a schematic of a portion of another configuration of a tubular structure in accordance with one form of the present technology.

FIG. 22 shows a schematic of a portion of another configuration of a tubular structure in accordance with one form of the present technology.

FIG. 23 shows a schematic of a portion of another configuration of a tubular structure in accordance with one form of the present technology.

FIG. 24 shows a schematic of a portion of another configuration of a tubular structure in accordance with one form of the present technology.

FIG. 25 shows a chart with various thread compositions.

FIG. 26 shows a chart with various shuttle arrangements for tubular structures with different thread constructions.

FIG. 27 shows a tubular structure formed with one quantity of warp threads in accordance with one form of the present technology.

FIG. 28 shows a tubular structure formed with a second quantity of warp threads in accordance with one form of the present technology.

FIG. 29 shows a tubular structure formed with a third quantity of warp threads in accordance with one form of the present technology.

FIG. 30 shows a schematic view of a portion of a tubular structure with a first weft density in accordance with one form of the present technology.

FIG. 31 shows a schematic view of a portion of a tubular structure with a second weft density in accordance with one form of the present technology.

FIG. 32 shows a schematic view of a portion of a tubular structure with a third weft density in accordance with one form of the present technology.

Figure 33:
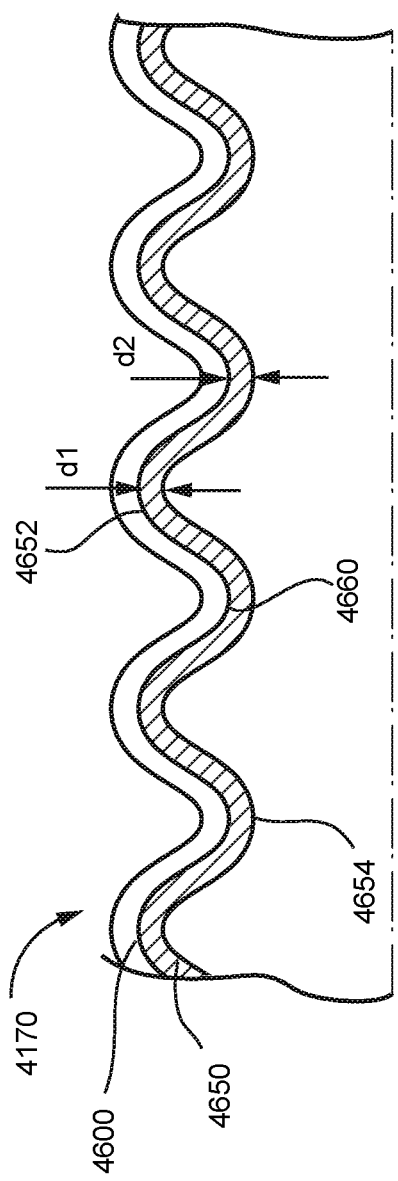

FIG. 33 shows a schematic view of a portion of a tubular structure and sealing structure in accordance with one form of the present technology.

Figure 34:
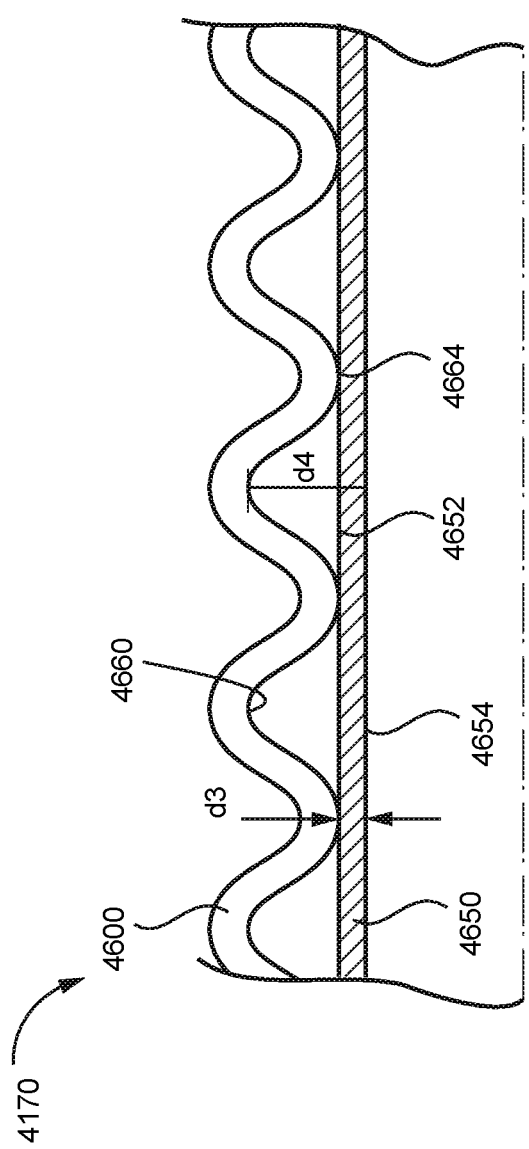

FIG. 34 shows a schematic view of a portion of a tubular structure and sealing structure in accordance with one form of the present technology.

FIG. 35 shows a selection matrix with various thread and shuttle configurations.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

5.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 $cmH_2O$ with respect to ambient.

The patient interface 3000 in accordance with one form of the present technology is constructed and arranged to be able to provide a supply of air at a positive pressure of at least 10 $cmH_2O$ with respect to ambient.

The patient interface 3000 in accordance with one form of the present technology is constructed and arranged to be able to provide a supply of air at a positive pressure of at least 20 $cmH_2O$ with respect to ambient.

5.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

5.3.1.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

5.3.2 Positioning and Stabilising Structure

The seal-forming structure 3100 of the patient interface 3000 of the present technology may be held in sealing position in use by the positioning and stabilising structure 3300.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

5.3.3 Vent

In one form, the patient interface 3000 includes a vent 3400 constructed and arranged to allow for the washout of exhaled gases, e.g. carbon dioxide.

5.3.4 Decoupling Structure(s)

In one form the patient interface 3000 includes at least one decoupling structure, for example, a swivel or a ball and socket.

5.3.5 Connection Port

Connection port 3600 allows for connection to the air circuit 4170.

5.4 RPT Device

An RPT device 4000 in accordance with one aspect of the present technology comprises mechanical, pneumatic, and/or electrical components and is configured to execute one or more algorithms, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 $cmH_2O$, or at least 10$cmH_2O$, or at least 20 $cmH_2O$.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors and flow rate sensors.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller, a therapy device controller, a pressure generator 4140, one or more protection circuits, memory, transducers 4270, data communication interface and one or more output devices. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

5.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers housed in a blower housing, such as in a volute. The blower may be capable of delivering a supply of air, for example at a rate of up to about 120 litres/minute, at a positive pressure in a range from about 4 cmH$_2$O to about 20 cmH$_2$O, or in other forms up to about 30 cmH$_2$O. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller.

In other forms, a pressure generator 4140 may be a piston-driven pump, a pressure regulator connected to a high pressure source (e.g. compressed air reservoir), or a bellows.

5.4.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

5.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.5 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference. As shown in FIG. 6, patent interface 3000 is attached to or coupled with air circuit 4170.

During use of a therapy device the air circuit 4170 may cause discomfort to the user. For example the air circuit 4170 may drag or pull along the patient interface and/or RPT device 4000. The weight and/or flexibility or rigidity of air circuit 4170 may influence how much the RPT device 4000 and/or patient interface 3000 is influenced by air circuit 4170. For example, if air circuit 4170 is attached to the patient interface 3000 and to the RPT device 4000 and air circuit 4170 is a rigid device, movement by the patient wearing patient interface 3000 may transfer force through the air circuit 4170 thereby causing RPT device 4000 to move and/or causing the patient interface 3000 to move. If the air circuit 4170 is more flexible, movement by the patient may cause air circuit 4170 to flex or expand such that the air circuit 4170 absorbs tension and the force directed to the RPT device and/or the patient interface is reduced when compared to a more rigid air circuit 4170.

Additionally, the weight of the air circuit 4170 may cause discomfort to the patient and may also impact the drag associated with air circuit 4170. When moving about, weight of the air circuit 4170 may interfere with the natural movement of the patient such that it causes the patient discomfort.

Further, an air circuit 4170 with greater weight will also influence patient interface 3000 and RPT device 4000 if moved compared with a lighter air circuit 4170. A lighter air circuit 4170 may improve comfort and may therefore increase the likelihood that the patient continues to receive therapy. By forming a light air circuit 4170 the patient may not feel the weight of air circuit 4170 thus allowing the patient to move freely.

In addition, when a patient moves about air circuit 4170 may twist and bend. In some forms, an air circuit 4170 may be kinked such that air is not permitted to travel through, or the flow of air through air circuit 4170 is reduced as depicted in FIG. 7. When air circuit 4170 is kinked and stops or reduces airflow to the patient the patient may not receive adequate air for therapy and may wake up. A patient that wakes up due to a kinking may discontinue use of the therapy device. Therefore, an air circuit 4170 that is resistant to kinking may increase the likelihood that the patient will continue to receive therapy.

As shown in FIG. 8, patients may be arranged in different positions during use of a therapy device. An air circuit 4170 that is able to bend and turn to accommodate such movements may be more comfortable to a patient that other forms of an air circuit. Additionally, an air circuit that is able to bend and twist may perform better compared to other air circuits that may kink when bent or twisted.

While receiving therapy, a patient may move about, for example, during sleep. In some instances the patient may rest upon air circuit 4170. For example, as shown in FIG. 9, patient 1000 may wrap air circuit 4170 under his or her arm causing a force to be exerted downward or perpendicular to air circuit 4170. Such a force may cause air circuit 4170 to occlude or reduce in cross-sectional area either stopping or reducing the airflow to patient interface 3000. A stoppage or reduction in air flow may cause the patient to wake up during use of the therapy device. A patient may stop using the device if the patient continues to wake up while using the therapy device. Forming air circuit 4170 such that air circuit 4170 resists occlusion such as depicted in FIG. 10, may permit air to continue to flow to the patient interface 3000 so that the patient is able to continue to receive adequate therapy. As shown in FIG. 10, air circuit 4170 may be configured to deflect to accommodate the arm of the patient. In the configuration shown in FIG. 10 air circuit 4170 is not a rigid structure, but air circuit 4170 has sufficient rigidity to resist a collapse of air circuit 4170 so as to continue to provide pressurized air to the patient. Such a configuration may increase the likelihood that the patient continues to use the therapy device.

A patient may also stop the use of a therapy device if the materials from which various components of air circuit 4170 are formed are uncomfortable to the patient. For example, abrasive materials that can rub against the skin of a patient may cause the patient to discontinue use of the device. A soft material such as cotton, or wicking material such as polyester, may be comfortable to the touch of a patient so that the patient may be more likely to continue use of a therapy device that utilizes a comfortable material.

A particular arrangement of the material such as in a woven, non-woven, braided, knit or other network of fibers may also increase comfort while maintaining the integrity of the air circuit 4170 to encourage patients to continue use of the therapy device.

In addition to providing comfort to the patient, the air circuit 4170 may also be configured to be air tight. By forming air circuit 4170 as an air tight tube, air may be consistently and accurately delivered to the patient to receive therapy. The air circuit 4170 may be formed utilizing a woven structure that is formed in a tubular manner to form a tubular structure. In some forms the tubular structure may be coated with silicone or acrylate or other sealing member such as a biocompatible material. In other forms, a silicone tube or other air-tight tube may be over-woven with a woven tubular structure. In still further forms, a woven tubular structure may be placed over a silicone or other air-tight tube like a sock. The tubular structure may be secured in place so that the tubular structure and the air-tight tube are formed as a single unitary piece.

In addition to providing an air-tight tube, the silicone or other sealing member may assist in managing humidity and condensate within air circuit 4170. By including a sealing layer, any condensation may be prevented from seeping through the tubular structure. A patient may discontinue use of a therapy device if the air circuit 4170 is damp or wet. Therefore a sealing member may assist in maintaining consistent use by patients by providing a dry outer surface of air circuit 4170.

In some forms, air circuit 4170 may include additional features to attach to RPT device 4000 as well as patient interface 3000. As depicted in FIG. 11 air circuit 4170 is shown in isolation from RPT device 4000 and patient interface 3000. As shown, air circuit 4170 includes tubular structure 4600 as well as connector 4670 and connector 4672. In some forms, connector 4670 may be configured to connect to RPT device 4000 and connector 4672 is configured to connect to patient interface 3000 such that air is permitted to flow from RPT device 4000 to patient interface 3000. In some forms the connectors are permanently attached to tubular structure 4600. In other forms, however, the connectors may be removable from tubular structure 4600 for cleaning purposes, for example. The connection between air circuit 4170 and other components of an air therapy device can be changed or altered depending on the design of the device. For example, pressure fit connections, clip connections or other connections may be utilized.

Tubular structure 4600 may be formed of a woven, braided, knit or non-woven structure. Additionally, tubular structure 4600 may include provisions for forming an airtight tube to transfer pressurized air from RPT device 4000 to patient interface 3000.

5.5.1 Weaving Machine

In some forms of the present technology, various machines may be utilized to form a tubular structure for use with air circuit 4170. Such machines may include, a circular braiding machine, a circular knitting machine, as well as a circular weaving machine. Additionally, although discussed as forming a continuous tubular structure, machines that form flat textiles or other materials form a web of interlocking fibers may be utilized. For example, a flat knitting or weaving machine may be utilized. This flat material may be rolled and sewn or otherwise secured to itself to form a tubular structure. As described in this detailed description a circular weaving machine is utilized.

Referring now to FIGS. 12 and 13 circular weaving machine 4700 is depicted. Weaving machine 4700 includes a plurality of shuttles, for example, one to three shuttles may be utilized. Further, four to six shuttles may be utilized. In still other forms greater than six shuttles may be used. For example, six to twelve shuttles may be utilized. In FIG. 12, for example, six shuttles 4702 are utilized on which are located bobbins 4704 which hold thread to be deposited between warp threads used to form a tubular structure 4600. Although shown with six shuttles 4702, in other forms a greater or fewer number of shuttles may be utilized. As depicted, weaving machine 4700 includes first shuttle 4710, second shuttle 4711, third shuttle 4712, fourth shuttle 4713, fifth shuttle 4714, and sixth shuttle 4715. The shuttles 4702 deposit weft threads 4606 between warp threads 4604 that are fed into weaving machine 4700 (see FIG. 14). As the weft threads 4606 are woven between the warp threads 4606 a tubular structure 4600 is formed. Tubular structure 4600 may therefore be continuously formed without seams along its length. This tubular structure 4600 that is formed of a circular woven structure is pulled away from weaving machine 4700 and may be wound up on a wheel or cut away for further processing.

Utilizing a particular number of shuttles and bobbins impacts or influences the woven structure that weaving machine 4700 forms. Because weaving machine 4700 includes shuttles 4702 that rotate about a track, a pattern of the threads located within the shuttles 4702 will be repeated along the length of the tube formed by weaving machine 4700. For example, a first thread type may be located on the bobbins of first shuttle 4710, second shuttle 4711, and third shuttle 4712. A second different thread type may be located on the bobbins of fourth shuttle 4713, fifth shuttle 4714, and sixth shuttle 4715. When weaving machine 4700 is used, a pattern of weft threads that repeats over the length of the tubular structure formed by weaving machine 4700 is formed. For example, the first thread type is located in three adjacent weft positions. Then the second thread type is located in three adjacent weft positions. This pattern continues along the length of the tubular structure. It should be recognized that the starting point of the pattern can be changed. For example, with the same configuration of threads in shuttles 4702 as described above the weft pattern of the structure formed by the threads may start with two threads of the first thread type, then continue with three threads of the second thread type, and finish with one thread of the first thread type.

As demonstrated, the pattern subset may be changed depending on the point at which the pattern is determined to start. Further, smaller subsets of patters may also exist. For example, the bobbin on first shuttle 4710 may include a thread of a first thread type, the bobbin on second shuttle 4711 may include a thread of a second thread type, the bobbin on third shuttle 4712 may include a thread of the first thread type, the bobbin on fourth shuttle 4713 may in a thread of the first thread type, the bobbin on fifth shuttle 4714 may include a thread of the second thread type, and the bobbin on sixth shuttle 4715 may include a thread of the first thread type. In this example, the pattern of weft threads on the tubular structure formed by weaving machine 4700 may include first thread type, second thread type, and first thread type. Therefore, the pattern may be considered to be a three thread pattern. The pattern however may also be considered first thread type, second thread type, and first thread type, first thread type, second thread type, and first thread type. Therefore, the pattern may also be considered to be a six weft thread pattern.

Referring to FIGS. 12 and 13 the operation of weaving machine 4700 is depicted. As shown in FIG. 12, warp threads 4604 extend substantially vertically out of the page. Warp threads 4604 may remain substantially stationary laterally during formation of tubular structure 4600. Warp threads 4604 may, however, be pulled, or tensioned out of the page in a vertical direction during formation of tubular structure 4600. Although shown with 6 warp threads, in some forms weaving machine 4700 may be equipped with 168, 252, or 336 warp threads. In other forms, weaving machine 4700 may include between 50 and 500 warp threads. Shuttles 4702 carry thread that is deposited as weft thread. This weft thread is deposited between warp threads 4604. For example, as shown in FIG. 13, sixth shuttle 4715 deposits thread weft 4609 between warp threads 4604. After six shuttle 4715 passes, the warp thread 4606 may switch sides so that the next thread deposited is woven between warp threads 4604. This action continues until the desired length of tubular structure 4600 is formed. In this manner the weft threads are deposited between the warp threads. By utilizing a large number of warp threads, the weft threads may be substantially covered by the warp threads. In this manner the weft threads may be spaced from an inner and outer surface of tubular structure 4600. Therefore, if the weft threads are formed of a plastic material such as polyamide, the patient will not be able to feel the weft thread polyamide against the skin of the patient as the warp threads may cover the weft thread.

In some forms, the speed at which various procedures are carried out will impact the structure of tubular structure 4600. For example, a feed speed, or take-off speed may refer to the speed at which the tubular structure 4600 is pulled away from weaving machine 4700. As shown, feed direction 4750 is the direction in which tubular structure 4750 is pulled or tensioned. Altering the feed speed may alter the construction of tubular structure 4600 by changing the density of weft threads in tubular structure 4600. For example, if there is a faster feed speed, fewer weft threads may be deposited compared to a slower feed speed. Further, changing the shuttle speed may also influence the structure of tubular structure 4600. Shuttle speed may refer to the speed at which shuttles 4702 travel around weaving machine 4700. The faster shuttles 4702 travel, the greater the weft density of tubular structure 4600. Therefore, the feed speed and shuttle speed may be altered to form a particular tubular structure 4600.

In some forms, the tension within weft threads 4606 and warp threads 4604 may be altered or changed to form a tubular structure with particular features. In some forms, certain threads from shuttles 4702 may be in greater tension than other threads from shuttles 4702 during manufacturing. By varying the tensions of weft threads 4606 that shape and other properties of tubular structure 4600 may be altered or tuned. In still further forms, the warp thread tension may also be altered or tuned during manufacturing to provide a particular shape or other properties to tubular structure 4600.

In some forms, weaving machine 4700 may include provisions to provide support to tubular structure 4600 during manufacturing. In some forms, weaving machine 4700 may include a form such as thorn 4752. As the weft and warp threads are woven together, the threads may press against thorn 4752. Thorn 4752 may therefore provide a surface on which the threads are able to rest. In some forms, thorn 4752 may provide a form that defines the shape of tubular structure 4600.

5.5.2 Textile Structure

In one form of the present technology, a textile, fabric, or other network of fibers is utilized in forming air circuit 4170. This network of fibers may interact with each other to form a tubular structure such as tubular structure 4600 as shown in FIG. 15. Tubular structure 4600 is depicted as having a substantially flat or constant outer surface. This figure is for descriptive purposes and for visualization of a tubular structure. Tubular structure 4600, however, may be a ribbed structure such as depicted in FIG. 16. In some forms a flat woven structure may be formed and then stitched together along a seam to form a tubular structure. In other forms, flat knitting may be used. In still further forms, non-woven material such as felt may be utilized. In still further forms, braiding, circular knitting, or circular weaving may be utilized to form portions of air circuit 4170 such that a seamless tubular structure 4600 is formed. As depicted in the figures and discussed in this detailed description, tubular structure 4600 is formed using circular weaving, however, as described previously other forms of the present technology may utilize various other forms of an interaction of a network of fibers.

Utilizing a circular weaving pattern permits the use of yarns or strands that extend in either the warp (generally vertical) or weft (generally horizontal) direction. As utilized throughout this detailed description, yarn may refer to either weft or warp thread. Additionally the term "thread" may refer to a strand formed of either monofilament or multifilament fibers. For example, a warp thread may be formed of multifilament strands such that the warp thread is a multifilament thread. In other forms, however, a warp thread may be formed of a single monofilament strand or filament, however, this single strand may also be referred to as a thread.

Referring to FIG. 14 woven structure 4602 that is utilized to form tubular structure 4600 is depicted in detail. As shown, woven structure 4602 includes a plurality of warp threads 4604 and a plurality of weft threads 4606. The warp threads 4604 extend substantially vertically along the length of tubular structure 4600. Therefore, warp threads 4604 extend substantially parallel to a longitudinal axis that extends through tubular structure 4600. The term vertically is used to describe the orientation of the warp threads 4604 when tubular structure 4600 is oriented lengthwise in the vertical direction. It should be understood that when tubular structure 4600 is oriented lengthwise in the horizontal direction that the warp threads 4604 would be oriented in a horizontal direction. The term "vertical" is used to describe the relationship between the warp threads 4604 and the weft threads 4606. The term vertical is used to describe the orientation of the warp threads 4604 when tubular structure 4600 is oriented lengthwise in the vertical direction. It should be understood that when tubular structure 4600 is oriented lengthwise in the horizontal direction that the warp threads 4604 would be oriented in a substantially horizontal direction. The warp threads 4604 are oriented such that each thread extends from a lower edge 4608 to an upper edge 4610 without wrapping around the tubular structure 4600. For example, warp thread 4605 extends in a vertical direction directly from lower edge 4608 to upper edge 4610. In this form, warp thread 4605 does not wrap around the circumference of tubular structure 4600 but rather is located in substantially the same circumferential position along the length of tubular structure 4600. Although depicted as a portion of tubular structure 4600, the same configuration may be present along the length of tubular structure 4600.

In contrast, the weft threads 4606 wrap around the circumference of tubular structure 4600. While weft threads 4606 may begin at lower edge 4608 and end up at upper edge 4610 the weft threads 4606 do not extend directly from lower edge 4608 to upper edge 4610. As the weft threads 4606 spiral about the circumference of tubular structure 4600 the weft threads 4606 may be utilized to provide a support structure to tubular structure 4600 so that tubular structure 4600 does not collapse upon itself. The spiral and angle of a spiral of weft threads 4606 is discussed in further detail below.

Further, although only a portion of the woven structure 4602 of tubular structure 4600 is depicted in FIG. 14, in some forms substantially all of the outer surface of tubular structure 4600 includes woven structure 4602. In other forms, over half of the outer surface of tubular structure includes woven structure 4602. In still further forms, less than half of the outer surface of tubular structure 4600 includes woven structure 4602. The same or similar percentages may apply to other configurations of a network of fibers. For example, substantially all, over half, or less than half of tubular structure 4600 may be formed of a circular knit, circular braided, or non-woven material.

Additionally, although described with upper edge 4610 and lower edge 4608 is should be recognized that a warp thread need not extend to either edge to be considered a warp thread. For example, a warp thread may terminate spaced from and edge of tubular structure 4600.

In some forms, the weft threads 4606 may wrap completely around tubular structure 4600. For example, weft thread 4607 wraps around tubular structure 4600 such that weft thread 4607 is located in at least two locations along the length of tubular structure 4600. As shown, weft thread 4607 is located at first weft position 4612 and also in second weft position 4614 that is spaced from first weft position 4612. In the form as depicted in FIG. 14, five other threads of weft threads 4606 are located between weft thread 4607 as first weft position 4612 and weft thread 4607 at second weft position 4614. This in in contrast to warp threads 4604 that remain substantially in the same circumferential locations along the length of woven structure 4602. That is, warp threads 4604 maintain their positions along the length of woven structure 4602. For example, weft thread 4605 runs substantially vertical along the length of weft threads 4605 and woven structure 4602.

The weft thread of a circular woven material extends in a continuous spiral along the length of the material. Therefore, the weft yarn may not be precisely horizontal or perpendicular to the warp yarn. This permits the weft yarn to be continuously fed through a circular weaving machine without causing breaks in the weft yarn and allows the weft yarn to be incrementally and continuously spaced along the length of the material, in this application a tube.

The angle of the weft threads 4606 compared to the warp threads 4604 may be altered depending on a number of factors and variables. That is, the angle of the spiral nature of weft threads 4606 may be changed or altered during manufacturing by manipulating various components of weaving machine 4700. For example, varying the speed at which shuttles 4702 rotate about weaving machine 4700 may impact the angle at which the weft threads 4606 are located with respect to the warp threads 4604. For a given take-off or feed speed of the warp threads 4604, rotating the shuttles 4702 slowly around weaving machine 4700 will cause the angle A between warp threads 4604 and weft threads 4606 to increase. Likewise, rotating the shuttles 4702 at a faster speed about weaving machine 4700 at a given take-off speed will result in a smaller angle A between warp threads 4604 and weft threads 4606. The angle between warp threads 4604 and weft threads 4606 may also be impacted by the take-off or feed speed of the warp threads 4604 through weaving machine 4700. Increasing the feed speed of warp threads 4604 for a given rotational speed of the shuttles 4702 will result in a larger angle A between warp threads 4604 and weft threads 4606 of woven structure 4602. Likewise, decreasing the feed speed of warp threads 4604 for a given rotational speed of the shuttles 4702 will result in a smaller angle A between warp threads 4604 and weft threads 4606 of woven structure 4602. Therefore, the angles between the warp threads 4604 and weft threads 4606 can be adjusted during the weaving process.

In some forms, angle A may be between 0 and 45 degrees. In other forms, angle A may be between 0 and 5 degrees or 0 and 10 degrees. In still further forms, angle A may be a non-zero angle. In other forms, angle A may be between 5 and 25 degrees. In still further forms, angle A may be between 25 and 45 degrees. In some forms, angle A may be greater than 90 degrees. For example, based on the location of angle A as shown in FIG. 14, angle A may be approximately 95 degrees. In other forms angle A may be an angle that is not 90 degrees such that the weft threads 4606 and warp threads 4604 are not located completely perpendicular to each other. In other forms, angle A may be between 90 and 135 degrees. In still further forms, angle A may be between 95 and 105 degrees. In other forms, angle A may be between 105 and 135 degrees. In still further forms, angle A may be between 135 and 150 degrees. In still further forms angle A may be between 150 degrees and 165 degrees or larger.

The thread material used to form air circuit 4170 may be different in the warp and weft directions. In other forms, the thread material may be the same. Further, the same type of thread may be used. For example, the thread may have the same denier (mass of thread in grams per 9,000 meters length), decitex or dtex (mass of thread in grams per 10,000 meters in length), gauge, diameter, texture, insulation properties, and other properties. In certain forms of the present technology, different thread or monofilament strands are utilized in the weft and warp directions. These different threads may permit different properties of tubular structure 4600. For example, the warp threads may permit stretchability and flexibility of tubular structure 4600. The weft threads may restrict occlusion during use of tubular structure 4600. Additionally, tensile strength and hardness of a material may be varied to achieve particular properties in air circuit 4170.

In some forms, various configurations and arrangements of the weft and warp threads may be utilized. For example, in some forms, a weft thread may be stretchy or elastic in a first direction and provide stretch resistance in another direction. Further, in some forms, particular locations of woven structure 4602 may permit greater stretch when compared to other locations of woven structure 4602. By utilizing different strands with different material properties the features and properties of woven structure 4602 may be altered or tuned depending on the manufacturing desire. In still further forms, the warp threads may be varied depending on what particular properties are desired from woven structure 4602. For example, warp thread 4605 and the two adjacent warp threads may be formed with non-extensible materials. In this location woven structure 4602 may be substantially inextensible along the length. However, adjacent warp threads may have different properties that permit stretch. In this manner woven structure 4602 and therefore a structure that incorporates woven structure 4602 is able to have particularized properties such as stretch properties at particular locations.

As shown in FIG. 14, warp threads 4604 and weft threads 4606 are formed of substantially similar size and shape. This configuration is shown for illustrative purposes only. Although a woven structure such as depicted in FIG. 14 may be utilized in tubular structure 4600, tubular structure 4600 may utilize different weft threads such as depicted in FIGS. 19-24, for example. That is, weft threads of different sizes and materials may be used. Further, although depicted and described with same-sized warp threads, in other forms warp threads of different sizes and properties may be utilized.

As shown in FIG. 14, woven structure 4602 depicts a plain weave configuration. This means that the warp and weft threads go over and under each other one at a time. For example, warp thread 4605 goes under weft thread 4607 and first weft position 4612. Travelling upwards warp thread 4605 then goes over the adjacent weft thread and then under the next adjacent weft thread and so on. The warp threads adjacent warp thread 4605 have the opposite configuration. For example, an adjacent warp thread goes over weft thread 4607 in first weft position 4612, and then under the next adjacent weft thread and then over the next adjacent weft thread and so on. Similarly, the weft threads follow the same one over one under configuration. For example, weft thread 4607 in first weft position 4612 goes over warp thread 4605, and then under the next adjacent warp thread, and then over the next adjacent warp thread and so on. Warp threads adjacent to warp thread 4605 have the opposite configuration. Other configurations may be possible such as basket weave, satin, twill and other weave or and combinations of weaves.

As described in this detailed description, when a warp thread is said to be adjacent to another warp thread the adjacent threads are to be in different orientations regarding over or under a weft thread. For example, warp thread 4605 is adjacent warp thread 4603. However, as described previously, weft thread 4607 in first weft position 4612 passes over warp thread 4605 and under adjacent warp thread 4603. In other configurations, however, adjacent warp threads may both be located under or over the same weft thread. Such a configuration may occur, for example, in a basket weave configuration. It should be recognized that the same or similar configuration is true with respect to weft threads. That is, when a weft thread is adjacent another weft thread the adjacent threads are to be in different orientations regarding over or under a warp thread.

5.5.3 Tubular Structure

The tubular structure 4600, which is formed of the woven structure 4602 that includes both warp and weft threads, forms a portion of air circuit 4170. As described above, the tubular structure 4600 may include different sizes and shapes of warp and weft threads. As shown in FIG. 15, tubular structure 4600 is formed with a substantially constant inner and outer diameter. Tubular structure 4600 is depicted in FIG. 15 for illustrative purposes to depict a possible orientation or view of tubular structure 4600. Although shown with a constant diameter, tubular structure 4600 may be formed with various diameters along its length.

Tubular structure 4600 may be formed with various cross-sectional sizes. In some forms the outer bounds of the outer diameter of tubular structure 4600 is 18 millimeters. In other forms the maximum outer diameter of tubular structure 4600 is 20 millimeters. In still further forms, the outer diameter of tubular structure 4600 is 15 millimeters or less. In other forms, the maximum outer diameter of tubular structure 4600 is greater than 18 millimeters and/or greater than 20 millimeters. For example the maximum outer diameter may be between 35 and 60 millimeters or between 50 and 80 millimeters. The inner diameter may also include various dimensions. In some forms, the inner bounds of the inner diameter of tubular structure 4600 is about 15 millimeters. In other forms the inner diameter of tubular structure 4600 is between 15 and 18 millimeters. In still further forms the inner diameter of tubular structure 4600 is between 18 and 20 millimeters. In still further forms, the inner diameter of tubular structure 4600 is greater than 20 millimeters. For example the inner diameter of tubular structure 4600 is between 20 and 50 millimeters or between 30 and 75 millimeters. In other forms, the inner diameter of tubular structure 4600 is less than 15 millimeters. The inner and outer diameters of tubular structure 4600 may be modified depending on the quantity of air to be passed through air circuit 4170.

In some forms, the diameter of tubular structure 4600 may be variable along its length. In some forms, tubular structure 4600 may have a variable outer diameter. In other forms, tubular structure 4600 may have a variable inner diameter. In still further forms, tubular structure 4600 may have both a variable inner diameter and a variable outer diameter. For example, as shown in FIG. 16, the inner and outer diameter of tubular structure 4600 is variable along the length of tubular structure 4600. In other forms, the diameter of tubular structure 4600 may increase or decrease along the length of tubular structure 4600. Increasing or decreasing the diameter may impact the structure integrity of tubular structure 4600 as well as impact the flow of air through tubular structure 4600 when utilized in conjunction with an RPT device. Additionally, tubular structure 4600 may have a substantially constant inner and/or outer diameter.

In some forms, tubular structure 4600 may be particularly formed to enhance the bend characteristics of tubular structure 4600. Referring to FIG. 16, a portion of tubular structure 4600 is depicted in side view. As shown, tubular structure 4600 includes a ribbed structure 4616. Ribbed structure 4616 may include ridges 4618 and valleys 4620. The ridges 4618 may have negative curvature with respect to an outer surface of tubular structure 4600 whereas the valleys 4620 may have a positive curvature with respect to an outer surface of tubular structure 4600. On the interior surface of tubular structure, an opposite configuration is present. The ribbed structure 4616 may permit tubular structure 4600 to bend at particular locations, while also permitting flexibility and providing support to tubular structure 4600 to resist occlusion of tubular structure 4600.

In some forms, the threads may have different tensions during manufacturing. For example, in some forms, the weft threads that extend from the bobbins of shuttles 4702 may have different tensions during manufacturing. A first weft thread from first shuttle 4710 may be deposited between warp threads 4604 at a first tension. A second weft thread from second shuttle 4711 may be deposited between warp threads 4604 at a second higher tension. Because the second weft thread is deposited with a higher tension, the second weft thread may tend to constrict the size of the tubular structure at the location of the second weft thread. Therefore, the cross-section of the tubular structure along the location of the second weft thread may be smaller than that of the cross-section at the location of the first weft thread.

In one form, the different tensions of the weft threads during the manufacturing of tubular structure 4600 may assist in forming the ribbed structure as shown in FIG. 16. For example, in some forms, the valleys 4620 may be formed with weft thread that was under greater tension during manufacturing than the weft threads located in the ridges 4618 of tubular structure 4600.

In other forms, the threads may have different elasticities that assist in forming the ridges 4618 and valleys 4620. In some forms, the weft threads of the valleys 4620 may have greater elasticity than the weft threads of the ridges 4618. During manufacturing the elastic threads and the less-elastic threads may be tensioned to a same or similar tension. Due to the higher elasticity of the elastic threads, the elastic threads may stretch to a greater extent than the less elastic threads. Once the tension from the shuttles is released from the elastic threads, the elastic threads may contract to a steady state. This contraction may make the cross-section of tubular structure 4600 smaller in the areas with a more elastic thread when compared to a less elastic strand. The contraction of the elastic threads may therefore cause the valleys 4620 to be formed. Because the less elastic threads do not contract as much as the elastic threads, the less elastic threads may be located in the peaks of a ribbed structure. Further, the threads located between the peaks and valleys of the ribs may be more elastic than the weft threads of the peaks and may also be less elastic than the weft threads of the valleys.

As shown in FIG. 17, as a portion of tubular structure 4600 is bent, the ridges 4618 abut each other along the tighter inner arc 4622. The ridges 4618 provide a stopping point for how tight of an arc may be formed during bending of tubular structure 4600. Different widths and heights of ridges 4618 may impact how tight the inner arc 4622 may be. For example, narrower ridges 4618 may permit a tighter arc to be formed than wider ridges 4618. Taller or larger ridges may also impact the inner arc 4622. For example, taller ridges may abut one another more so than shorter ridges such that short ridges may permit a tight inner arc 4622 than taller ridges 4618.

In addition to the size of ridges 4618, the material utilized within ridges 4618 may impact the arc size and shape. In forms in which ridges 4618 include a flexible and/or weak material, when the ridges 4618 abut one another the ridges 4618 may simply bend or distort into one another because the ridges 4618 are not strong enough to resist a shape change. In these forms, the tubular structure 4600 may kink along the inner arc 4622. In other forms, ridges 4618 may include a stronger material that is able to withstand the force from adjacent ridges such that during bending a smooth and continuous inner arc 4622 may be formed.

In some forms, various diameters of weft threads may be utilized. In some forms, the weft threads of the ridges 4618 and valleys 4620 may have larger diameters than the diameters of the weft threads that extend between the ridges 4618 and valleys 4620. Varying the diameters of the weft threads of the valleys 4620 and ridges 4618 may vary the width of the valleys 4620 and ridges 4618. Further the diameters of the weft threads may influence the shape of the tubular structure 4600. In other forms, the diameters of the threads may be varied at any of the locations. For example, the diameters of the weft threads on the slops may be larger than those of the weft threads in the valleys 4620 or ridges 4618. In other forms, the diameters of the threads may be different all along the length of the tubular structure 4600. For example, one weft thread in a valley may be larger than an adjacent weft thread in the valley. Further, the diameters of the weft threads in the slopes may be different from one another.

As shown in FIG. 17, while ridges 4618 abut one another along inner arc 4622, along outer arc 4624 ridges 4618 are spread apart from one another. In this manner valleys 4620 are spread out to permit ridges 4618 to be spaced from one another along outer arc 4624. The length of material within valleys 4620 between the ridges 4618 therefore influences how much a tubular structure 4600 is permitted to bend. For example, if less length of material is between each of ridges 4618 there is less material that is able to be stretched or flattened to permit outer arc 4624 to be tightly bent. Additionally, a greater quantity of material within valleys 4620 may permit a tight outer arc 4624 to be formed.

In addition to quantity or length of material between ridges 4618, the material of valleys 4620 and ridges 4618 may alter the amount that tubular structure 4600 is able to bend. For example, if the material of valleys 4620 is not stretchable, the valleys 4620 along the outer arc 4624 will resist bending. Likewise if the material of valleys 4620 is a stretchable material then tubular structure 4600 will be permitted to bend to a greater degree than if the material is not stretchable.

FIG. 17A depicts a possible arrangement of weft threads 4606 within the tubular structure 4600 as depicted in FIG. 17. This arrangement is the same as depicted in FIG. 20. Weft arrangement 4637 may be utilized in tubular structure 4600, as can other arrangements as depicted in FIGS. 19-24. As shown, thread no. 1 thread and thread no. 5 thread are located within a ridge of tubular structure 4600. Additionally, thread no. 4 threads are located in the valleys 4620 of tubular structure 4600. Further, the thread no. 2 thread and the thread no. 3 thread are arranged on the slope that extends from the valleys 4620 to the ridges 4618. As shown in FIG. 17*a* the warp threads are extend along the weft threads such that the weft thread are bounded by the warp threads. Various other configurations that include monofilament threads, multifilament threads and any combination of multifilament threads and multifilament threads may also be utilized to form portions of the valleys 4620 and ridges 4618. Further, any combination of the thread types listed in chart 4632 or other threads may be combine in various orders to form a ribbed structure like tubular structure 4600 as depicted in FIG. 17. In some forms, the ribbed structure may be formed by utilizing weft threads with different elasticities. For example, in some forms, weft threads with less elasticity may be located along a ridge of the ribbed structure. Additionally, weft threads located in the valleys may have greater elasticity than the weft threads located in the peaks. Further, weft threads located between the peaks and the valleys may have elasticities that are between the elasticities of the weft threads located in the peaks and the weft threads located in the valleys.

In some forms, tubular structure 4600 may be particularly formed to enhance the stretchability of tubular structure 4600. As shown in FIG. 18, tubular structure 4600 is subjected to tensile force 4630. Tensile force 4630 stretches the material of valleys 4620 and ridges 4618, and partially flattens tubular structure 4600. By forming tubular structure 4600 with ridges and valleys, the material used to form ridges 4618 and valleys 4620 may be permitted to stretch or flatten. In comparison to a tubular structure with a constant or linear outer surface and/or inner surface, tubular structure 4600 may permitted to stretch to a greater extent. The flexibility and stretchability of tubular structure 4600 may permit a patient to be comfortable while utilizing an RPT device that makes use of tubular structure 4600.

5.5.3.1 Weave Type

In some forms, a tubular structure may be woven in a particular manner to achieve particular properties within the air circuit 4170. In some forms, a plain one to one weave, satin weave, twill weave, basket weave, or leno weave may be utilized. A plain weave may be utilized for stability and includes a weft thread that alternates over and under the warp thread. A leno weave may be utilized to secure fibers within a particular woven structure. A satin weave may be utilized for contours or to provide particular feel to the woven structure. A twill weave may be utilized for a particular look while maintaining stability of the woven structure. A basket weave may be utilized for pliability while maintaining strength. As described in this detailed description the woven structure of the tubular structure is a plain one-to-one weave. In other forms, different weave types or combinations of different weave configurations such as those listed above, may be utilized.

In other forms, different types of structures may be utilized to form tubular structure 4600. For example, as previously described, tubular structure 4600 may be formed using knitting, braiding, or any other form of manufacturing that includes an interlocking network of fibers. In such forms, various braiding, knitting, and other configurations may be used.

5.5.3.2 Warp Threads

In some forms, the warp threads may be formed of a particular yarn. In some forms the network of fibers includes yarn or strands of material that may be monofilament or multifilament in construction. In one form, of the present technology the warp threads are formed of an elastic polyurethane fiber such as LYCRA®. In some forms, the warp threads may also include a coating, for example a polyester coating. These material may impart particular properties to tubular structure 4600.

The warp threads may be formed of various materials. In some forms, the warp threads may be formed of natural or synthetic materials. For example, in some forms the warp threads may be formed of cotton, wool, or silk. In other forms, the warp threads may be formed of elastane, rayon, polyester, polyurethane, plastic or other synthetic material. The material of the warp thread may also be combination of different materials. For example, in some forms the warp threads may be formed from a combination of synthetic materials and natural materials. In other forms, each thread may be formed entirely of a natural or synthetic material, however threads made from natural materials and threads made from synthetic materials may each be utilized to form a tubular structure. In still further forms, the threads may be formed of a combination of fibers of different natural or synthetic materials. For example, a particular thread may be formed from both cotton and wool fibers. Additionally, a particular thread may be formed of polyester and elastane fibers. Further, threads formed of particular materials may be used to form the tubular structure. For example, a first thread may be formed of polyester and a second thread may be formed of elastane. The various threads may be utilized to increase or decrease particular properties of the tubular structure. For example, particular materials may be utilized to increase comfort whereas other materials may be utilized to increase the stretching ability of the tubular structure. In other forms, threads may be utilized with various dtex values. Additionally, threads may be formed with varying numbers of fibers and plies. Still further, threads may be formed with different twists (e.g. S twist or Z twist) as well as number of twists per unit length.

In some forms, the number of warp threads utilized may be particularly selected to provide adequate and consistent sealing along the outer surface of tubular structure 4600. In some forms, 252 warp threads may be utilized. In other forms, 168 warp threads may be utilized. In still further forms, 336 warp threads may be utilized. In still further forms between 50 and 168 threads may be utilized. In other forms between 168 and 252 warp threads may be utilized. In still further forms, between 252 and 336 warp threads may be utilized. Additionally, greater than 336 warp threads may be utilized.

By varying the number of warp threads the properties of tubular structure 4600 may be altered. For example, tubular structure 4600 of a given size that includes 168 warp threads may be more flexible than an air circuit of the same size that includes 336 warp threads. Likewise, a tubular structure that includes 336 warp threads may form a closer structure than a tubular structure formed with 168 warp threads. By increasing the number of warp threads of the same material, the tubular structure may have greater structural integrity while forming a more closed a tightly formed air circuit than an air circuit that includes 168 warp threads.

Referring to FIGS. 27-29, various different forms of tubular structure 4600 are depicted in a free standing manner. As shown each tubular structure 4600 is supported by a pin 4601. The tubular structure is then permitted to flow downward under its own weight. As shown, tubular structure 4600 in FIG. 27 is formed with 168 warp threads. Tubular structure 4600 of FIG. 28 is formed with 252 warp threads. Tubular structure 4600 of FIG. 29 is formed with 336 warp threads. As described previously, the number of warp threads within tubular structure 4600 impacts many properties of tubular structure 4600, including the ability and tendency of tubular structure 4600 to bend. As shown in FIGS. 27-29 each of the variations of tubular structure 4600 are supported in the center by pin 4601 and permitted to bend naturally with accordance to the weight of the tubular structure. That is, each is allowed to bend under its own weight. As shown, the various tubular structures bend at different angles depending on the number of yarns in the warp direction. Increasing the number of warp threads decreases the natural bending of tubular structure 4600. As shown, tubular structure 4600 of FIG. 27 that includes 168 warp threads has a tighter or sharper curvature when compared to tubular structure 4600 of FIG. 28 and FIG. 29 that include 252 and 336 warp threads, respectively. Although shown with specific numbers of warp threads, the number of warp threads may be altered to provide different bend characteristics. For example, a tubular structure may be formed that has between 168 and 252 warp threads. Such a tubular structure would have a bend that is between that shown in FIG. 27 and FIG. 28. Having a warp thread number closer to 168 would form a tubular structure with properties closer to tubular structure 4600 of FIG. 27. Including a number of warp threads closer to 252 would form a tubular structure that bends under its own weight in a similar manner as to tubular structure 4600 of FIG. 28. The number of warp threads utilized may also be between 252 and 336. The properties of tubular structure 4600 would change accordingly depending on the number of warp threads. Additionally, greater than 353 warp threads may be utilized in some forms, while fewer than 168 warp threads may be utilized in other forms.

Additionally, varying the number of threads in the warp direction also impacts the weave density of tubular structure 4600. For example, tubular structure 4600 that includes 336 warp threads woven in plain weave will have a greater weave density that tubular structure 4600 that includes 168 warp threads in a plain weave configuration. By varying the density of the weave the weight of tubular structure 4600 may also be impacted. In some forms, a lightweight tubular structure 4600 may be desired such that the user will not be negatively impacted by the weight of the tubular structure 4600.

In some forms, a particular length of tubular structure 4600 may be formed to be lightweight. In some forms, a portion or entire length of tubular structure 4600 may be two meters. Two meters of tubular structure 4600 may have various weights depending on material selected and warp and weft densities among other factors. In some forms, two meters of tubular structure 4600 may be formed such that tubular structure 4600 weighs under 100 grams. In some forms, two meters of tubular structure 4600 is configured such that tubular structure 4600 weights under 75 grams. In still further forms two meters of tubular structure 4600 weighs approximately 64 grams. In still further forms, two meters of tubular structure 4600 weighs less than 64 grams. Additionally, in other forms, two meters of tubular structure 4600 may weight greater than 100 grams.

The number of warp threads in tubular structure 4600 may also impact the flexibility of tubular structure 4600. The flexibility may include the ability of tubular structure 4600 to stretch lengthwise (see FIG. 18) as well as the ability of tubular structure 4600 to expand when exposed to pressurized air from within tubular structure 4600. Additionally, flexibility may refer to the ability of tubular structure 4600 to contract when exposed to a pressure or force external to tubular structure 4600. Flexibility also includes the ability of the tubular structure 4600 to bend (see FIG. 17) with respect to an axis that extends through the center of tubular structure 4600.

Increasing the number of warp threads of a given material in tubular structure 4600 may decrease the lengthwise flexibility. Conversely, reducing the number of warp threads of a given material may increase the lengthwise flexibility compared to tubular structure 4600 that includes a greater number of warp threads.

A tube with a greater number of warp threads may also not radially expand to the same degree as a tube with a fewer number of warp threads. The greater the density of warp threads of a given material, the less the tube may be able to expand radially. The number of warp threads may be chosen to permit expansion or to limit expansion depending on the desired properties of air circuit 4170.

A tubular structure with a greater number of warp threads may also not bend to the same degree as a tubular structure with a fewer number of warp threads. In some forms, a smaller quantity of force may be necessary to bend tubular structure 4600 that includes a fewer number of warp threads. Further, in some forms, tubular structure 4600 with a fewer number of warp threads such as 168 warp threads may kink easier than tubular structure 4600 that includes a greater number of warp threads. Therefore, too few warp threads may increase the likelihood of accidental occlusion through bending of the tubular structure 4600.

A tubular structure with a greater number of warp threads may have a larger radius of curvature when bent when compared to a tubular structure with a fewer number of warp threads (for example, see FIG. 29). A patient may desire to orient air circuit 4170 in various orientations for comfort. In some forms, the patient may wish to bend or contort tubular structure 4600 to accomplish these various orientations so that the patient can comfortably utilize the therapy device. The ability of tubular structure 4600 to be bent with a smaller radius of curvature may permit the patient to particularly arrange air circuit 4170 so that the patient is comfortable. Therefore, a balance between too few of warp threads such that tubular structure 4600 may kink and too many warp threads such that tubular structure 4600 is permitted to bend only in large arcs may be struck or accomplished. The number of warp threads that may be utilized to accomplish such an outcome may depend on the thread material type as well as the weight or thickness of the thread utilized for the warp thread. For example, a fewer number of stretch-resistant warp threads may be utilized to form a particular tubular structure 4600 compared to flexible warp threads.

In one form, warp thread may be multifilament or monofilament thread. In one form, the warp thread may include a core material wrapped with other fibers. Utilizing a core yarn thread permits the warp threads to incorporate the features of both the core material and the fibers in one yarn. In some forms, the warp thread incorporates a core of LYCRA® with a particular dtex. In some forms the core may be 156 dtex. In other forms the core may be 1880 dtex. In still further forms the core may be between 156 and 1880 dtex. In other forms the core may be less than 156 dtex or greater than 1880 dtex. The coating of the warp thread may have different properties than the core. In some forms the dtex of the coating may be 76 dtex. In other forms the coating may be 110 dtex. The coating and core may be changed depending on the particular properties to be utilized in the warp direction. Other dtex numbers may be utilized as well, for example 150, 250, 350, 450, 550, etc. dtex as well as the range between the enumerated dtex numbers may be utilized in threads as a core or coat for any particular thread in the warp direction or the weft direction.

The particular thread that is used for the warp threads may impact the stretchability and stability of the tubular structure 4600. Utilizing a stretchable material may permit the tubular structure 4600 to in turn be stretchable. However, too stretchable a material may require an increase in the number of warp threads in order to form a stable structure. Additionally, varying the stretchability of the material of the warp thread may also permit a greater or fewer number of warp threads to be utilized during manufacturing.

5.5.3.3 Weft Threads

Various configurations and arrangements of the weft thread may be utilized. In some forms, tubular structure 4600 may be formed using a circular weaving machine that includes six shuttles as depicted in FIGS. 12 and 13. In other forms, a circular weaving machine with greater than six or fewer than six shuttles may be utilized. As described in this detailed description, a circular weaving machine with six shuttles is utilized.

As described with reference to FIGS. 12 and 13 each shuttle may be fitted with a bobbin that includes a thread, strand, or other linear component. The shuttles are configured to move in a circular motion such that the threads located on the bobbins within each shuttle are woven between the warp threads thereby forming a circular tube-shaped object that includes warp and weft threads.

The weft threads therefore spiral along the length of the tubular object and in combination with the warp threads form a tubular structure. Various material types, material densities, and configurations of weft thread may be utilized to form a particularly comfortable and useful tube for use with a respiratory device.

The weft threads may be formed of various materials. In some forms, the weft threads may be formed of natural or synthetic materials. For example, in some forms the weft threads may be formed of cotton, wool, or silk. In other forms, the weft threads may be formed of elastane, rayon, polyester ("PES"), polyurethane, plastic, polyamide ("PA") or other synthetic material. The material of the weft thread may also be a combination of different materials. For example, in some forms the weft threads may be formed from a combination of synthetic materials and natural materials. In some forms the threads may be formed of a combination of synthetic materials and natural materials. In other forms, each thread may be formed entirely of a natural or synthetic material, however threads made from natural materials and threads made from synthetic materials may each be utilized to form a tubular structure. In still further forms, the threads may be formed of a combination of different natural or synthetic materials. For example, a particular thread may be formed from both cotton and wool. Additionally, a particular thread may be formed of polyester and elastane. Further, threads formed of particular materials may be used to form the tubular structure. For example, a first thread may be formed of polyester and a second thread may be formed of elastane. The various threads may be utilized to increase or decrease particular properties of the tubular structure. For example, particular materials may be utilized to increase comfort whereas other materials may be utilized to increase the stretching ability of the tubular structure. Any combination of thread configurations and thread types may be utilized in any one or all of the bobbins on shuttles 4702.

In some forms, the weft thread may be monofilament or multifilament thread. The particular thread may be chosen for particular properties such as stretch resistance or comfort. In some forms a combination of monofilament and multifilament threads may be utilized in a particular tubular structure.

In some forms, the weft thread may be organized to achieve a particular structure or to utilize a particular properties of the weft thread. In some forms, multiple weft threads may be utilized in conjunction with each other to form a particular structure while permitting particular stretch and structure characteristics between each of the weft threads. Some weft threads may be utilized in particular to provide a structure to prevent the tubular structure from occluding during use. The weft threads may also be utilized to support the tubular structure to reduce the likelihood of occlusion and resist occlusion from external forces. Further, the weft threads may also be utilized to permit flexibility and stretching of the tubular structure.

In some forms the weft density of the tubular structure may be varied depending on the desired characteristics of the tubular structure. The weft density may also affect the ability of the tubular structure to be formed on a machine. For example, too low of a weft density may cause a machine to malfunction while forming the tube. Likewise too high of a weft density may also cause a circular weaving machine to malfunction during formation of the tubular structure. Therefore a particular weft density should be selected so that the tubular structure is able to be formed on a weaving machine.

The weft density may affect the flexibility and stability of the tubular structure. A high weft density may increase stability of the tubular structure, however the flexibility of the tubular structure may be diminished. Likewise a low weft density may increase the flexibility of the tubular structure, but the stability of the structure may be diminished. The word stability is used to mean the ability of the tubular structure to hold and maintain a shape, as well as the consistent return to a particular shape after exposure to a particular force. For example, a high weft density structure may have a particular shape, and when depressed or compressed the high weft density structure is slightly deformed. When the force is removed the high weft density structure may return to its original shape. In contrast a lower weft density structure may not have as particularly defined tubular structure initially. The lower weft density structure may compress or depress to a greater degree than the high weft density structure. When the force is removed from the lower weft density structure the structure may not return to its original shape, or may take longer to do so. In some forms, it may be desirable to have a flexible yet stable tubular structure. Therefore, the weft density may be between a high weft density and a lower weft density. In some forms, the weft density may be between 10 threads per cm and 100 threads per cm. In some forms, the weft density is between 20 threads per cm and 45 threads per cm. In still further forms, the weft density is between 30 threads per cm and 75 threads per cm. In other forms, the weft density is between 60 threads per cm and 100 threads per cm. In some forms, the weft density may be about 30 threads per 10 cm. In other forms, the weft density may be about 40 threads per 10 cm. In still further forms, the weft density may be approximately 50 threads per 10 cm.

Referring to FIGS. 30-32, schematic views of a portion of tubular structure 4600 with various weft densities are depicted. In FIG. 30 tubular structure 4600 has a weft density of approximately 50 threads per 10 cm. In FIG. 31, tubular structure 4600 has a weft density of approximately 40 threads per 10 cm. In FIG. 32, tubular structure 4600 has a weft density of approximately 30 threads per 10 cm. As shown, the space between each of the weft threads is different depending on the weft density. As described with respect to FIG. 17, varying the location of the weft threads may impact the bendability of tubular structure 4600. For example, a higher weft density will likely decrease the ability of tubular structure 4600 to bend to a great degree. Since the ridges 4618 will be located closer to one another, the ridges 4618 will abut one another after a small amount of bending when compared to ridges 4618 that are spaced farther apart from one another.

Additionally, varying the weft density also varies the angle between the weft threads 4606 and the warp threads 4604. Changing the angles between the weft threads 4606 and the warp threads 4604 may impact the occlusion resistance of tubular structure 4600. When the weft threads 4606 are spaced farther from each other, the ability of the weft threads 4606 to resist a change in shape is reduced. This is due in part because less mass or material is located within a particular location to resist a force. Therefore, utilizing a weft density that is too low may increase the possibility of occlusion of the tubular structure 4600.

In addition to physical properties of the warp and weft materials, the materials may also be chosen for particular visual aspects individually as well as with the tubular structure. In some forms, a textile or fabric look may be desired. In such a case a material such as Core LYCRA® 156 dtex Coat PES dtex 76f24x1 may be utilized, for example in the warp direction. Utilizing this particular material may permit a material with a matte as opposed to a shiny or glossy finish to be located along the tubular structure. A patient may appreciate the visual aesthetics of a matte or flat material. Further, the feel of the material may be pleasing to the patient. This is in contrast other tubular structures that may be formed with silicone or a plastic material along an outer surface. By orienting a textile-type material along an outer surface of the tubular structure, a patient may be able to feel the softness of the material in comparison to a hard or cold plastic or silicone.

Additionally, the physical properties may affect how the tubular structure appears in different manners. For example, the tubular structure may be particularly formed so that the tubular surface is consistent or constant along the length of the tubular structure. For example, the tubular structure may have grooves and crests. If the grooves or crests are inconsistent in height and/or width the patient may deduce that the tubular structure was not properly made or that the tubular structure will not function correctly. Maintaining a particular shape of the tubular structure may therefore increase the likelihood that a patient will continue to use the device to receive therapy.

In some forms, various diameters of materials may be utilized to form a tubular structure. By varying the diameters of the threads the overall appearance of the tubular structure may be varied. Further, varying the diameters of the threads may also impact the physical properties of the tubular structure. For example, in some forms a monofilament weft thread may be used with a diameter of approximately 0.7 millimeters. In other forms, a monofilament with a diameter of between 0.5 to 0.9 millimeters may be utilized. In some forms, a monofilament thread may include a diameter larger than 0.9 millimeters or smaller than 0.5 millimeters. The monofilament thread may assist in maintaining the circular structure of the tubular structure, and may assist in providing a particular concertina shape to the tubular structure. In other forms, a monofilament with a diameter of approximately 0.8 millimeters may be utilized. The monofilament with a diameter of 0.8 millimeters may provide a greater variant or deviation from a center line of the tubular structure. That is, in the concertina shape of the tubular structure the ridges or peaks may be higher than the ridges or peaks of a tubular structure formed with a monofilament structure with a diameter of 0.7 millimeters. In some forms, a patient may prefer a tubular structure with a lower profile or lower deviation from a baseline center line. The lower profile may provide less irritation to a user due to the more consistent shape of the tubular structure with a monofilament of 0.7 millimeters.

The monofilament may act as a helical coil that is utilized to support the tubular structure. The helical coil may be utilized to resist occlusion or compression by a force that is perpendicular to the monofilament. Further, in some forms the monofilament may be surrounded by textile materials via warp threads. This spaces the monofilament from the skin of a user such that the monofilament is protected from the outside surface of the tubular structure. By spacing the monofilament from an outer surface, the likelihood that a patient may be able to feel the monofilament is reduced.

5.5.3.4 Tubular Structure Configurations

Referring to FIGS. 19-24, along with chart 4632 of FIG. 25 and chart 4634 of FIG. 26 depict various forms of weft thread orientations within a tubular structure. The figures depict the orientation of various weft threads in the tubular structure. The warp structure, although able to be varied, for purposes of explanation it is formed of 252 threads and the thread is Core LYCRA® 156 dtex, coat PES dtex 76f24x1. As described previously, various materials may be utilized in the warp direction. Further, various quantities of threads may be utilized in the warp direction. That is, greater than or fewer than 252 warp threads may be utilized in the formation of a tubular structure. The warp and weft threads are formed in a plain weave. Again, as described previously, other structures may be utilized such as basket weave or twill. Additionally, each tubular structure of FIGS. 19-24 has an outer diameter of 18 millimeters. As described previously, the diameter of each tubular structure may be different, for example between 15 and 30 millimeters, however for purposes of description, each tubular structure is assumed to have a maximum outer diameter of 18. That is, due to the ribbed nature of a tubular structure, the outer diameter at the ridges is approximately 18 millimeters. Although the different forms shown in FIGS. 19-24 are formed with the same warp thread and warp density, it should be recognized that various warp threads and warp densities may be utilized, in addition to different weave patterns beyond a plain weave configuration. The weft structure may include various iterations of materials that are oriented in a particular manner. These threads assist in forming a lenticular or ribbed structure of the tubular structure. As described previously, different quantities of warp threads may be utilized in a tubular structure and different diameters of tubular structures may also be formed.

Referring to chart 4632, various materials are associated with thread numbers for ease of description in regards to various forms of tubular structures. These thread numbers are utilized to show the orientation of the threads within the tubular structures of FIGS. 19-24. In chart 4632, thread number 1 is a PA monofilament with a diameter of 0.7 mm. Thread number 2 is PA 6.6 Z150 which is 880 dtex. Thread number 3 is PA 6.6 Z300 which is 440 dtex. Thread number 4 has a core of LYCRA® with 1880 dtex and a coat of PEX text. dtex 110f36x1. Thread number 5 is a PA monofilament with a 0.8 millimeter diameter. Thread number 6 has a core of LYCRA® with 156 dtex and a coat of PEX text. dtex 76f24x1. Each of these materials may be chosen for particular properties including stretch characteristics as well as resiliency characteristics in addition to other characteristics such as touch and feel. Further, each thread may be utilized in the place of another and interchanged in order to achieve a particular property within the tubular structure. Chart 4632 lists possible material types but is not extensive and many other thread types and diameters may be utilized to form a tubular structure.

Chart 4634 shows the orientation of the weft threads within each of the tubular structures. The chart shows the shuttle within circular weaving machine 4700 as see in FIG. 12. The shuttles 1 through 6 (first shuttle 4710 through sixth shuttle 4715) travel around in a circular path and deposit such that the weft thread is woven with the warp thread. As the shuttles deposit thread the warp threads are moved vertically (for example, out of the page in FIG. 12). This creates a "spiral" effect of the weft threads within the tubular structure. Further, because the shuttles are located in a circular track, it should be recognized that shuttle 6 (for example, sixth shuttle 4715) thread may be located adjacent to the shuttle 1 (for example, first shuttle 4710) thread when assembled in the tubular structure. The orientation of the weft threads within the tubular structure may then repeat until a desired amount of tubular structure is formed. As the threads are deposited in the tubular structure, the shuttles deposit the threads in particular positions. For example, first shuttle 4710 deposits a thread in a first weft position which would be adjacent to a thread deposited by second shuttle 4711 in a second weft position. In some forms, multiple weft positions may be referred to a weft section. For example, a weft thread section may include weft threads deposited by third shuttle 4712 to sixth shuttle 4715. In other forms, a weft section may refer to a single weft position. For example, a weft section may include thread deposited only from third shuttle 4712 such that the weft position and weft section may be the same. During discussion of a weft section, each weft position may be referred to as a weft section position.

Referring now to FIG. 19, a schematic of a portion of a particular configuration of a tubular structure is shown with weft arrangement 4635. As shown, a particular arrangement of thread is utilized as produced in chart 4634. In the configuration of weft arrangement 4635, thread no. 1 is used in the first shuttle position. Thread no. 2 is utilized in the second shuttle position. Thread no. 3 is utilized in the third shuttle position. Thread no. 4 is utilized in the fourth shuttle position. Thread no. 3 is utilized in the fifth shuttle position. Thread no. 2 is utilized in the sixth shuttle position.

Thread no. 1 provides support to the tubular structure such that when compressed the tubular structure will resist occlusion. Thread no. 1 may in general be stronger and stiffer than other materials. That is, thread no. 1 may have greater tensile strength and/or stretch resistance. Further, in some forms thread no. 1 may have a greater diameter which may assist in providing additional support to keep the tubular structure remain open, even without pressurized air passing through weft arrangement 4635. Thread no. 2 may be deposited adjacent to thread no. 1 within weft arrangement 4635 of the tubular structure. When referring to weft threads being adjacent to one another, it is assumed that a warp thread is between the adjacent threads unless specified otherwise as described previously. Thread no. 2 may assist in providing support to the tubular structure. Adjacent thread no. 2 is thread no. 3. Thread no. 3 may be more lightweight that thread no. 2 as the dtex number of thread No. 3 is lower than that of thread No. 2, however, thread no. 3 may still be formed of polyamide. Adjacent to thread no. 3 is thread no. 4. Thread no. 4 includes a core of LYCRA® to assist in permitting stretch, and is also coated in polyester to provide thread no. 4 with greater stability. Thread no. 4 permits weft arrangement 4635 of the tubular structure to stretch while also maintaining stability of the tubular structure. Next to thread no. 4 is thread no. 3, and then thread no. 2 as the pattern of threads repeats until the pattern starts over with thread no. 1. This repeating pattern permits a uniform and continuous look and feel for a tubular structure with weft arrangement 4635 while also providing measurable stretch qualities along the length of the tubular structure that includes weft arrangement 4635.

FIG. 19, in addition to including weft arrangement 4635 also includes the orientation of warp threads 4604 with respect to the weft threads of weft arrangement 4635. As described previously, the warp threads 4604 extend under and over adjacent weft threads along the length of a tubular structure. In this manner the weft threads are bounded by warp threads on either side of the weft threads. Such a configuration may be present in tubular structures that include the weft arrangements as depicted in FIGS. 19-24, however for purposes of clarity the weft threads are not shown in all of the FIGS. 19-24.

Referring now to FIG. 20, weft arrangement 4637 is depicted. A cutaway portion of tubular structure 4600 that includes weft arrangement 4637 depicts the orientation of the weft threads within a portion of weft arrangement 4637 and within tubular structure 4600. Additionally, for clarity, only a portion of tubular structure 4600 is depicted with warp threads 4604. It should be recognized that tubular structure 4600 of FIG. 20 and other tubular structures that include the weft arrangements depicted in FIGS. 19-24 would also include warp threads 4604 that bound each of the threads of weft threads 4606. As shown, a particular arrangement of materials is utilized as produced in chart 4634. In the configuration of FIG. 20, thread no. 1 is used in the first shuttle position. Thread no. 5 is utilized in the second shuttle position. Thread no. 2 is utilized in the third shuttle position. Thread no. 4 is utilized in the fourth shuttle position. Thread no. 4 is utilized in the fifth shuttle position. Thread no. 3 is utilized in the sixth shuttle position.

In this configuration, two monofilaments are used adjacent one another. This configuration may improve the stability of weft arrangement 4637 when compared to weft arrangement 4635. By include two monofilaments of 0.7 mm and 0.8 mm diameter adjacent to one another, an occlusion resistant ridge may be formed. This ridge may be stronger than any ridge formed in weft arrangement 4635 due to the doubling up of large PA monofilaments. By including a larger monofilament in thread no. 5, the strength and resistance to occlusion may be increased when compared to weft arrangement 4635.

Additionally, thread no. 2, which has a higher dtex number is located adjacent thread no. 5. This orientation of threads may permit a gradual shift from the thicker, stronger monofilament strands to the stretchable materials such as thread no. 4. Likewise, thread no. 3 is located adjacent to thread number 1 to permit a gradual shift to the larger stronger monofilament strand of thread no. 1. Located between thread no. 2 and thread no. 3 are two distinct threads of thread no. 4. These two threads are located adjacent to one another such that a warp thread passes between thread no. 4 from the fourth shuttle position and thread no. 4 from the fifth shuttle position. By orienting two threads of thread no. 4 adjacent one another, the stretchability of a tubular structure incorporation weft arrangement 4637 may be pronounced in the region that includes the two thread no. 4 threads. Further, a valley or trough may be formed in area of weft arrangement 4637 that includes the two adjacent thread no. 4 threads.

The two threads of thread no. 4 adjacent to one another may also provide stability during a bending motion of weft arrangement 4637. Due to the fact that weft arrangement 4637 has two monofilament strands adjacent to one another, when bending a tubular structure with weft arrangement 4637 the monofilament strands may be less likely to change in shape or become distorted when influenced by an outside force. This force may also be spread on to the adjacent threads. In some forms, with a weaker thread such as thread no. 6 in the place of thread no. 4, a tubular structure with weft arrangement 4637 would kink when bent. Utilizing a stronger elastane thread such as thread no. 4 reduces the possibility of kinking when bending a tubular structure with weft arrangement 4637. Further, utilizing thread no. 4 in the particular location also may permit smooth curves when bending a tubular structure with weft arrangement 4637 because the thread no. 4 assists in maintaining a stable and consistent structure.

As shown in FIG. 20, the outer surface of tubular structure 4600 may be influenced by the size and shape of the weft threads of weft arrangement 4637. While the size of the threads may influence the shape of tubular structure 4600, the depiction in FIG. 20 is exaggerate and enlarged for purposes of explanation. For example, the ribbed structure may be due to the orientation of the weft threads and not only because of the different sizes of the weft threads. Additionally, as shown in FIG. 19-24 the inner surfaces of the weft threads are substantially parallel to one another. In some forms, such as depicted in FIG. 16, when tubular structure has a ribbed configuration the inner surfaces of the weft threads may be located within different longitudinal plains when compared to an adjacent weft thread. The configurations depicted in FIGS. 19-24 are utilized to depict variation iterations of thread configurations within a tubular structure.

Referring now to FIG. 21, a schematic of a weft arrangement 4639 is depicted. As shown, a particular arrangement of materials is utilized as produced in chart 4634. In the configuration of FIG. 21, thread no. 1 is used in the first shuttle position. Thread no. 1 is also utilized in the second shuttle position. Thread no. 2 is utilized in the third shuttle position. Thread no. 4 is utilized in the fourth shuttle position. Thread no. 4 is utilized in the fifth shuttle position. Thread no. 3 is utilized in the sixth shuttle position.

This orientation of threads is similar to the orientation of threads of weft arrangement 4637. In weft arrangement 4639, however, rather than including thread no. 1 adjacent to thread no. 5, weft arrangement 4639 includes two threads of thread no. 1 adjacent to one another. In this manner a consistent shape is produced in a tubular structure with weft arrangement 4639. The orientation of two monofilament threads next to one another assists in maintaining a stable construction while also permitting flexibility of a tubular structure with weft arrangement 4639. Further, utilizing monofilaments of the same size may permit a uniform appearance of the tubular structure. Also, using the same monofilament may reduce costs when compared to other tubular structures that use multiple monofilaments of different sizes.

Further a weft pattern may include various weft threads. A weft pattern may be a pattern that repeats throughout a tubular structure. Depending on the starting point of the pattern determines how the pattern is described. As shown in FIG. 21, weft arrangement 4639 includes a pattern of weft threads that will repeat along the length of a tubular structure that includes weft arrangement 4639. This is due to the arrangement of shuttles 4702 within weaving machine 4700. Shuttles 4702 are located in a track and therefore the arrangement of the weft threads is consistent along the length of a tubular structure. Weft arrangement 4639 includes a weft pattern 4669. This weft pattern includes a thread no. 1 thread adjacent to a thread no. 2 thread. The thread no. 2 thread is adjacent a thread no. 4 thread. The thread no. 4 thread is adjacent another thread no. 4 thread. The second thread no. 4 thread is adjacent to a thread no. 3 thread. The thread no. 3 thread is adjacent to a thread no. 1 thread. This pattern of threads then repeats itself along the length of the tubular structure. In this example, weft pattern 4669 may begin with thread that is deposited by second shuttle 4711. Various other patterns or subsets of patterns may also be included as described previously.

Referring now to FIG. 22, schematic of a portion of weft arrangement 4641 is depicted. As shown, a particular arrangement of materials is utilized as produced in chart 4634. In the configuration of FIG. 22, thread no. 5 is used in the first shuttle position. Thread no. 5 is also utilized in the second shuttle position. Thread no. 2 is utilized in the third shuttle position. Thread no. 4 is utilized in the fourth shuttle position. Thread no. 4 is utilized in the fifth shuttle position. Thread no. 3 is utilized in the sixth shuttle position.

The configuration of weft arrangement 4641 is similar to the configuration of weft arrangement 4637. In weft arrangement 4637, however, two of thread no. 5 are located adjacent to one another. A tubular structure with weft arrangement 4641 may have superior stability and occlusion resistance when compared to a tubular structure with weft arrangement 4639 and weft arrangement 4637 due to the double inclusion of thread no. 5. In some forms, however, a tubular structure with weft arrangement 4641 may not be as flexible as a tubular structure with either weft arrangement 4637 or weft arrangement 4639 for the same reason. Additionally, in some forms, manufacturing may be difficult due to the large size of the monofilament of thread no. 5. In some forms, multiple monofilament strands of larger sizes may kink during manufacturing and cause the weaving machine to malfunction causing an inconsistent weave structure and non-uniform appearance of the tubular structure.

As shown in FIG. 22, weft arrangement 4641 includes a pattern of weft threads that will repeat along the length of a tubular structure that includes weft arrangement 4641. This is due to the arrangement of shuttles 4702 within weaving machine 4700. Shuttles 4702 are located in a track and therefore the arrangement of the weft threads is consistent along the length of a tubular structure. Weft arrangement 4641 includes a weft pattern 4671. This weft pattern includes a no. 5 thread adjacent to a no. 5 thread. The second no. 5 thread is adjacent a no. 2 thread. The no. 2 thread is adjacent a no. 4 thread. The no. 4 thread is adjacent to another no. 4 thread. The second no. 4 thread is adjacent to a no. 3 thread. This pattern of threads then repeats itself along the length of the tubular structure. In this example, weft pattern 4671 may begin with thread that is deposited by first shuttle 4710. Various other patterns or subsets of patterns may also be included as described previously. This pattern therefore begins at a different shuttle location than the weft pattern 4669 shown in FIG. 21. Other patterns that include two thread types repeating, three thread types repeating or other patterns are possible. Additionally, the "starting" point and ending point of a pattern can be defined differently. For example, a pattern of six threads may be broken into two repeating patterns of three threads. These pattern arrangements may be helpful when manufacturing a tubular structure to understand the materials and quantities required to form a particular quantity of a tubular structure.

Referring now to FIG. 23, a schematic of a portion of weft arrangement 4643 is depicted. As shown, a particular arrangement of materials is utilized as produced in chart 4634. In the configuration of FIG. 23, thread no. 1 is used in the first shuttle position. Thread no. 1 is also utilized in the second shuttle position. Thread no. 6 is utilized in the third shuttle position. Thread no. 4 is utilized in the fourth shuttle position. Thread no. 4 is utilized in the fifth shuttle position. Thread no. 6 is utilized in the sixth shuttle position.

The configuration of weft arrangement 4643 is similar to other weft arrangements but includes some differences. Weft arrangement 4643 is similar to weft arrangement 4639 in that weft arrangement 4643 includes two thread no. 1 threads adjacent to one another. Next to each of these thread no. 1 threads, however, is thread no. 6. This thread may have a lower dtex number and different construction than either thread no. 2 or thread no. 3 as utilized in weft arrangement 4639. Additionally, this thread may be the same thread type that is used in the warp direction of weft arrangement 4643. By utilizing thread no. 6 a greater fabric or cloth appearance and feel may be imparted onto a tubular structure including weft arrangement 4643 when compared to other forms. This may be pleasing to a patient that may find the cloth and fabric appearance comforting thereby increasing likelihood of continued use of a therapy device that includes weft arrangement 4643. Further, thread no. 6 may be more flexible than other threads such as thread no. 2 and thread no. 3 utilized in other forms. Utilizing thread no. 6 may permit weft arrangement 4643 to be more flexible than other forms while also maintaining structural integrity of the tubular structure through the use of thread no. 1. Thread no. 1 may provide a helical coil to a tubular structure.

Additionally, the configuration of weft arrangement 4643 includes a fewer number of different threads than previous forms. By configuring weft arrangement 4643 with fewer different threads, the cost of construction of weft arrangement 4643 may be lower when compared to other tubular structures that include a greater number of different threads.

In addition to providing lower costs compared to tubular structures that include weft arrangements with a greater number of different weft threads, weft arrangement 4643 may be particularly formed to provide a consistent uniform construction. The uniform construction may assist in providing an acceptable outer surface to a consumer. That is, because the pattern is "symmetrical" about an imaginary line between the two no. 4 threads, the tubular structure constructed with such a weft arrangement may have a particularly uniform look.

Referring now to FIG. 24, a schematic of a portion of weft arrangement 4645 is depicted. As shown, a particular arrangement of materials is utilized as produced in chart 4634. In the configuration of FIG. 24, thread no. 1 is used in the first shuttle position. Thread no. 5 is utilized in the second shuttle position. Thread no. 6 is utilized in the third shuttle position. Thread no. 4 is utilized in the fourth shuttle position. Thread no. 4 is utilized in the fifth shuttle position. Thread no. 6 is utilized in the sixth shuttle position.

The configuration of weft arrangement 4645 is similar to that of weft arrangement 4643. Weft arrangement 4645, however, includes thread no. 1 in the first shuttle position and thread no. 5 in the second shuttle position. The configuration of weft arrangement 4645 may have greater stability than that of weft arrangement 4643 while also maintaining flexibility and bendability. Utilizing two different sized monofilament threads in the first shuttle position and the second shuttle position, however, may influence the outer shape of weft arrangement 4645. For example, the different sized monofilaments may provide an uneven shape to the outer surface of weft arrangement 4645. This may provide a particular texture to the outer surface. In some forms, the texture may be modified depending on the shape and size of the weft threads within the tubular structure, for example as shown in FIG. 20, the texture of tubular structure 4600 may be influenced by the shape and size of the weft threads.

In addition to providing particular strength and stretch characteristics, in some forms, the material utilized to form a tubular structure may be lightweight when compared to other tubular structures that are not formed via circular weaving, braiding, knitting, or another network of interlocking fibers. Additionally the material utilized to form tubular structure 4600 may be soft to the touch such that the material is comfortable to the patient.

In some forms, a heating element may be included within tubular structure 4600. The heating element may be utilized to provide heat to the air as it is supplied to the patient. Additionally, in some forms, the heating element may provide support to tubular structure 4600. For example, the monofilament materials such as thread no. 1 and thread no. 5 may be replaced with conductive wires. These wires may be able to provide support to tubular structure 4600 while also being able to provide a conductive path for electricity to provide heat to the air circuit 4170 during use.

In some forms, a monofilament thread may be located adjacent to another monofilament thread. In some forms, a non-monofilament thread may be located between two monofilament threads. In some forms, the two monofilament threads may be different physical threads. In further forms, a plurality of non-monofilament threads may be located between monofilament threads. The number of monofilament threads and non-monofilament threads may be adjusted based on the desired flexibility and strength of the tubular structure. Additionally, the arrangement of a monofilament separated from another monofilament by a multifilament may be accomplished through various weft arrangements. For example, in some forms a weft pattern utilizing all the available shuttles may have pattern that includes a monofilament that is spaced from another monofilament by at least one non-monofilament thread. For example, weft pattern 4669 described previously has such an arrangement.

In other forms, a tubular structure that includes a monofilament spaced from another monofilament by at least one non-monofilament may be achieved by repeating a pattern a second time. For example, weaving machine 4700 may be fitted with a single monofilament weft thread and five non-monofilament weft threads on the shuttles 4702. During formation of a tubular structure, the first pattern formed will include a single monofilament and five non-monofilament threads. Once the shuttles 4702 of weaving machine 4700 rotate a second time, and therefore repeat the pattern a second time, the weft configuration would include a single monofilament, five non-monofilaments, the single monofilament, and then five non-monofilaments. In this manner, a monofilament thread is spaced from a monofilament thread by five non-monofilament threads. Along a linear length of a tubular structure, therefore, a monofilament is spaced from a monofilament by at least one non-monofilament. Although the monofilament thread in this configuration is the same monofilament thread throughout the tubular structure, the tubular structure may still be considered to have a monofilament thread that is spaced from a monofilament thread by at least one non-monofilament thread.

In some forms, multiple monofilament threads may be located adjacent to one another as shown, for example, in FIG. 23. By utilizing two monofilament threads next to each other the strength and resiliency of a tubular structure that includes a weft arrangement such as weft arrangement 4643 may be increased with minimal impact to the look and feel of the tubular structure. Weft arrangement 4643 includes two monofilament threads, rather than including a single larger monofilament thread. By utilizing two smaller monofilament threads a smaller profile of a tubular structure may be formed while also maintaining strength and resiliency within a tubular structure when compared to a single larger monofilament thread.

Although particular weft arrangements and thread configurations are discussed, other configurations are possible. The configurations presented are for explanatory purposes of providing some possible arrangements. Each thread could we swapped for another thread. For example, rather than utilizing two no. 4 threads adjacent one another in weft arrangement 4643, the no. 4 threads may be swapped with two no. 3 threads. Further, the configuration of threads can be manipulated for any combination of threads. For example a no. 5 thread could be adjacent to both a no. 4 thread and a no. 3 thread. Any configuration and reconfiguration is possible. Further, the particular threads described are not exhaustive and are for explanatory purposes to depict particular forms of the present technology. Different threads with different material constructions such as polyester, polyamide, polyurethane, cotton, wool, elastane, and other materials are envisioned. Thread configurations that are coated and non-coated, with a core or without a core, textured, crimped, Z twisted, S twisted, spun, extruded and other configurations are also envisioned. The list of materials is by no means exhaustive.

Each weft arrangement may be formed of various threads. The configuration and order of the threads, however, may be varied or changed depending on the particular properties sought within the tubular structure or air circuit that incorporates the tubular structure. Weft configuration 4635 utilizes thread nos. 1 through 4. Weft configuration 4637 utilizes thread nos. 1 through 5. Weft configuration 4639 utilizes thread nos. 1 through 4. Although weft configuration 4639 utilizes that same thread types as weft configuration 4635, the arrangement and layout of the threads within weft configuration 4639 and weft configuration 4635 are different from each other. Weft configuration 4641 utilizes thread nos. 2 through 5. Weft configuration 4643 utilizes thread nos. 1, 4, and 6. Weft configuration 4645 utilizes thread nos. 1, 4, 5, and 6. As shown, the thread types and arrangements of the particular threads are changeable and interchangeable to form any weft arrangement.

Referring to FIG. 35, a selection matrix 4800 is depicted. Selection matrix 4800 is utilized to show the various different thread combinations that may be used to form a tubular structure or weft arrangement or pattern within a tubular structure. Selection matrix 4800 includes a shuttle position column which depicts various shuttles of weaving machine 4700. Although depicted with six shuttles, as described previously, different weaving machines with a greater number of shuttles or a fewer number of shuttles may be utilized. Further, as depicted in selection matrix 4800 there are various thread types that may be utilized on any one of the shuttles. As shown, each thread can be selected ("Yes") or not selected ("No") to be on any one or more of the shuttles. If a particular thread is selected for any shuttle, the selection does not prohibit the same thread from being selected for any other shuttle. For example, thread no. 1 could be utilized on shuttle 1, shuttle 2, and shuttle 3. Thread no. 2 may be utilized on shuttle 4, shuttle 5, and shuttle 6. Additionally, thread no. 1 could be utilized on all or none of the shuttles. It should be recognized that any one thread in the selection matrix 4800 can be utilized on any one or more shuttles. Further, multiple shuttles may have the same type of thread. In other forms, the shuttles may all have different types of threads. In other forms, any one of the shuttles may have a combination of any of the threads. For example, a thread formed from thread no. 1 and thread no. 2 may be utilized on any one or more of the shuttles.

Each thread may be selected for particular properties. For example, each thread may be selected for a particular dtex number, elastic properties, luster, softness, moisture wicking properties, tensile strength, hardness, softness, denier, diameter, appearance and may other factors. The threads may be selected for any one of the shuttles to provide any particular property to the tubular structure. Further, although particular threads are described in the selection matrix 4800, any variation of the threads or different threads may also be utilized. For example, monofilament thread may be selected with different diameters or tensile strength. Further, threads with various dtex number may be utilized that are not formed with the particular material described in the specification. For example, thread no. 2 is PA 6.6 Z150 with 880 dtex. A different thread type that is formed of different materials, for example, polyurethane with a dtex of 880 may also be utilized.

In addition, the selection matrix 4800 may also be applicable to the various warp threads. That is, the warp threads may be formed of any combination of one or more of the thread types described in this specification as well as the variations described. For example, half of the warp threads may be thread no. 3 and the other half of the warp threads may be thread no. 6. The positioning of the warp threads may also be particularly chosen in a similar manner as to that of the weft threads. That is, every other warp thread may be thread no. 3 thread and thread no. 6. Therefore, any one warp thread or weft thread may be selected from the materials described in this specification. Additionally, selecting a particular thread would not remove the thread from being selected at another position within the tubular structure.

5.5.3.5 Tubular Structure Characteristics

A tubular structure 4600 may be formed so that the tubular structure is able to maintain its cross-sectional shape. In some forms, tubular structure 4600 may be configured to also maintain its shape when subjected to external forces. As depicted in FIG. 10, air circuit 4170 that includes tubular structure 4600 may be able to change shape when subjected to force such that tubular structure 4600 is not a rigid structure (see definitions) however air circuit 4170 is able to remain open so that air is permitted to pass through. Tubular structure 4600, however, is also not a floppy structure, in at least one direction. Along the weft direction, tubular structure 4600 may be able to support its own weight. That is, when no additional forces are placed upon or within tubular structure 4600, the cross-section of tubular structure 4600 along the weft direction will remain open. In contrast, tubular structure 4600 may be floppy along its length (see definitions). For example, if tubular structure 4600 is held at one end, along its length or warp direction, tubular structure 4600 may not be able to support its own weight and will bend. The amount of bend will depend on the length of tubular structure 4600. For example, a longer tubular structure 4600 will bend to a greater degree than a shorter tubular structure 4600. Even when bent, however, tubular structure 4600 may remain open so that air is permitted to pass through tubular structure 4600.

In some forms, a tubular structure 4600 may be able to maintain its shape when subjected to a compressive force of 1 kilogram tending to occlude the tubular structure. In other forms, the tubular structure 4600 may be able to maintain its shape when subjected to a 5 kilogram force. In other forms, the tubular structure may be able to maintain its shape when subjected to between 1 and 5 kilograms. In still further forms, tubular structure 4600 may be able to maintain its shape when subjected to a force of between 0 and 10 kilograms.

In some forms, an occlusion force may cause tubular structure 4600 to collapse, thereby closing or greatly reducing the cross sectional area of the tubular structure 4600. This may occur, for example, if a patient steps on tubular structure 4600. Upon removal of the force, tubular structure 4600 may spring back to shape so that air is permitted to travel freely through tubular structure 4600. In this manner, tubular structure 4600 may be resilient (see Definitions).

Further, tubular structure 4600 may be able to be compressed longitudinally and maintain its shape. In a configuration in which tubular structure 4600 includes a ribbed structure for example, the valleys 4620 may be compressed along with the ridges 4618 such that the overall length of tubular structure 4600 may be diminished, however tubular structure 4600 remain open to permit the passage of air through tubular structure 4600 or an air circuit that includes tubular structure 4600. In addition to being longitudinally compressible, tubular structure 4600 may also be able to be stretched to an elongated state, for example, as shown in FIG. 18. During elongation, air may be permitted to flow through tubular structure 4600 or an air circuit that include tubular structure 4600.

5.5.3.6 Air Loss

In some forms, tubular structure may be constructed to have a particular leak rate. In some forms, the leak rate may be particularly chosen or tested to determine if and what type of post-processing may be necessary or desired. Additionally, in some forms a particular leak rate may be desired to remove waste air. In some forms, the leak per meter of a tubular structure may be between 300 and 2000 mL/min at a pressure of 3 cmH$_2$O. In some forms, the leak per meter of a tubular structure may be between 500 and 2300 mL/min at a pressure of 4 cmH$_2$O. In some forms, the leak per meter of a tubular structure may be between 700 and 2900 mL/min at a pressure of 7 cmH$_2$O. In other forms, the leak per meter of a tubular structure may be between 900 and 3200 mL/min at a pressure of 8 cmH$_2$O. In some forms, the leak per meter of a tubular structure 4600 may be approximately 1100 mL/min at a pressure of 3 cmH$_2$O. In other forms the leak rate per meter may be approximately 1380 mL/min at a pressure of 4 cmH$_2$O. In other forms the leak rate per meter may be approximately 1550 mL/min at a pressure of 5 cmH$_2$O. In other forms the leak rate per meter may be approximately 1650 mL/min at a pressure of 6 cmH$_2$O. In other forms the leak rate per meter may be approximately 1750 mL/min at a pressure of 7 cmH$_2$O. In other forms the leak rate per meter may be approximately 1820 mL/min at a pressure of 8 cmH$_2$O. The leak rates may be utilized to determine what type of coating or coating technique may be appropriate to utilize with a particular tubular structure.

5.5.4 Leak Reduction

In some forms, a tubular structure may be utilized on conjunction with an air therapy device in the form of air circuit 4170. In some forms, a lower pressure leak rate may be desired so that the air circuit is able to deliver air at a particular pressure to the patient at a consistent and particular therapeutic pressure. In some forms the air circuit 4170 may be designed to provide air at a pressure of 4 cmH$_2$O. In other forms, air circuit 4170 may be designed to provide air at a pressure of 6 cmH$_2$O. In still further forms, air circuit 4170 may be designed to provide air at a pressure of 8 cmH$_2$O. In some forms, when air circuit 4170 is delivering air at a therapeutic pressure air circuit 4170 is configured to have a leak rate of 2.5 mL/min per meter. In other forms, air circuit 4170 is configured to have a leak rate less than 2.5 mL/min per meter. In some forms, air circuit 4170 is configured to have a non-zero leak rate. In some forms, providing a specific leak rate within air circuit 4170 or other component that utilizes tubular structure 4600 and or sealing structure 4650 may permit the removal of a separate vent.

In some forms, tubular structure 4600 may be lined with a material that is configured to contain or retain air so that the air does not leak through tubular structure 4600 or leaks below a given threshold such as at or below 2.5 mL/min per meter. For example, as shown in FIG. 15 air circuit 4170 includes tubular structure 4600 along with a sealing structure 4650. In some forms, sealing structure 4650 may be formed of silicone or silicone rubber. In other forms other sealing materials such as acrylate may be utilized. In still other forms, other materials such as elastomeric material, polyurethane, thermoset, and/or thermoplastic materials may be utilized. In other forms, sealing structure 4650 may be formed of a biocompatible material. In still further forms, sealing structure 4650 may be formed of a soft, flexible and resilient material.

In some forms, the sealing structure may be formed such the sealing structure 4650 is a pre-formed tube such as an extruded silicone tube. In such forms, tubular structure 4600 may be wrapped about sealing structure 4650. In some forms, sealing structure 4650 may be overwoven by tubular structure 4600, or overbraided or over-knitted by tubular structure 4600. Tubular structure 4600 may be secured to sealing structure 4650 through a separate material such as an adhesive between tubular structure 4600 and sealing structure 4650.

In some forms, the sealing structure may be formed after the formation of tubular structure 4600. In some forms, a liquid material may be sprayed on the interior of the tubular structure 4600. The sealing material may then cure to form a solid sealing structure.

In other forms, a separate sealing structure may not be utilized. In some forms, tubular structure 4600 may be pre-formed to have adequate sealing properties. In some forms, tubular structure 4600 may be formed with elastomeric materials such that resist water and/or air leakage. By forming tubular structure 4600 with threads formed of particular materials the weight of an air circuit that utilizes a leak reducing tubular structure 4600 may be less than that of an air circuit that utilizes a tubular structure 4600 with a separate sealing structure.

The thickness of the sealing structure may be varied such that properties of air circuit 4170 may also be varied. In some forms, sealing structure 4650 may be between 0.1 and 5 millimeters. In some forms, sealing structure 4650 may be between 0.25 and 4 millimeters. In still further forms, sealing structure 4650 may be between 0.5 and 3.5 millimeters. In still further forms, sealing structure 4650 may be between 1 and 4 millimeters. In some forms, sealing structure 4650 may have a thickness of approximately 1 millimeter. In other forms, sealing structure 4650 may have a thickness of approximately 0.65 millimeters. In still further forms, sealing structure 4650 may have a thickness of between 0.55 millimeters and 0.6 millimeters. Varying the thickness of the sealing structure may impact the ability of air circuit 4170 to bend or stretch. For example, a thicker sealing structure 4650 of a given material may stretch to a lesser extent than a thinner sealing structure 4650. Likewise, a thicker sealing structure 4650 may require a greater amount of force to bend than a thinner sealing structure 4650. Therefore, modifying the thickness of sealing structure 4650 changes the physical properties of sealing structure 4650.

Sealing structure 4650 may be secured to tubular structure 4600 to form a tubular portion of air circuit 4170. When secured to tubular structure 4600, sealing structure 4650 may impact the stretch and bending characteristics of tubular structure 4600 in the same manner as described above.

In some forms, tubular structure 4600 may be secured to sealing structure 4650 through the use of glue or other adhesive. In some forms the adhesive may air dry, and in other forms the adhesive may be set by utilizing Ultra Violet ("UV") or other device. In still other forms, sealing structure 4650 and tubular structure 4600 may be joined together without the use of an adhesive. In still further forms, sealing structure 4650 may be directly connected with tubular structure 4600 solely through the material of sealing structure 4650. For example, in some forms sealing structure 4650 may be applied to tubular structure 4600 in liquid form. Sealing structure 4650 may dry and cure with tubular structure 4600 such that another material need not be used to join tubular structure 4600 with sealing structure 4650.

The strength of the sealing structure 4650 may also be varied to alter or modify the characteristics of air circuit 4170. Sealing structure 4650 may be formed with material that is between 15 shore and 75 shore. In other forms sealing structure 4650 is formed with a material that is between 10 shore and 60 shore. In still further forms, sealing structure 4650 is formed of a material that is between 25 and 50 shore. In some forms, sealing structure 4650 may be formed with silicone that is 60 shore. In other forms, sealing structure 4650 may be formed with silicone that is 45 shore. In still further forms, sealing structure 4650 may be formed with silicone that is 26 shore. In other forms, sealing structure 4650 may be formed with silicone that is less than 26 shore. Varying the hardness or strength of sealing structure 4650 may impact the properties of air circuit 4170. For example, a harder sealing structure 4650 may resist bending or occlusion to a greater degree than a softer sealing structure 4650. Too hard of a sealing structure 4650, however, may cause air circuit 4170 to kink when bent. This is because too hard of a material may not be able to stretch or compress to accommodate a bend of air circuit 4170 but rather will kink.

The hardness of the sealing structure 4650 may be selected or tuned along with the thickness to achieve a particular property. For example, a sealing structure 4650 with a higher shore number may be formed in a thinner arrangement than a sealing structure 4650 with a lower shore number. The thickness and shore number may be varied depending on the desired end properties of air circuit 4170.

In some forms, particular thicknesses and shore hardnesses of sealing structures may be utilized. In one form, the sealing structure 4650 is 1 millimeter in thickness and 60 shore. In other forms, sealing structure 4650 has a 0.65 millimeter thickness with 45 shore. In still another form, sealing structure 4650 has a thickness of 0.55 to 0.6 millimeters with 26 shore. These various configurations may be utilized to achieve a particular property or function of air circuit 4170.

In addition to reducing air loss, a sealing structure may also assist in managing water within air circuit 4170. In some forms, sealing structure 4650 may be water resistant. During use of a therapy device, the air supplied to the patient may be humidified. Additionally, gas expired by the patient may also have a relative humidity higher than surrounding air. In some forms, during use the humidified air may condense into water and line the air circuit 4170. Sealing structure 4650 may direct the water to a particular location and may also prevent water from leaking through tubular structure 4600.

5.5.4.1 Weight of Sealing Structure

In some forms, air circuit 4170 may be formed with a sealing structure 4650 that weighs a particular amount. In some forms, the sealing structure may be formed such that sealing structure 4650 imparts a minimal amount of weight to air circuit 4170. Sealing structure 4650 may be designed in such a manner to minimize or reduce the impact that sealing structure 4650 has on the weight and flexibility of air circuit 4170. For example, sealing structure 4650 may be formed in a thin manner so that the amount extra or additional weight and material utilized within air circuit 4170 may be reduced or minimized.

In some forms, sealing structure 4650 may weigh less than a tubular structure 4600 of the same or similar length. In some forms, two meters of tubular structure 4600 may weigh between 25 grams and 100 grams. In other forms, tubular structure 4600 may weigh between 15 and 75 grams. In still further forms, tubular structure may weigh between 30 and 60 grams. For example, in some forms 2 meters of tubular structure 4600 may weigh approximately 64 grams. A corresponding length of sealing structure 4650 may be formed along an interior surface of tubular structure 4600. In some forms, sealing structure 4650 may weigh between 50 and 200 grams. In other forms, sealing structure 4650 may weigh between 75 and 125 grams. In still further forms sealing structure 4650 may weigh between 25 and 60 grams. In some forms, sealing structure 4650 may weigh approximately 80 grams. In other forms, sealing structure 4650 may weigh approximately 72 grams. In still further forms, sealing structure 4650 may weigh 64 grams. In further forms, sealing structure 4650 may weigh 60 grams or even 40 grams or less than 40 grams. Therefore, sealing structure 4650 may weigh approximately 1.25 times as much as tubular structure 4600. Sealing structure 4650 may also weigh less than 1.25 as much as tubular structure 4600. In some forms, sealing structure 4650 may weigh 1.13 times as much as tubular structure 4600. In still further forms, sealing structure 4650 may weigh approximately the same as tubular structure 4600. In further forms, sealing structure 4650 may weigh less than tubular structure 4600. For example, sealing structure 4650 may weigh 94% of the weight of tubular structure 4600. In still further forms, sealing structure 4650 weigh 62% of the weight tubular structure 4600. In this manner, a lightweight air circuit 4170 that incorporates tubular structure 4600 and sealing structure 4650 may be formed. In still further forms, sealing structure 4650 may weigh between 62% of the weight of tubular structure 4600 and 1.25 times the weight of tubular structure 4600. In still further forms, sealing structure 4650 may weight more than 1.25 times the weight of tubular structure 4600 or may weigh less than 62% of tubular structure 4600. In some forms, the weight of sealing structure 4650 may be 50%, 75% or the same as the weight of tubular structure 4600. In still further forms, the weight of sealing structure 4650 may be between 25% and 90% of the weight of tubular structure 4600. In still further forms, the weight of sealing structure 4650 may be between 1 and 2 times as much as the weight of tubular structure 4600.

In some forms, the weight of sealing structure 4650 may be impacted by the thickness and material composition of sealing structure 4650. Therefore, the weight of sealing structure 4650 may be altered by changing the material composition of sealing structure 4650 as well as the thickness of sealing structure 4650.

5.5.4.2 Sealing Structure Configuration

In some forms, sealing structure 4650 may follow the contours of tubular structure 4600. In some forms, as discussed previously, tubular structure 4600 may have a ribbed shape such that tubular structure 4600 includes crests or ridges and valleys. Similarly, sealing structure 4650 may also include ridges and valleys. The interior surface of tubular structure 4600 may include a ribbed surface that includes ridges and valleys. Referring to FIG. 33 a portion of air circuit 4170 is depicted that includes tubular structure 4600 as well as sealing structure 4650. As shown, interior surface 4660 of tubular structure 4600 includes ridges and valleys. Outer surface 4652 of sealing structure 4650 corresponds with interior surface 4660 of tubular structure 4600 and follows the same or similar path as interior surface 4660 of tubular structure 4600. That is, outer surface 4652 of sealing structure 4650 has an opposite curvature when compared to interior surface 4660 of tubular structure 4600. For example, when outer surface 4652 of sealing structure 4650 has a positive curvature, interior surface 4660 of tubular structure 4600 has an opposite negative curvature.

Additionally, inner surface 4654 of sealing structure 4650 may mimic or relate to interior surface 4660 of tubular structure 4600. For example, inner surface 4654 may have a positive curvature at the same or similar longitudinal location as interior surface 4660 of tubular structure 4600. In other forms, inner surface 4654 may have a positive or negative curvature similar to the curvature of interior surface 4660 of tubular structure 4600 however the magnitude of the curvature may be less positive or less negative. The curvature of inner surface 4654 may be more muted or gradual than that of interior surface 4660. The curvature of inner surface 4654 may be dependent on the thickness of sealing structure 4650. For example, a thicker sealing structure 4650 may result in more muted or gradual curvature when compared to a thinner sealing structure 4650. Inner surface 4654 bounds the channel of air circuit 4170 that delivers air to the patient. In this manner, the thickness and shape sealing structure 4650 determines the cross-sectional shape of the channel of air circuit 4170. The channel or passageway may be referred to as the open space that is formed or bounded be an inner surface, such as inner surface 4654.

Additionally, in some forms, the distance between the surfaces of tubular structure 4600 and sealing structure 4650 may remain substantially constant along a length of tubular structure 4600 and sealing structure 4650. For example, as shown in FIG. 33, distance d1 from interior surface 4660 to inner surface 4654 of sealing structure 4650 is substantially the same as distance d2 from interior surface 4660 to inner surface 4654 of sealing structure 4650. In this sense sealing structure 4650 may mate with the interior surface 4660 along a length of tubular structure 4600 from rib to rib.

In other forms as shown in FIG. 34, sealing structure 4650 may be a stand-alone structure onto which tubular structure 4600 is secured. For example, sealing structure 4650 may be formed with a substantially circular cross-section that includes an inner surface 4654 and outer surface 4652 that have a curvature of approximately zero along the length of sealing structure 4650. Tubular structure 4600 may be fitted around sealing structure 4650, however, there may be gaps between the ridges and valleys of interior surface 4660 of tubular structure 4600 and the outer surface 4652 of sealing structure 4650. This is because sealing structure 4650 may not be formed to correspond to the shape of tubular structure 4600. In the form as depicted in FIG. 34, tubular structure 4600 may be secured to sealing structure 4650 at contact points such as at point 4664 through the use of adhesive or other bonding mechanism. In other forms, sealing structure 4650 may be heated such that sealing structure 4650 partially melts so that the fibers or strands or tubular structure 4600 interact with sealing structure 4650 to form a bond between tubular structure 4600 and sealing structure 4650. In other forms, tubular structure 4600 may be configured with thermoset or thermoplastic material such that components of tubular structure 4600 partially melt and then cure to form a bond between tubular structure 4600 and sealing structure 4650.

Additionally, in some forms, the distance between the surfaces of tubular structure 4600 and sealing structure 4650 may change along a length of tubular structure 4600 and sealing structure 4650. For example, as shown in FIG. 34, distance d3 from interior surface 4660 to inner surface 4654 of sealing structure 4650 is different from distance d4 from interior surface 4660 to inner surface 4654 of sealing structure 4650.

In other forms, sealing structure 4650 may have a substantially planar longitudinal inner surface 4654 and have an outer surface 4652 that corresponds to the interior surface 4660 of tubular structure 4600. Such a configuration would be similar to a combination of the forms depicted in FIGS. 33 and 34. In this manner, the material of sealing structure 4650 may fill the space between the valleys of tubular structure 4600.

In some forms, the inner diameter of sealing structure 4650 may be particular selected. In some forms, the innermost diameter of sealing structure 4650 is between 10 and 25 millimeters. In some forms the innermost diameter of sealing structure 4650 is between 8 and 17 millimeters. In still further forms, the innermost diameter of sealing structure 4650 is between 11 and 20 millimeters. In some forms, the inner diameter of sealing structure 4650 is approximately 14 millimeters. In other forms, the inner diameter of sealing structure 4650 is 14.5 millimeters or 15 millimeters. In still further forms, the inner diameter of sealing structure 4650 is greater than 15 millimeters. In other forms, the inner diameter of sealing structure 4650 is less than 14 millimeters. The inner diameter of sealing structure 4650 may be influenced by the inner diameter of tubular structure 4600 as well as the thickness of sealing structure 4650. The inner diameter may be varied to accommodate different quantities of air at different pressures for use in connection with RPT device 4000. For example, to maintain a particular pressure within air circuit 4170 and to the patient, the inner diameter may be particular sized to accommodate a quantity of air at a particular pressure.

In addition to providing sealing to air circuit 4170, sealing structure 4650 may also provide structural support to tubular structure 4600. For example, sealing structure 4650 may assist in providing support against force that would tend to occlude air circuit 4170. Sealing structure 4650 however, may be able to be compressed and elongated without obstructing the air path through air circuit 4170. Further, sealing structure 4650 may be able to be axially stretched to at least twice an original length without tearing. Further, when compressed, sealing structure 4650 may compressed in a uniform manner such as to not obstruct an air path through air circuit 4170. Additionally, although sealing structure 4650 may provide additional support to tubular structure 4600, an air circuit 4170 that includes sealing structure 4650 may be able to be packed into a coil or coiled upon itself. This may permit an air circuit 4170 with a tubular structure 4600 and sealing structure 4650 to be able to be packed efficiently and stored efficiently when not in use.

5.5.4.3 Sealing Structure and Tubular Structure in Other Configurations

Tubular structure 4600 and sealing structure 4650 may be utilized in other portions of an air therapy device instead of in addition to air circuit 4170. For example, tubular structure 4600 and sealing structure 4650 may be utilized as a part of patient interface 3000. Tubular structure 4600 may also be utilized without sealing structure 4650 in various areas of a therapy device. For example, tubular structure 4600 may not be utilized to transfer air, but rather may be utilized to provide support for various components. For example, tubular structure 4600 may form a portion of a strap. Additionally, in further forms, an air circuit 4170 may connect to tube formed from a tubular structure 4600 and sealing structure 4650. Additionally, tubular structure 4600 and sealing structure 4650 may be utilized to form various portions of patient interface 300, such as the sealing structure, shroud. Further tubular structure 4600 may be used as a wrap or covering about various components of air therapy device.

5.5.5 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

5.6 Humidifier

5.6.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.6.2 Humidifier Components
5.6.2.1 Water Reservoir

According to one arrangement, the humidifier 5000 may comprise a water reservoir 5110 configured to hold, or retain, a volume of liquid (e.g. water) to be evaporated for humidification of the flow of air. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 5A and FIG. 5B.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

5.6.2.2 Conductive Portion

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

5.6.2.3 Humidifier Reservoir Dock

In one form, the humidifier 5000 may comprise a humidifier reservoir dock 5130 (as shown in FIG. 5B) configured to receive the humidifier reservoir 5110. In some arrangements, the humidifier reservoir dock 5130 may comprise a locking feature such as a locking lever 5135 configured to retain the reservoir 5110 in the humidifier reservoir dock 5130.

5.6.2.4 Water Level Indicator

The humidifier reservoir 5110 may comprise a water level indicator 5150 as shown in FIG. 5A-5B. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

5.6.2.5 Heating Element

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier base 5006 where heat may be provided to the humidifier reservoir 5110 primarily by conduction as shown in FIG. 5B.

5.7 Glossary

For the purposes of the present technology disclosure, in certain forms of the present technology, one or more of the following definitions may apply. In other forms of the present technology, alternative definitions may apply.

5.7.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, $g$-$f/cm^2$ and hectopascal. 1 $cmH_2O$ is equal to 1 $g$-$f/cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.7.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240. (Year? Required?)

Polycarbonate: a thermoplastic polymer of Bisphenol-A Carbonate.

5.7.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 cmH$_2$O pressure.

As an example, an I-beam may comprise a different bending stiffness (resistance to a bending load) in a first direction in comparison to a second, orthogonal direction. In another example, a structure or component may be floppy in a first direction and rigid in a second direction.

5.7.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:

(i) Flattened: Having a rise followed by a relatively flat portion, followed by a fall.

(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.7.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template H(t) is zero-valued at the end of expiration, i.e. $\Pi(\Phi)=0$ when $\Phi=1$, the EEP is equal to the EPAP.

Inspiratory positive airway pressure (IPAP): Maximum desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

5.7.4 Anatomy 5.7.4.1 Anatomy of the Face

Ala: the external outer wall or "wing" of each nostril (plural: alar)

Alar angle:

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

*Glabella*: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius):

Lip, upper (labrale superius):

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion 5.7.4.2 Anatomy of the Skull Frontal bone: The frontal bone includes a large vertical portion, the squama *frontalis*, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.7.4.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.7.5 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.7.6 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.7.6.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.7.6.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical-topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.7.6.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

5.7.6.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

5.8 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

| 5.9 REFERENCE SIGNS LIST | |
|---|---|
| patient | 1000 |
| sleeping patient | 1000 |
| bed partner | 1100 |
| patient interface | 3000 |
| seal - forming structure | 3100 |
| plenum chamber | 3200 |
| chord | 3210 |
| superior point | 3220 |
| inferior point | 3230 |
| stabilising structure | 3300 |
| vent | 3400 |
| connection port | 3600 |
| forehead support | 3700 |
| RPT device | 4000 |
| external housing | 4010 |
| upper portion | 4012 |
| portion | 4014 |
| panel s | 4015 |
| chassis | 4016 |
| handle | 4018 |
| pneumatic block | 4020 |
| air filter | 4110 |
| inlet air filter | 4112 |
| outlet air filter | 4114 |
| muffler | 4120 |
| mufflers | 4120 |
| inlet muffler | 4122 |
| outlet muffler | 4124 |
| pressure generator | 4140 |
| blower | 4142 |
| controllable blower | 4142 |
| motor | 4144 |
| anti - spill back valve | 4160 |
| air circuit | 4170 |
| air circuit | 4171 |

-continued

| 5.9 REFERENCE SIGNS LIST | |
|---|---|
| supplemental oxygen | 4180 |
| electrical components | 4200 |
| PCBA | 4202 |
| power supply | 4210 |
| input device | 4220 |
| central controller | 4230 |
| transducer | 4270 |
| tubular structure | 4600 |
| pin | 4601 |
| woven structure | 4602 |
| warp thread | 4603 |
| warp threads | 4604 |
| warp thread | 4605 |
| weft threads | 4606 |
| deposit weft threads | 4606 |
| weft thread | 4607 |
| edge | 4608 |
| weft thread | 4609 |
| upper edge | 4610 |
| first weft position | 4612 |
| second weft position | 4614 |
| structure | 4616 |
| ridges | 4618 |
| valleys | 4620 |
| inner arc | 4622 |
| outer arc | 4624 |
| tensile force | 4630 |
| chart | 4632 |
| chart | 4634 |
| tubular structure | 4635 |
| tubular structure | 4637 |
| tubular structure | 4639 |
| tubular structure | 4641 |
| tubular structure | 4643 |
| tubular structure | 4645 |
| sealing structure | 4650 |
| outer surface | 4652 |
| inner surface | 4654 |
| interior surface | 4660 |
| point | 4664 |
| weft pattern | 4669 |
| connector | 4670 |
| weft pattern | 4671 |
| connector | 4672 |
| circular weaving machine | 4700 |
| shuttles | 4702 |
| bobbins | 4704 |
| first shuttle | 4710 |
| second shuttle | 4711 |
| third shuttle | 4712 |
| fourth shuttle | 4713 |
| fifth shuttle | 4714 |
| sixth shuttle | 4715 |
| feed direction | 4750 |
| thorn | 4752 |
| selection matrix | 4800 |
| humidifier | 5000 |
| humidifier inlet | 5002 |
| humidifier outlet | 5004 |
| humidifier base | 5006 |
| reservoir | 5110 |
| conductive portion | 5120 |
| humidifier reservoir dock | 5130 |
| locking lever | 5135 |
| water level indicator | 5150 |
| heating element | 5240 |

The invention claimed is:

1. An apparatus for providing positive pressure respiratory therapy to a patient breathing in a respiratory cycle including an inhalation portion and an exhalation portion, said apparatus comprising:
a controllable motor-blower configured to generate a supply of air at a positive pressure relative to ambient pressure by rotating an impeller at an impeller speed, a housing holding said motor-blower, the housing comprising an inlet and a patient-connection port, the patient-connection port being structured to communicate said supply air at said positive pressure from the motor-blower to a patient interface via an air circuit in use;

a sensor to monitor at least one of pressure and a flow rate of the supply of air at positive pressure and to generate a sensor output; and a controller configured to adjust an operating parameter of said motor-blower in accordance with said sensor output to maintain a minimum positive pressure in said patient interface during a treatment session by causing an increase in the impeller speed during the inhalation portion of the respiratory cycle and causing a decrease in the impeller speed during the exhalation portion of the respiratory cycle, the air circuit comprising:
 a tubular structure;
 the tubular structure having a circular woven structure;
 the tubular structure being seamless along a length of the tubular structure;
 the tubular structure including a plurality of warp threads and a plurality of weft threads;
 the plurality of weft threads including a first monofilament weft thread and a second monofilament weft thread;
 the first monofilament weft thread being located adjacent to at least one non-monofilament weft thread, the second monofilament weft thread also being located adjacent to at least one non-monofilament thread; and wherein the at least one non-monofilament thread is located between the first monofilament weft thread and the second monofilament weft thread.

2. The apparatus according to claim 1, wherein the first monofilament weft thread is 0.7 millimeters in diameter.

3. The apparatus according to claim 1, wherein the plurality of warp threads includes 252 warp threads.

4. The apparatus according to claim 1, wherein an outer diameter of the tubular structure is greater than 18 millimeters.

5. The apparatus according to claim 1, wherein the at least one non-monofilament thread includes four non-monofilament threads.

6. The apparatus according to claim 5, wherein the four non-monofilament threads comprise a first weft position, a second weft position, a third weft position, and a fourth weft position.

7. The apparatus according to claim 6, wherein a first non-monofilament thread in the first weft position has a same composition as a fourth non-monofilament thread in the fourth weft position.

8. The apparatus according to claim 7, wherein a second non-monofilament thread in the second weft position has a same composition as a third non-monofilament thread in the third weft position.

9. The apparatus according to claim 8, wherein the first non-monofilament thread is located adjacent to the first monofilament weft thread and the fourth non-monofilament thread is located adjacent to the second monofilament weft thread.

* * * * *